United States Patent
Mohammadpour et al.

(10) Patent No.: US 12,390,225 B2
(45) Date of Patent: Aug. 19, 2025

(54) LINEAR TISSUE CLIPPING DEVICE

(71) Applicant: UNITED STATES ENDOSCOPY GROUP, INC., Mentor, OH (US)

(72) Inventors: Reza Mohammadpour, Willoughby Hills, OH (US); Alex Uspenski, Auburn Township, OH (US); Keith Randall John, Chardon, OH (US); Seth Byers, Madison, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 283 days.

(21) Appl. No.: 18/199,912

(22) Filed: May 19, 2023

(65) Prior Publication Data

US 2023/0371956 A1    Nov. 23, 2023

Related U.S. Application Data

(60) Provisional application No. 63/344,354, filed on May 20, 2022.

(51) Int. Cl.
 *A61B 17/128*  (2006.01)
 *A61B 17/12*  (2006.01)

(52) U.S. Cl.
 CPC  *A61B 17/1285* (2013.01); *A61B 2017/12004* (2013.01)

(58) Field of Classification Search
 CPC ... A61B 17/1285; A61B 17/10; A61B 17/083; A61B 2017/12004; A61B 2017/0034; A61B 2017/00477; A61B 2017/00269; A61B 2017/00818; A61B 2017/00867
 See application file for complete search history.

(56) References Cited

U.S. PATENT DOCUMENTS

| | | | |
|---|---|---|---|
| 3,882,854 | A  | 5/1975  | Hulka et al. |
| 4,576,165 | A  | 3/1986  | Green et al. |
| 6,428,548 | B1 | 8/2002  | Durgin et al. |
| 6,613,060 | B2 | 9/2003  | Adams et al. |
| 6,629,630 | B2 | 10/2003 | Adams |
| 7,014,646 | B2 | 3/2006  | Adams |

(Continued)

FOREIGN PATENT DOCUMENTS

| | | |
|---|---|---|
| EP | 1337187 B1 | 8/2007 |
| EP | 2163206 A1 | 3/2010 |

(Continued)

OTHER PUBLICATIONS

Dinelli et al., First clinical experiences with a novel endoscopic over-the-scope clip system, Endoscopy International Open 2017; 05: E151-E156.

(Continued)

*Primary Examiner* — Ryan J. Severson
(74) *Attorney, Agent, or Firm* — Calfee, Halter & Griswold LLP

(57) ABSTRACT

A tissue clipping device for clipping tissue and methods of using the same. The device includes a tissue clipping assembly for clipping tissue and a drive assembly operable to control the operation of the tissue clipping assembly. The tissue clipping assembly includes a distal arm that is linearly extendable and retractable to clip tissue. The tissue clipping assembly may be decoupled from the drive assembly after tissue is clipped. Additional clipping assemblies may be deployed with the drive assembly to close larger defects.

20 Claims, 57 Drawing Sheets

(56) References Cited

U.S. PATENT DOCUMENTS

| | | |
|---|---|---|
| 8,585,836 B2 | 11/2013 | Carley et al. |
| 9,486,126 B2 | 11/2016 | West et al. |
| 9,603,614 B2 | 3/2017 | Schurr et al. |
| 10,639,031 B2 | 5/2020 | Binmoeller et al. |
| 2011/0077668 A1 | 3/2011 | Gordon et al. |
| 2012/0065657 A1 | 3/2012 | Adams |
| 2014/0100423 A1 | 4/2014 | Monassevitch et al. |
| 2015/0018848 A1 | 1/2015 | Kappel et al. |
| 2020/0178956 A1 | 6/2020 | Mitelberg et al. |

FOREIGN PATENT DOCUMENTS

| | | |
|---|---|---|
| EP | 2449983 A1 | 5/2012 |
| KR | 1020160115163 A | 10/2016 |
| WO | 2010025233 A1 | 3/2010 |
| WO | 2013016066 A1 | 1/2013 |
| WO | 2015127013 A1 | 8/2015 |
| WO | 2016141353 A1 | 9/2016 |
| WO | 2019109029 A1 | 6/2019 |

OTHER PUBLICATIONS

Kapelle et al., Endoscopic full-thickness resection of gastric and duodenal subepithelial lesions using a new, flat-based over-the-scope clip, Surgical Endoscopy p. 2839-2846, published Dec. 27, 2017.

Mangiavillano et al., Over the scope clips in the treatment of gastrointestinal tract iatrogenic perforations, Word Journal of Gastrointestinal Surgery, Apr. 27, 2016, vol. 8, Iss 4, pp. 315-321.

Rajan et al., Endoscopic muscle biopsy sampling of the duodenum and rectum: a pilot survival study in a porcine model to detect myenteric neurons, Gastrointestinal Endoscopy, Jul. 20, 2017, 87(2):600-606; pp. 1-23.

Rajan et al., Innovative gastric endoscopic muscle biopsy to identify all cell types, including myenteric neurons and interstitial cells of Cajal in patients with idiopathic gastroparesis: a feasibility study, Gastrointest Edosc. Sep. 8, 20164(3), pp. 1-16.

Tang et al., Double channel double grasper technique in over the scope clip deployment, Viedo Case Report, Videogie, vol. 5, No. 5, 2020, pp. 141-143.

International Search Report and Written Opinion from PCT/US2023/023028 dated Sep. 18, 2023 (12 pages).

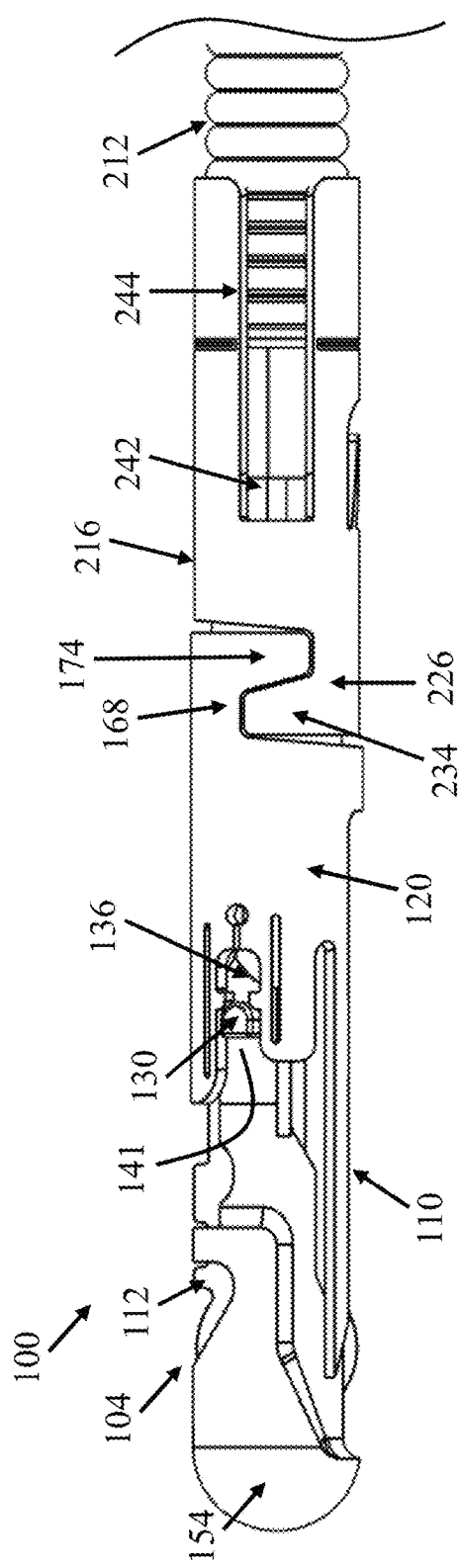
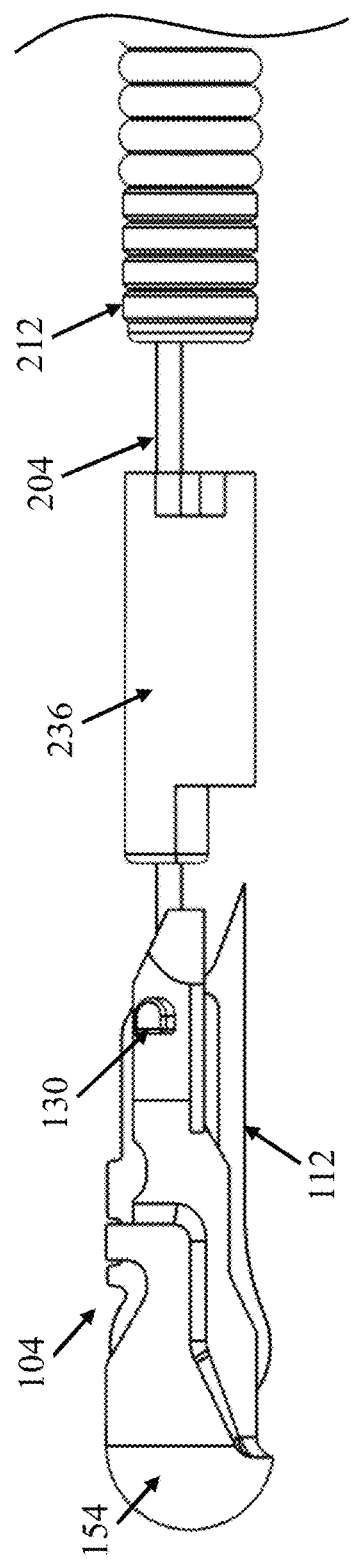
FIG. 29A
FIG. 29B

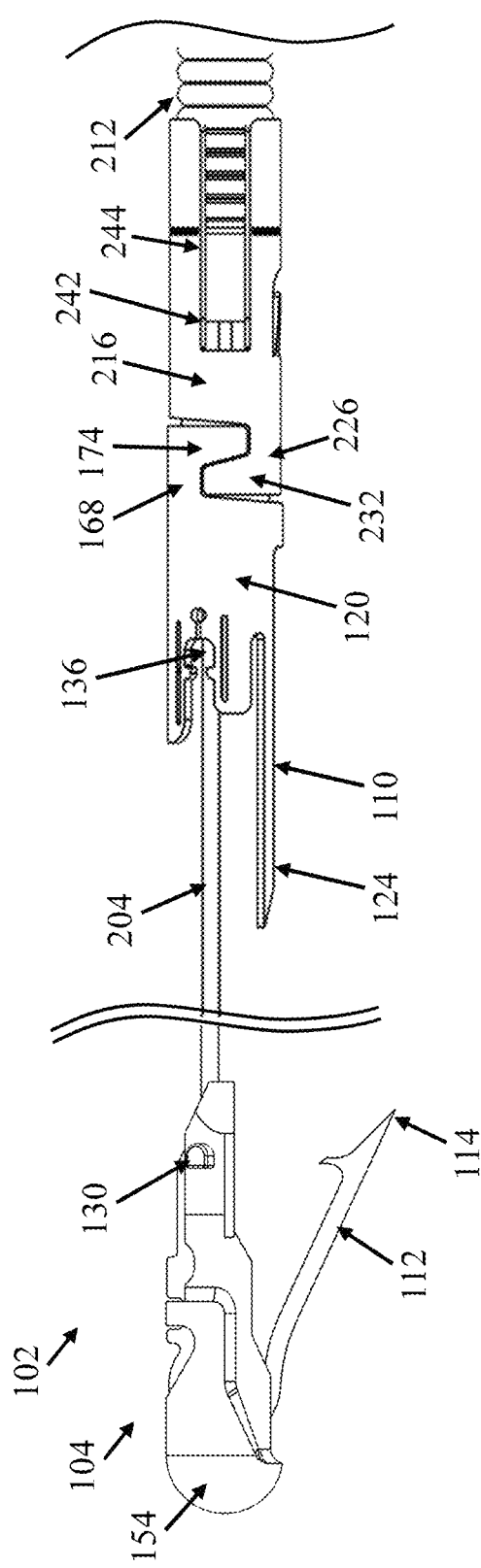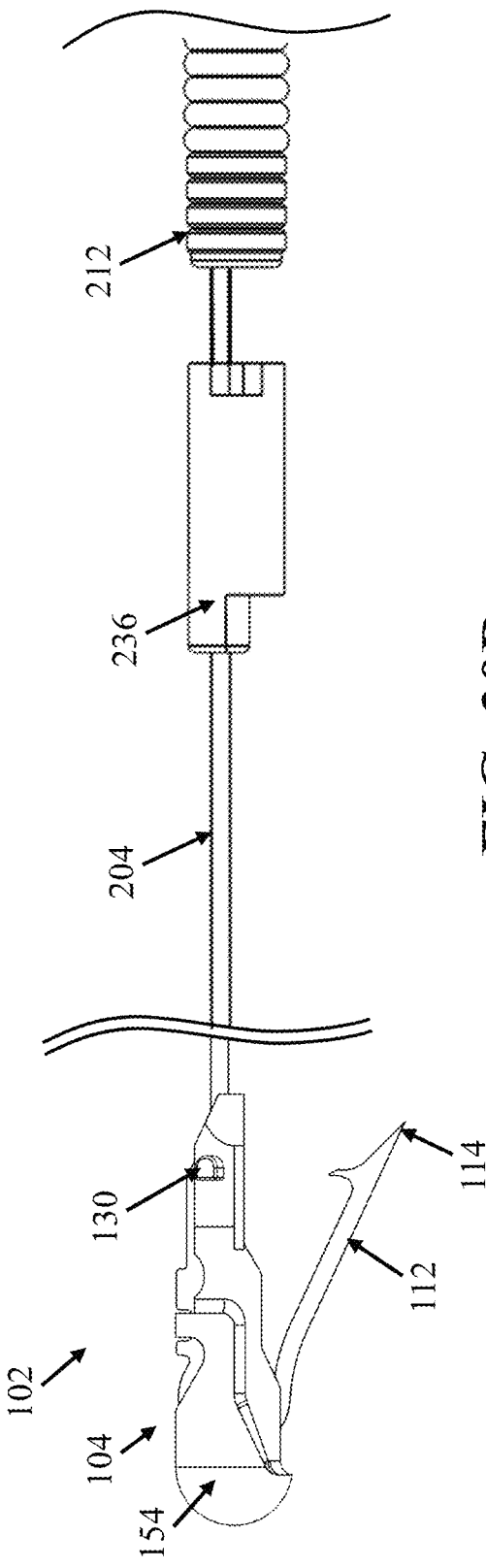
FIG. 30A
FIG. 30B

LINEAR TISSUE CLIPPING DEVICE

CROSS-REFERENCE TO RELATED APPLICATIONS

The present application claims priority to U.S. Provisional Patent Application No. 63/344,354, filed on May 20, 2022, the entire disclosure of which is incorporated herein by reference as though recited herein it its entirety.

TECHNICAL FIELD

The present disclosure relates generally to surgical devices and, more specifically, to a linear tissue clipping device that allows for improved tissue recruitment.

BACKGROUND

Tissue recruitment devices are used in various parts of the body, including the gastrointestinal, urinary, and vascular systems, to recruit tissue, such as tissue from the luminal wall. The tissue recruitment devices may be deployed using an endoscope to recruit tissue such that it may be treated. The tissue recruitment devices may be used with hemostatic devices to treat internal bleeding or defects. Conventional hemostatic devices, such as clamps, clips, staples, and sutures, may be applied around recruited tissue to apply constrictive forces to the tissue, such as to apply a constrictive force to prevent bleeding.

Conventional tissue recruitment devices and hemostatic devices are operated from a position substantially above and perpendicular to the target tissue. However, such tissue recruitment devices and hemostatic devices may be difficult to properly position or operate to recruit and close tissue. For example, the target tissue may be located at a site which is difficult or impossible to access from a conventional perpendicular approach. This may increase the time of the procedure and limit the efficiency of the tissue recruitment and the closure of the target tissue, such as resulting in the recruitment device not adequately recruiting the target tissue and/or the hemostatic device not adequately closing the target tissue.

Accordingly, there are unmet needs for an improved recruiting device and an improved hemostatic device that is conducive for use in a non-perpendicular approach.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. The description herein relates to systems, assemblies, methods, devices, apparatuses, combinations, etc. that may be utilized for hemostatic closure of defects, perforations, ulcers, and other pathologies of the body requiring hemostasis. Various features and steps as described elsewhere in this disclosure may be included in the examples summarized here. Further, the treatment techniques, methods, operations, steps, etc. described or suggested herein can be performed on a living animal or on a non-living simulation, such as on a cadaver, simulator (e.g., with the body parts, tissue, etc. being simulated), etc.

In one example embodiment, a medical device for clipping tissue is provided. The medical device includes a catheter and a collar having a proximal arm extending in a distal direction. A proximal end of the collar is coupled with the distal end of the catheter. The medical device also includes a distal arm having an extending portion and a grasping portion, and a drive element extending through the catheter and coupled with the distal arm. The drive element is operable to linearly translate the distal arm through the collar. The medical device is operable to clip tissue between the proximal arm and the distal arm by linearly retracting the distal arm toward the proximal arm.

In one example embodiment, a medical device for clipping tissue is provided. The medical device includes a tissue clipping assembly operable to clip tissue and including a distal arm, a collar, and a proximal arm. The medical device also includes a drive assembly operable to actuate the tissue clipping assembly and including a handle, a catheter, and a drive element. A proximal end of the drive element is secured to the handle and a distal end of the drive element is operably coupled with a proximal end of the distal arm. The drive element is operable to linearly translate the distal arm to clip tissue between the distal arm and the proximal arm. The tissue clipping assembly is operably decoupled from the drive assembly after the tissue clipping assembly has clipped tissue.

In one example embodiment, a method for treating a defect with a tissue recruiting device is provided. The method includes the steps of positioning a tissue clipping assembly above the defect, linearly extending a distal arm of the tissue clipping assembly to grasp a first side of the defect via a drive assembly, grasping a second side of the defect with a proximal arm of the tissue clipping assembly, retracting the distal arm toward the proximal arm, clipping tissue between the distal and proximal arms, and decoupling the tissue clipping assembly from the drive assembly.

These and other objects, features, and advantages of the present disclosure will become apparent from the following detailed description of illustrative embodiments thereof, which is to be read in connection with the accompanying drawings.

BRIEF DESCRIPTION OF THE DRAWINGS

To further clarify various aspects of implementations of the present disclosure, a more particular description of the certain examples and implementations will be made by reference to various aspects of the appended drawings. These drawings depict only example implementations of the present disclosure and are therefore not to be considered limiting of the scope of the disclosure. Moreover, while the Figures can be drawn to scale for some examples, the Figures are not necessarily drawn to scale for all examples. Examples and other features and advantages of the present disclosure will be described and explained with additional specificity and detail through the use of the accompanying drawings in which:

FIG. 29A is a side view of the tissue clipping assembly of FIG. 23 in a set position;

FIG. 29B is a side view of the tissue clipping assembly of FIG. 29A with the collar and connector removed;

FIG. 30A is a side view of the tissue clipping assembly of FIG. 23 in an extended position;

FIG. 30B is a side view of the tissue clipping assembly of FIG. 30A with the collar and connector removed;

DETAILED DESCRIPTION

Figure 1:
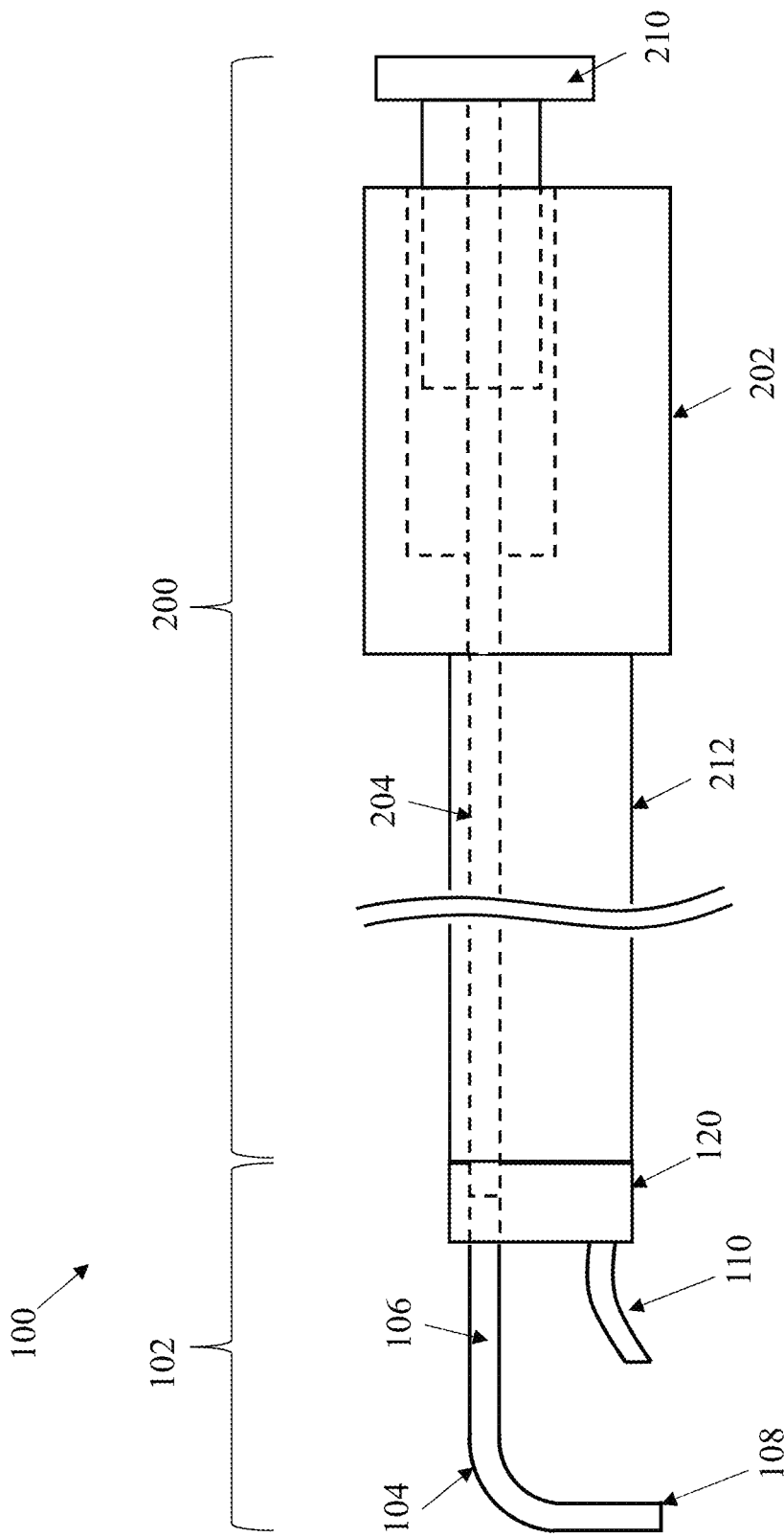
FIG. 1 is a schematic illustration of a tissue clipping device.

The following description refers to the accompanying drawings, which illustrate specific embodiments of the present disclosures, and describes exemplary embodiments in accordance with the general inventive concepts and is not intended to limit the scope of the invention or the claims in any way. Indeed, the invention as described by the claims is broader than and not limited by the exemplary embodiments set forth herein, and the terms used in the claims have their full ordinary meaning.

The general inventive concepts will be understood more fully from the detailed description given below and from the accompanying drawings of the various exemplary aspects and implementations of the disclosure. This should not be taken to limit the general inventive concepts to the specific aspects or implementations, which are being provided for explanation and understanding only. Example embodiments of the present disclosure are directed to devices and methods for clipping tissue. Various embodiments of devices and systems for clipping tissue are disclosed herein, and any combination of these options can be made unless specifically excluded. In other words, individual components of the disclosed devices and systems can be combined unless mutually exclusive or otherwise physically impossible.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

As described herein, when one or more components are described as being connected, joined, affixed, coupled, attached, or otherwise interconnected, such interconnection can be direct as between the components or can be indirect such as through the use of one or more intermediary components. Also, as described herein, reference to a "member," "component," or "portion" shall not be limited to a single structural member, component, or element, but can include an assembly of components, members, or elements.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements. Also, as described herein, the terms "substantially" and "about" are defined as at least close to (and includes) a given value or state (preferably within 10% of, more preferably within 1% of, and most preferably within 0.1% of).

In discussing the exemplary embodiments herein, the terms "proximal" and "distal" may often be used. These terms are used to describe a position or a direction with reference to the operator of the instrument. For example, the proximal position or proximal direction is toward the user or operator of the instrument, and the distal position or direction is away from the user or operator of the instrument, i.e., position or direction toward the object which the operator is attempting to grasp, retain, and/or view. Additionally, relative positional terms such as "up" or "down" and "above" or "below" refer to the position of the component in the context of the figures. Such relative positional terms are used only to facilitate the description and are not meant to be limiting.

The present invention provides a tissue clipping device which may be used in a linear procedural approach parallel to target tissue, such as parallel to the luminal wall. The tissue clipping device may be used closing lesions and/or acutely for hemostasis, such as in endoscopic mucosal resection (EMR), endoscopic submucosal dissection (ESD), full thickness perforations, or upper/lower GI bleeding. The tissue clipping device may be configured to better approximate tissue than standard tissue recruiting devices, such as tissue in the GI tract, such as the colon, small bowel, and esophagus. The tissue clipping device may also be configured to recruit tissue over larger defects than standard tissue recruiting devices and hemostatic clips. For example, the tissue clipping device of the present disclosure may be configured to approximate tissue defects having a width or diameter greater than 10 mm. In some embodiments, the tissue clipping device is configured to approximate tissue defects between 20 mm and 30 mm in width or diameter. The tissue clipping device may be configured to effectively grasp tissue across defects greater than 30 mm in width or diameter. The tissue clipping device may reduce the number of hemostatic devices needed to close a defect. The tissue clipping device may be usable in locations and positions which are less amenable to conventional tissue recruiting devices, such as splenic or hepatic flexures or other articulated positions. In some embodiments, the tissue clipping device may be a sterile, single use device.

A functional block diagram for a tissue clipping device 100 is illustrated in FIG. 1. The tissue clipping device 100 includes a tissue clipping assembly 102 at a distal end and a drive assembly 200 at a proximal end and coupled with a proximal end of the tissue clipping assembly 102. The tissue clipping device 100 is operable to linearly clip tissue, such as in a direction parallel to the tissue. It will be understood that the linear movement and operation of the tissue clipping device 100 refers to a direction substantially parallel to the angle of insertion and operation of the device 100, such as a direction substantially parallel to a distal end of an endoscope, a distal end of a catheter, and/or a surface of the tissue.

The tissue clipping assembly 102 is operable to clip tissue in a linear direction. The tissue clipping assembly 102 includes a distal arm 104 and a proximal arm 110. The distal arm 104 is distally extendable and proximally retractable relative to the proximal arm 110 to clip tissue between the distal and proximal arms 104, 110. The distal arm 104 includes an extending portion 106 extending generally linearly in a distal direction and a grasping portion 108 extending from the extending portion 106. The grasping portion 108 is operable to grasp target tissue such that it may be clipped between the distal arm 104 and the proximal arm 110. The proximal arm 110 is disposed proximally to the distal arm 104, such as proximally from the grasping portion 108 of the distal arm 104. It will be understood that the clipping of the tissue clipping assembly 102 encompasses grasping, grabbing, pinching, hooking, or otherwise securing tissue.

In the illustrated embodiment, the extending portion 106 of the distal arm 104 extends substantially straight, the grasping portion 108 extends substantially downward (e.g., in a direction substantially perpendicular to the linear movement of the tissue clipping assembly 102), and the proximal arm 110 extends distally and downwardly. However, it will be understood that the distal and proximal arms 104, 110 may have other shapes and configurations. For example, the grasping portion 108 of the distal arm 104 may extend proximally toward the proximal arm 110 and the proximal arm 110 may extend substantially distally.

The drive assembly 200 includes a handle 202 operably by a user to control the tissue clipping assembly 102. The drive assembly 200 also includes one or more drive elements 204 coupling the tissue clipping assembly 102 and the handle 202 such that a user may control the tissue clipping assembly 102, such as to clip tissue, via the handle 202. Each drive element 204 may be configured to transfer translational movement to the tissue clipping assembly 102. In some embodiments, the drive elements 204 are configured to transfer rotational movement to the tissue clipping assembly 102. Each drive element 204 may be a solid cable, a hollow tube, a drive cable, a torque cable/shaft, a hypotube, a spring sheath, a catheter, or other device configured to control a component of the tissue clipping assembly 102, or any combination thereof. In some embodiments, the distal ends of the drive elements 204 are fixed to the tissue clipping assembly 102. In other embodiments, the distal ends of the drive elements 204 may be operably decoupled from the tissue clipping assembly 102, as described below.

In the illustrated embodiment, the tissue clipping device 100 includes one drive element 204 with a distal end coupled with the proximal end of the distal arm 104, such as to the proximal end of the extending portion 106 of the distal arm 104, and operable to transmit linear and rotational movement to the distal arm 104. However, it will be understood that the tissue clipping device 100 may include more than one drive element 204. For example, the tissue clipping device 100 may include a second drive element 204 coupled with the proximal arm 110 to control the linear and/or rotational positions of the proximal arm 110 (see FIGS. 3A-3B).

The handle 202 may include a control actuator 210 coupled to the proximal end of each drive element 204. Each control actuator 210 may be operable to control the position and rotation of the coupled drive element 204, such as to control the position and rotation of the tissue clipping assembly 102. For example, a user may linearly translate and rotate the control actuator 210 to linearly translate and rotate a portion of the tissue clipping assembly 102 via one of the drive elements 204. In the illustrated embodiment, the control actuator 210 is a rotational wheel that is linearly slidable within a portion of the handle 202 to control the rotation and translation of the drive element 204. The control actuators 210 may be any suitable device a user may actuate to control the position and/or rotation of one of the drive elements 204. For example, the control actuators 210 may be push buttons, wheels, toggles, switches, levers, triggers, sliders, or the like, or any combination thereof.

The drive assembly 200 also includes a catheter 212 extending distally from the handle 202. The catheter 212 may include one or more lumens extending the length of the catheter 212. The catheter 212 may be sized, shaped, and configured to cover one or more components of the tissue clipping device 100, such as when the device 100 is disposed through an endoscope. The tissue clipping assembly 102 and the drive elements 204 may be extended through the catheter 212, such as through the endoscope, to the desired location in a body. In some embodiments, the proximal arm 110 is coupled to the distal end of the catheter 212. It will be understood that the catheter 212 may be a tube, such as polymer tubing, a sheath, a coil, such as a stainless steel coil, or a composite shaft, such as a braided or coiled polymer, or any combination thereof.

In some embodiments, the catheter 302 comprises polyether ether-ketone (PEEK), a thermos-plastic material, nylon, Pellethane, polytetrafluoroethylene (PTFE), polyimide, composite metal and/or include polymer tubing, metal tubing, metal coils, or a reinforced composite sheath containing a coil and/or braid, or combinations thereof. In a preferred embodiment, the catheters 212 are metal spring sheaths configured to resist compression and operational forces exerted on the catheters 212 by the one or more drive elements 204 as described below. In some embodiments, the catheter 212 is configured to translate and/or rotate the tissue clipping assembly 102, such that an operator may control the position and/or orientation of the tissue clipping assembly 102. In some embodiments, the 212 includes a liner or coating, such as a PTFE liner and/or coating, Polyimide, HDPE, or other lubricious polymer, or any combination thereof, disposed in the one or more lumens to increase the resiliency of the catheter 212 and/or to decrease friction between the one or more drive element 204 and the catheter 212. In some embodiments, the liner is a separate component from the catheter 212 and is disposed between an outer surface of the drive element 204 and an inner surface of the catheter 212.

In some embodiments, the tissue clipping assembly 102 includes a collar 120 operably coupled with the distal end of the catheter 212. The collar 120 may be a substantially tubular ring through which distal arm 104 and the drive element 204 may be extended and retracted. In some embodiments, the proximal arm 110 is coupled to the distal end of the collar 120. The proximal arm 110 and the collar 120 may be combined into a single component. In some embodiments, the collar 120 may be operably decoupled from the catheter 212, such as after the tissue clipping assembly 102 has clipped tissue such that the tissue clipping assembly 102 may continue to clip the tissue closed.

The tissue clipping device 100 may be used with any suitable or conventional endoscopic or laparoscopic surgical equipment. For purposes of this disclosure, the tissue clipping device 100 is described in the context of use with an endoscope, such as a colonoscope, gastroscope, duodenoscope, enteroscope, or sigmoidoscope type apparatus of conventional or suitable construction. However, the tissue clipping device 100 may also be used in other manners, such as in any minimally invasive procedure with a suitable natural or artificially created orifice in the body. The scope is provided with an elongated body having a controllably flexible projecting end region. Surgical instruments, such as the device 100, may be introduced through an instrument channel, such as an accessory channel, which extends through the scope body, for recruiting tissue targeted by the surgeon manipulating the scope. The tissue clipping assembly 102 may be sized, shaped, and configured such that it may be disposed through a single instrument or accessory channel of the endoscope.

The tissue clipping assembly 102 may be operated by a user at a proximal end of the endoscope via one or more drive elements 204 extending through a channel located within and extending through the endoscope, such as via the drive assembly 200. However, the device 100 may also be used without an endoscope, such as in minimally invasive procedure with a suitable natural or artificially created orifice in the body. The tissue clipping device 100 is constructed and configured such that it may also be inserted into a subject through an orifice or small incision and operated to clip tissue, such as to a tissue defect.

Figure 2A:
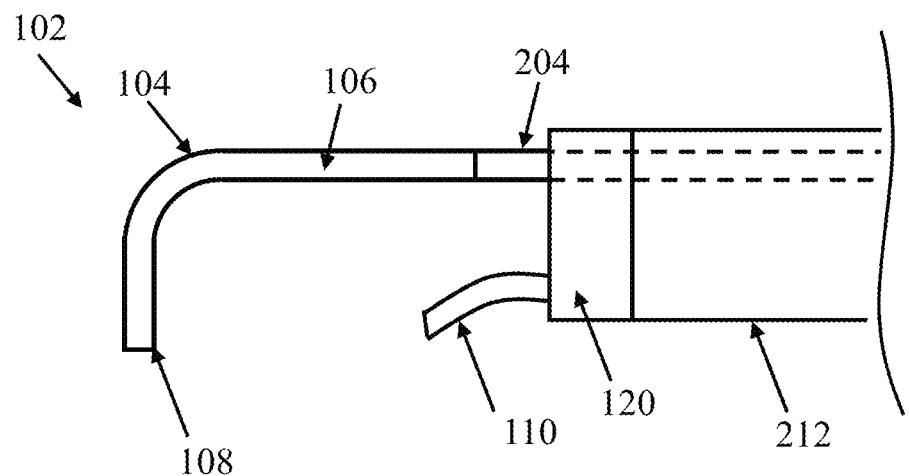
FIGS. 2A and 2B are schematic illustrations depicting the operation of the tissue clipping assembly according to one embodiment.
Figure 2B:
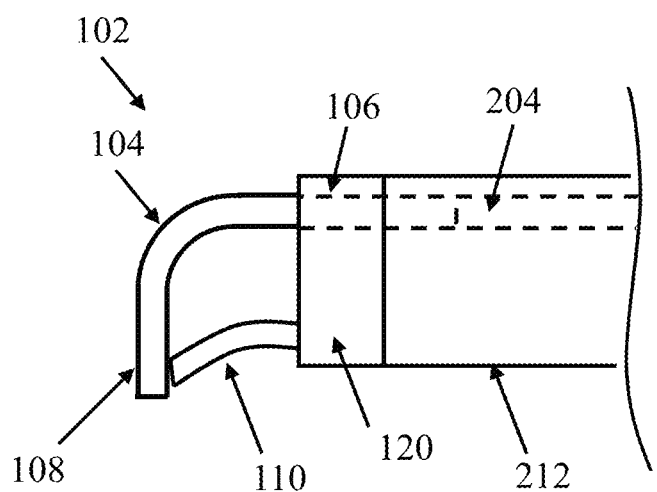

As shown in FIGS. 2A-2B, the distal arm 104 may be actuated by one of the drive elements 204 to extend from and retract into the catheter 212, such as to clip tissue. The drive element 204 coupled with the distal arm 104, such as the proximal end of the extending portion 106 of the distal arm 104, may be distally extended, such as via the handle 202, to distally extend the distal arm 104. In some embodiments, the distal arm 104 and the proximal arm 110 comprise wire, such as a flat wire.

The distal arm 104 may be linearly extended such that the grasping portion 108 of the distal arm 104 is spaced apart from the proximal arm 110, the collar 120, and the catheter 212. The tissue clipping assembly 102 may be in an extended or open position when the distal arm 104 is spaced apart from the proximal arm 110 (FIG. 2A). In some embodiments, the distal arm 104 may be distally extended from the catheter 212 between about 1 cm and about 3 cm. In some embodiments, the drive element 204 may also be rotated, such as via the handle 202, to rotate the distal arm 104, such as to position the grasping portion 108 of the distal arm 104 to clip target tissue.

When the tissue clipping assembly 102 is in the open position, the distal and proximal arms 104, 110 may be properly positioned relative to the target tissue. The grasping portion 108 of the distal arm 104 may be extended and placed such that it is disposed on a first side of a defect. The proximal arm 110 may be placed on a second side of the defect substantially opposite the first side. In some embodiments, the grasping portion 108 of the distal arm 104 is at least partially inserted into tissue on the first side of the defect and the proximal arm 110 is at least partially inserted into tissue on the second side of the defect such that the distal and proximal arms 104, 110 are each secured in the tissue. In some embodiments, the grasping portion 108 of the distal arm 104 and/or the proximal arm 110 include barbs, tines, or other projections configured to further secure the tissue to the grasping portion 108 of the distal arm 104 and/or the proximal arm 110.

The drive element 204 may also be retracted, such as via the handle 202, to retract the distal arm 104 toward the proximal arm 110, the collar 120, and/or the distal end of the catheter 212. As shown in FIG. 2B, the distal arm 104 may be retracted such that the tissue clipping assembly 102 is in a closed or clipping position in which the grasping portion 108 of the distal arm 104 substantially contacts or abuts the distal end of the proximal arm 110, such as to clip tissue. The retraction of the distal arm 104 toward the proximal arm 110 may pull the secured tissue from the first side of the defect to the secured tissue on the second side of the defect, such as to close the defect. In some embodiments, the distal and/or proximal arms 104, 110 may be locked in the closed position, as described below. In some embodiments, the distal and proximal arms 104, 110 may be decoupled from the drive assembly 200 when the tissue clipping assembly 102 is in the closed position, such as to keep the defect closed. In other embodiments, a hemostatic closure device may be deployed around the clipped tissue to apply a circumferential force around the tissue to maintain the closure of the tissue.

Figure 3A:
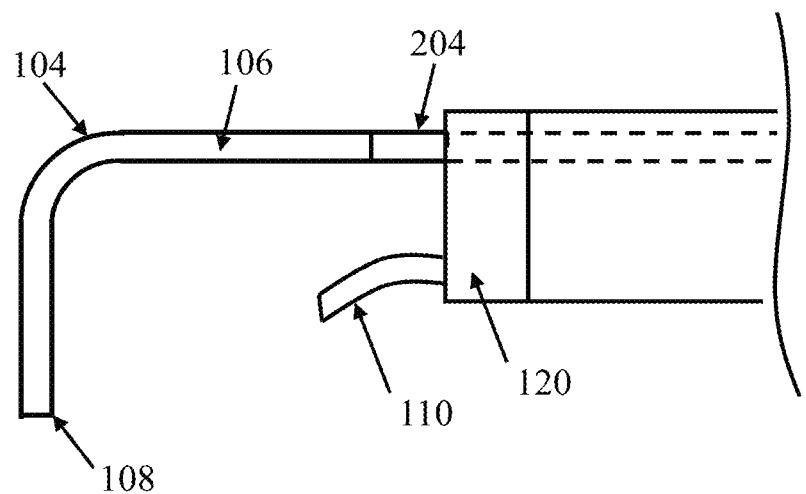
FIG. 3A is a schematic illustration of a tissue clipping assembly for use with a tissue clipping device according to one embodiment.
Figure 3B:
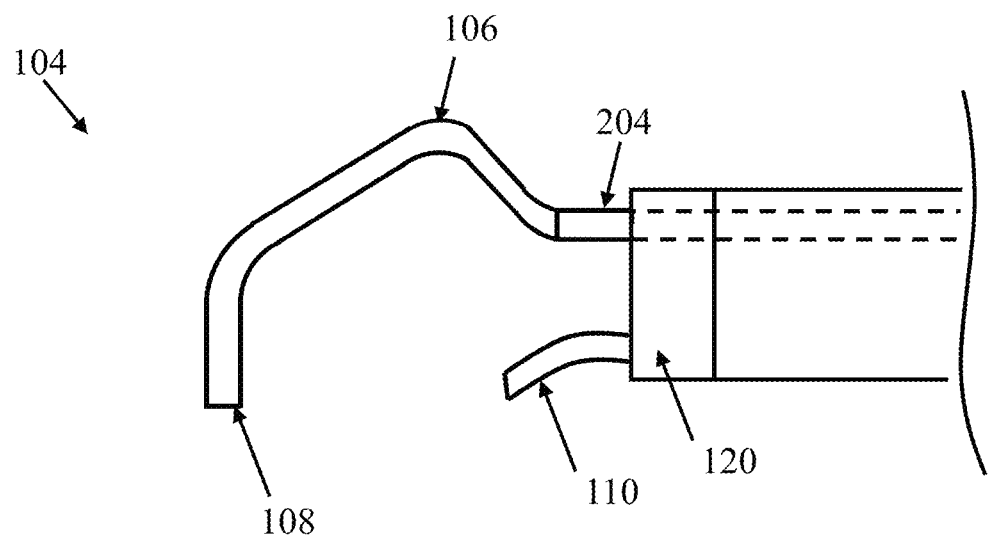
FIG. 3B is a schematic illustration of a tissue clipping assembly for use with a tissue clipping device according to one embodiment.
Figure 3C:
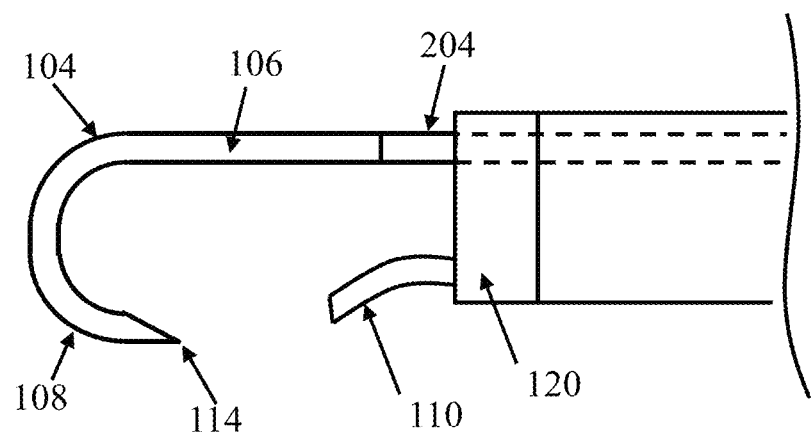
FIG. 3C is a schematic illustration of a tissue clipping assembly for use with a tissue clipping device according to one embodiment.

Referring to FIGS. 3A-3C, the distal arm 104 may have a variety of configurations, such as to increase the ability of the distal arm 104 to clip or otherwise grasp tissue. As shown in FIG. 3A, the grasping portion 108 of the distal arm 104 may be radially elongated (e.g., extend farther downwardly). The grasping portion 108 of the distal arm 104 may have a length such that the grasping portion 108 extends below the catheter 212 and/or the proximal arm 110. The distal arm 104 may comprise a flexible, superelastic, and/or shape memory material, such as stainless steel or Nitinol, such that the grasping portion 108 may be bent or flexed toward the extending portion 106 when the distal arm 104 is extended through the catheter 212 and such that the distal arm 104 may regain its shape when the grasping portion 108 is extended through the distal end of the catheter 212.

As shown in FIG. 3B, the extending portion 106 of the distal arm 104 may be bent or otherwise flexed upwardly. The upward extension of the extending portion 106 may provide additional space to grasp tissue, such as when the distal and proximal arms 104, 110 are positioned on opposite sides of a defect. The distal arm 104 may comprise a flexible or shape memory material, such as Nitinol, such that the extending portion 106 may be bent or flexed downwardly when the distal arm 104 is extended through the catheter 212 and such that the extending portion 106 may regain its shape when the extending portion 106 is extended through the distal end of the catheter 212.

As shown in FIG. 3C, the grasping portion 108 of the distal arm 104 may be curved or bent proximally toward the proximal arm 110. The orientation of the grasping portion 108 toward the proximal arm 110 may increase the ability of the distal arm 104 to grasp tissue, such as tissue on a first side of a defect, as described below. In some embodiments, the end of the grasping portion 108 may be pointed to increase the ability of the grasping portion 108 of the distal arm 104 to pierce and/or grasp tissue during the clipping operation.

Figure 4A:
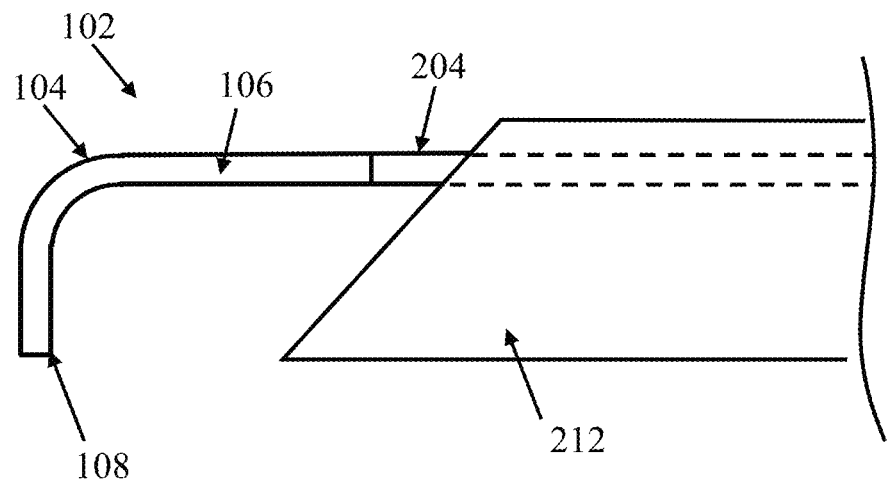
FIG. 4A is a schematic illustration of the distal end of a tissue clipping device according to one embodiment.
Figure 4B:
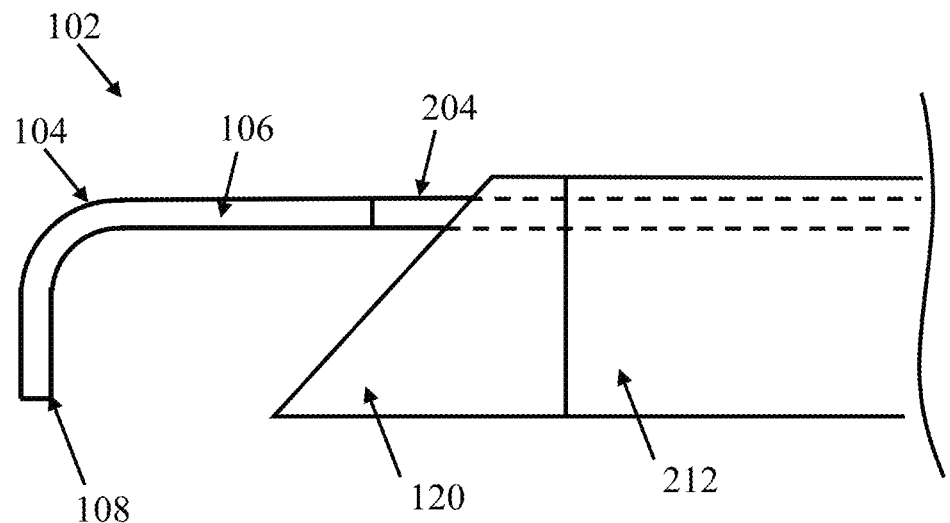
FIG. 4B is a schematic illustration of the distal end of a tissue clipping device according to another embodiment.

While the distal arm 104 has been described as being retractable to clip tissue against the proximal arm 110, it will be understood that the device 100 may have other configurations and assemblies. For example, as shown in FIGS. 4A and 4B, the distal end of the catheter 212 (FIG. 4A) or the distal end of the collar 120 (FIG. 4B) may be angled such that the bottom of the catheter 212 or the collar 120 protrudes distally. The catheter 212 or the collar 120 may be angled such that the bottom of the distal end extends about 3 cm from the top of the distal end.

The distal protrusion of the catheter 212 or the collar 120 may operate substantially similarly to the proximal arm 110 described in FIGS. 1-3B. For example, the distal arm 104 may be extended, such as via the drive element 204, and secured in tissue on a first side of a defect and the protrusion of the catheter 212 or collar 120 may be secured in tissue on the second side of the defect. The distal arm 104 may then be retracted, such as via the drive element 204, toward the protrusion of the catheter 212 or collar 120 such that the secured tissue from the first side of the defect is brought toward the secured tissue on the second side of the defect, such as to close the defect. In embodiments where the distal end of the collar 120 is angled to secure tissue on one side of the defect, the distal arm 104 and the collar 120 may be secured together and decoupled from the drive assembly 200, such as to keep the defect closed.

Figure 5A:
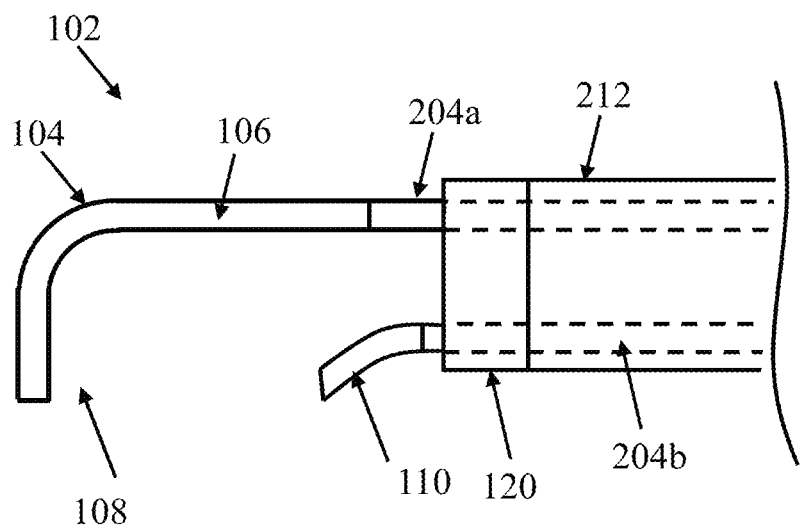
FIGS. 5A and 5B are schematic illustrations depicting the operation of the tissue clipping assembly according to another embodiment.
Figure 5B:
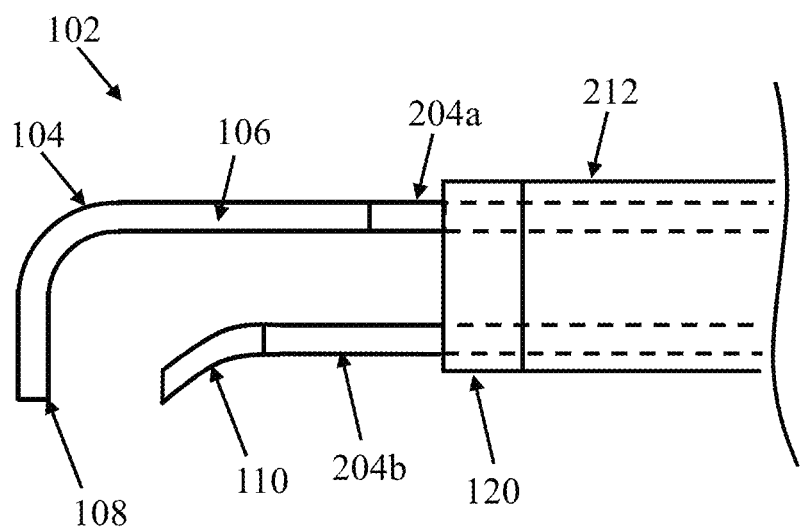

In some embodiments, the proximal arm 110 may be extendable and retractable similarly to the distal arm 104. As shown in FIGS. 5A and 5B, the proximal end of the distal arm 104, such as the proximal end of the extending portion 106, is coupled with a first drive element 204a and the proximal end of the proximal arm 110 is coupled with a second drive element 204b. The proximal arm 110 may be linearly translated and rotated via the second drive element 204b, such as via a second control actuator 210 of the handle 202, to position the proximal arm 110 and clip tissue. For example, the distal arm 104 may be translated and/or rotated to secure tissue on a first side of a defect and the proximal arm 110 may be translated and/or rotated to secure tissue on a second side of the defect. The distal arm 104 may then be retracted toward the catheter 212 and/or the proximal arm 110 may be extended from the catheter 212 to close the defect. In some embodiments, the distal arm 104 and the proximal arm 110 rotate together via the same drive element 204. In other embodiments, the proximal arm 110 opens via extension of the distal arm 104. In some embodiments, the distal arm 104 and the proximal arm 110 may be operated such that the distance between the distal end of the proximal arm 110 and the grasping portion 108 of the distal arm 104 is between about 0.5 cm and about 3 cm.

The proximal arm 110 of any of the other tissue clipping devices 100 may be actuatable by a drive element 204. For example, the proximal arm 110 of FIGS. 1-3B may be actuatable by a drive element 204. In embodiments with two drive elements 204, the catheter 212 may include two lumens with one drive element 204 disposed through each lumen. In embodiments with one drive element 204, the catheter 212 may include a single lumen through which the tissue clipping assembly 102 is extended.

Referring to FIGS. 6A-6D, the tissue clipping assembly 102 may be maneuvered, such as via the drive assembly 200, to grasp tissue in two locations, such as on opposite sides of a defect, and clip the tissue together. The tissue clipping assembly 102 may be decoupled from the drive assembly 200 to maintain the closure of the tissue via the tissue clipping assembly 102. The tissue clipping assembly 102 may be moved to a locked position before the tissue clipping assembly 102 is decoupled from the drive assembly 200.

Figure 6A:
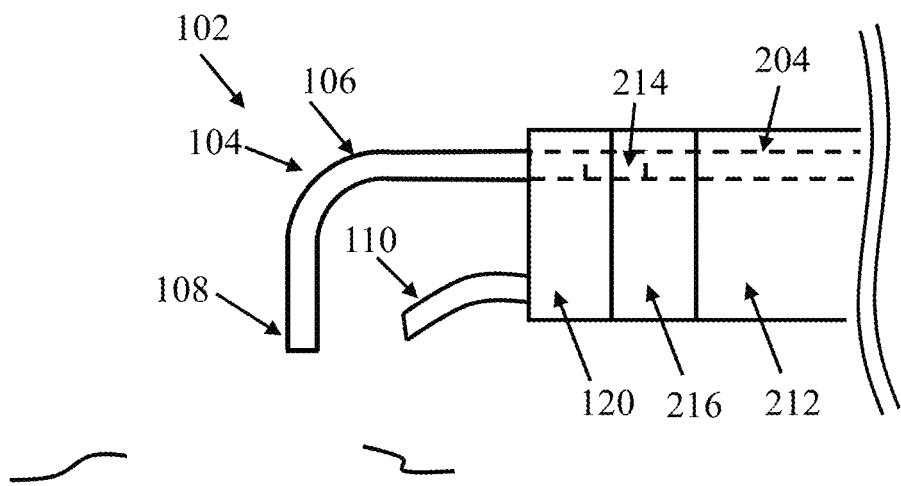
FIGS. 6A through 6D are schematic illustrations showing a tissue clipping operation with a tissue clipping device.

As shown in FIG. 6A, the tissue clipping assembly 102 may be oriented substantially above target tissue, such as an identified defect. For example, the endoscope and/or the catheter 212 may be manipulated such that the tissue clipping assembly 102 is in the desired position substantially above the tissue. The grasping portion 108 of the distal arm 104 may be positioned near the distal end of the catheter 212. The drive assembly 200 may include a coupler 214 which operably couples the distal end of the drive element 204 to the proximal end of the extending portion 106 of the distal arm 104. The drive assembly 200 may also include a connector 216 which operably couples the distal end of the catheter 212 to the proximal end of the collar 120. The connector 216 may be fixed to the distal end of the catheter 212 or may be included as a component of the catheter 212.

Figure 6B:
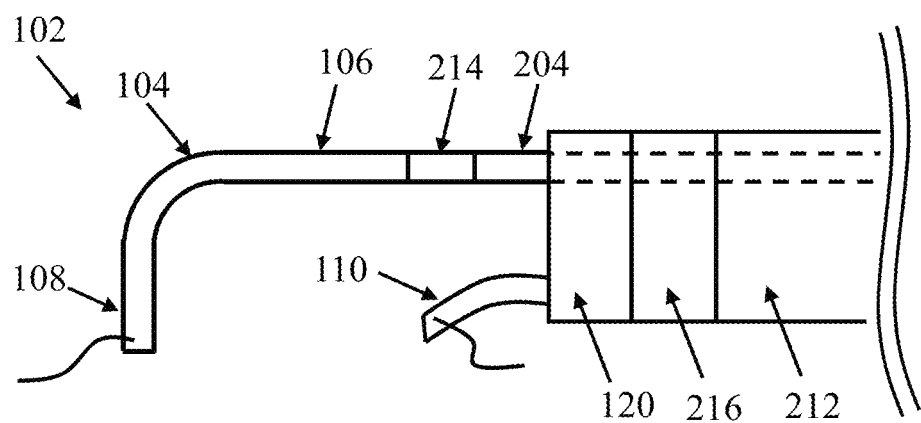

As shown in FIG. 6B, the distal arm 104 may be extended, such as via the drive element 204, such that the grasping portion 108 of the distal arm 104 secures tissue at a first location, such as on a first side of the defect. The coupler 214 may be configured to transmit the translational and rotational movement of the drive element 204 to the distal arm 104 such that the distal arm 104 may be properly positioned. The proximal arm 110 may be maneuvered, such as via the catheter 212 and/or the endoscope such that the proximal arm 110 secures tissue at a second location, such as on a second side of the defect.

Figure 6C:
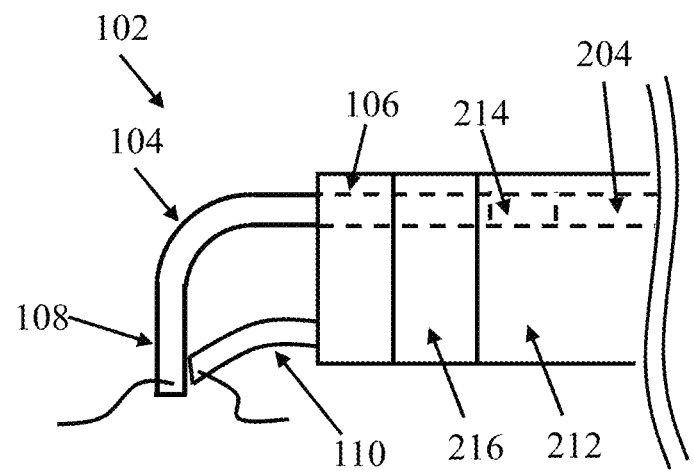

As shown in FIG. 6C, the tissue clipping assembly 102 may appose the tissue from the two locations, such as to close the defect. The distal arm 104 may be retracted, such as via the drive element 204, to the closed position such that the tissue from the first location is brought toward the tissue at the second location. The position and rotation of the distal arm 104 may be locked or otherwise maintained in the closed position such that the tissue remains clipped. For example, the collar 120 may provide a frictional, interference, or compressive force against the distal arm 104 which maintains the distal arm 104 in the closed position.

Figure 6D:
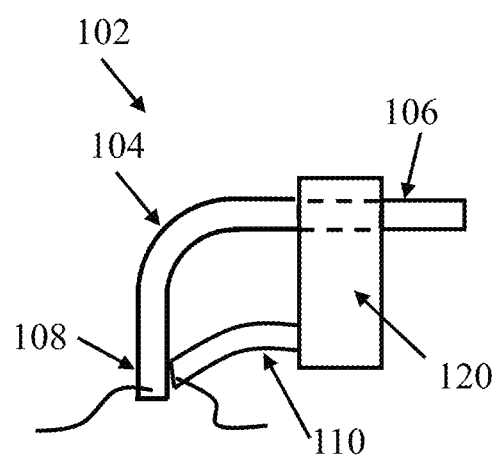

As shown in FIG. 6D, the tissue clipping assembly 102 may be decoupled from the drive assembly 200. The distal arm 104 may be decoupled from the drive element 204 and the collar 120 may be decoupled from the catheter 212. The coupler 214 may decouple the drive element 204 from the distal arm 104 such that the drive element 204 and coupler 214 may be retracted from the distal arm 104. The connector 216 may decouple the collar 120 from the catheter 212 such that the catheter 212 may be retracted from the collar 120, as described below. The drive assembly 200 may be withdrawn from the body and the tissue clipping assembly 102 may remain in position to continue to clip the tissue. Optionally, the drive assembly 200 of the device 100 may be loaded with a second tissue clipping assembly 102 such that the second tissue clipping assembly 102 may be deployed to clip tissue at a different location, such as to close a larger defect.

Figure 7:
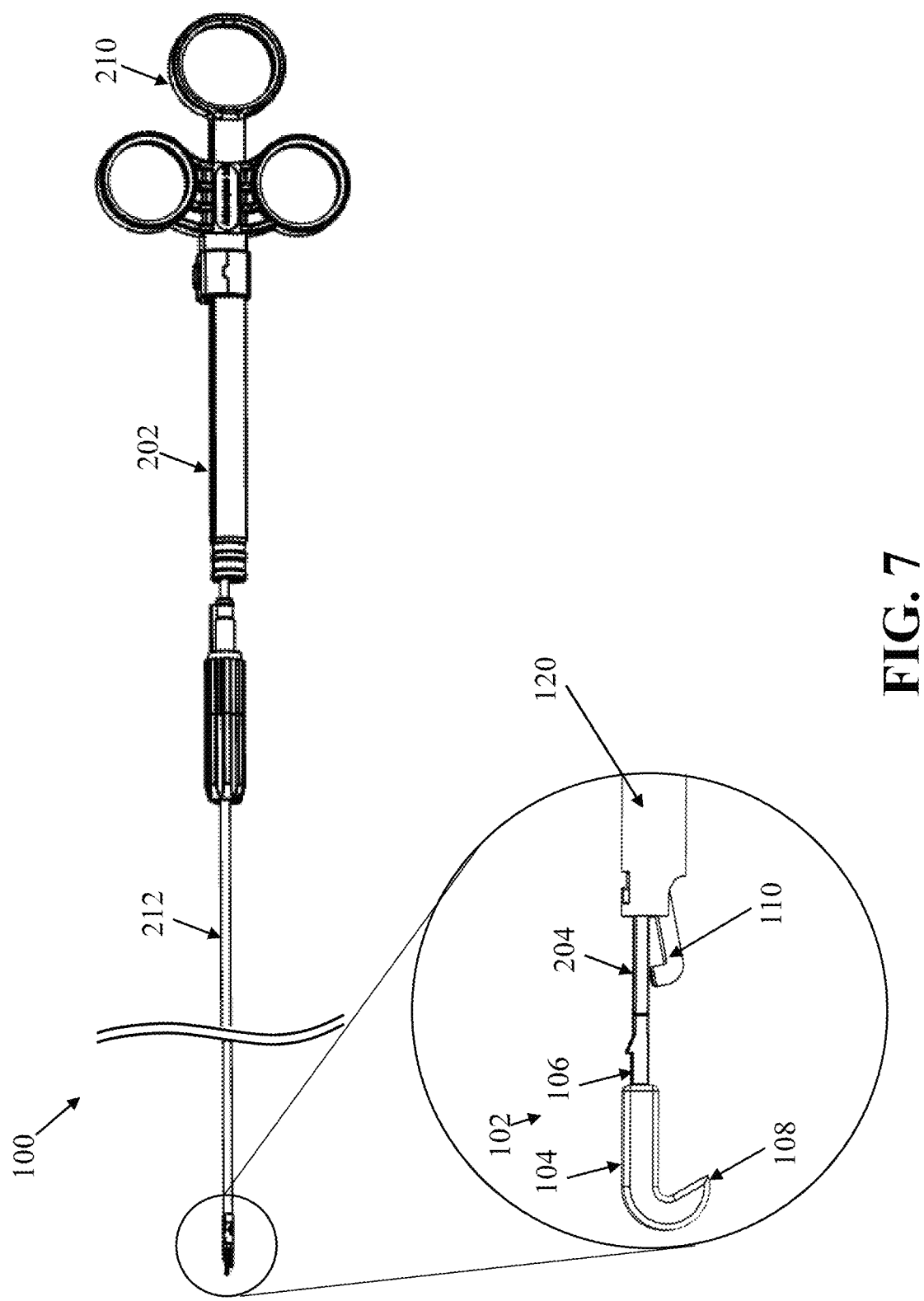
FIG. 7 is a side view of a tissue clipping device according to one embodiment.

Referring now to FIGS. 7, a tissue clipping device 100 is shown according to one embodiment. The handle 202 includes the control actuator 210 which is operable to control the movement of the distal arm 104 via the drive element 204. The distal arm 104 may be extended from and retracted into the collar 120, such as to clip tissue against the proximal arm 110 of the tissue clipping assembly 102. The collar 120 may be coupled with the distal end of the catheter 212. In some embodiments, the collar 120 is releasably coupled with the catheter 212, such as described below.

A user may grasp the handle 202 and manipulate the control actuator 210 to maneuver the distal arm 104 via the drive element 204. The distal arm 104 may be extended from the collar 120 across target tissue. The proximal arm 110 may be positioned to grasp tissue at a first side of the target tissue and the distal arm 104 may be positioned to grasp tissue at a second side of the tissue, such as opposite the first side. The distal arm 104 may be retracted to the closed position to clip tissue between the distal arm 104 and the proximal arm 110. In some embodiments, the distal arm 104 may be retracted to recruit tissue into the collar 120 when the tissue clipping assembly 102 clips tissue. In some embodiments, the collar 120 may be decoupled from the catheter 212 such that the tissue clipping assembly 102 continues to clip the tissue after the drive assembly 200 is withdrawn from the body.

In the illustrated embodiment, the handle 202 includes one control actuator 210 coupled to the distal arm 104 via the drive element 204. However, it will be understood that the device 100 may have other configurations and assemblies. For example, the handle 202 may include a second control actuator 210 coupled to a second drive element 204 to operable control the position of the proximal arm 110.

The proximal arm 110 and/or the distal arm 104 may be sized, shaped, and configured to more securely grasp tissue, such as to better grasp tissue as the tissue clipping assembly 102 is moved to the closed position and/or to more securely retain the distal and proximal arms 104, 110 in the tissue when the tissue clipping assembly 102 clips tissue, such as when then tissue clipping assembly 102 clips sides of a defect together.

Figure 8A:
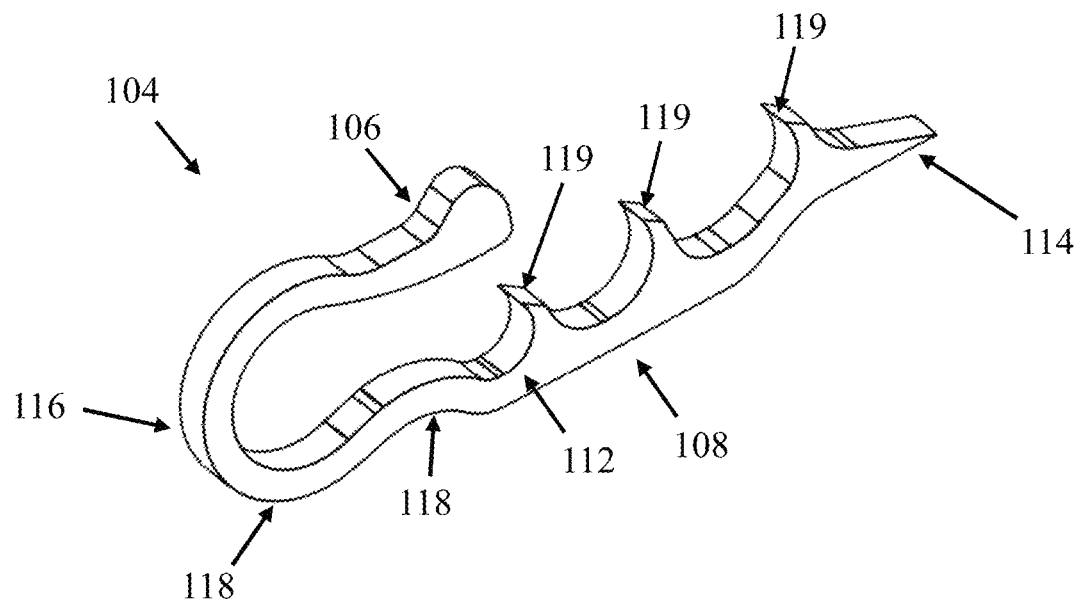
FIG. 8A is a perspective view of a distal arm according to one embodiment.
Figure 8B:
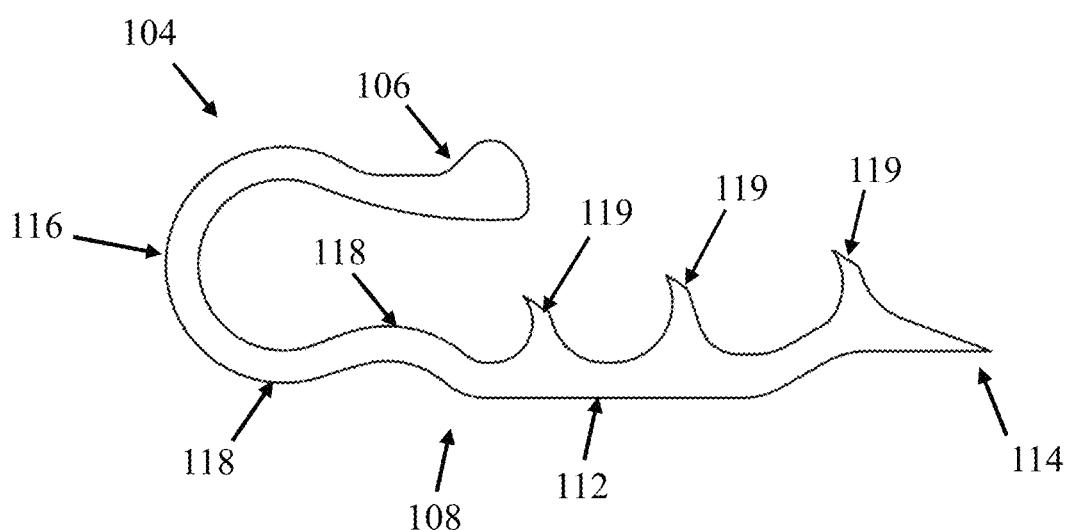
FIG. 8B is a side view of the distal arm of FIG. 8A.

In some embodiments, as shown in FIGS. 8A and 8B, the distal arm 104 is configured to increase the grasp and securement of the distal arm 104 on tissue. The grasping portion 108 of the distal arm 104 includes one or more distal tines 112 configured to increase the grasp of the distal arm 104 on target tissue. The distal tines 112 may extend substantially proximally toward the proximal arm 110, such as to grasp and recruit tissue as the distal arm 104 is proximally retracted during the tissue clipping operation. Each distal tine 112 may include a tip 114 at the proximal end that is operable to pierce tissue. The tip 114 may be sized, shaped, and configured to drive the distal tine 112 into tissue. The distal tine(s) 112 may be integral with the distal arm 104 or may be an additional component attached to the distal arm 104. In some embodiments, the distal tines 112 comprise stainless steel, Nitinol, ceramic, polymer, or other suitable composite material, or any combination thereof. In some embodiments, the grasping portion 108 of the distal arm 104 has a length between about 1 mm and about 7 mm, such as between about 3 mm and about 6 mm, such as about 5 mm.

In some embodiments, at least a portion of the distal arm 104, such as the distal tine(s) 112, is flexible such that the distal arm 104 may flex when the distal arm 104 is maneuvered to grasp tissue. The distal arm 104 may be flexible such to allow the distal tine(s) 112 to be placed against tissue during the tissue clipping operation. For example, the distal arm 104 may be flexible such that the distal tines 112 may be oriented downwardly toward the target tissue, such as at an angle, such that the distal arm 104 may grasp tissue at the second side of the target tissue. The distal arm 104 may also be stiff enough such that the distal arm 104 may retain the grasped tissue, such as during the tissue clipping operation, and to clip tissue against the proximal arm 110.

In some embodiments, the distal end of the one or more distal tines 112 may be sized, shaped, or configured to reduce trauma to tissue as the distal arm 104 is extended from the catheter 212 and/or to prevent damage to the catheter 212 and/or the endoscope, such as when extending the tissue clipping assembly 102 through the catheter 212 and/or endoscope. For example, the distal end of the distal tines 112 may each include a rounded portion 116 configured to deflect tissue and reduce damage to the catheter 212 and/or the endoscope when the tissue clipping assembly 102 is extended through the catheter 212 and/or the endoscope. In some embodiments, the rounded portions 116 of the distal tines 112 also extend beneath the tip 114, such as to lift the distal tines 112 in relation to the surface of the tissue when the distal arm 104 is retracted from the clipped tissue. The rounded portions 116 may also shroud the proximal arm 110 when the distal arm 104 is disposed near the proximal arm 110 such as to protect the proximal arm 110 when the tissue clipping assembly 102 is extended through the catheter 212 and/or endoscope and to protect users from the proximal arm 110 during handling. The rounded portions 116 may be configured such that the tissue clipping assembly 102 is atraumatic when the distal arm 104 is disposed near the proximal arm 110, such as when the tissue clipping assembly 102 is in the closed position, such as to protect the operator, the endoscope, the catheter 212, and/or the patient.

The distal tines 112 may also include one or more bends 118 along a length of the distal tine 112. The bends 118 may be configured such that the tip 114 of the distal tine 112 is inserted into tissue when the distal arm 104 is retracted during the tissue clipping operation. The bends 118 may also be configured such that the tip 114 and the distal tine 112 are driven away from live tissue as the distal arm 104 is proximally retracted during the tissue clipping operation. The bends 118 may further be sized, shaped, and configured to increase the flexibility of the distal arm 104 as the distal arm 104 grasps tissue and to strengthen the distal arm 104 when the distal arm 104 grasps and recruits tissue. For example, the bends 118 may be configured and arranged to prevent the distal tine 112 from pivoting radially outwardly about the rounded portion 116 during the tissue clipping operation. The bends 118 and/or the tip 114 of the distal tine 112 may also be sized, shaped, and configured to guide the distal tines 112 into tissue. For example, one or more sides of the distal tine 112 (e.g., top and/or bottom) may be chamfered or tapered toward the tip 114 such that the distal tine 112 is guided into tissue when the tip 114 is inserted into tissue and the distal arm 104 is proximally retracted (see FIG. 19D).

In the illustrated embodiment, the distal arm 104 is substantially linear. However, it will be understood that the distal arm 104 may have other suitable shapes and configurations. For example, the grasping portion 108 may include one or more radial bends 118 (e.g., left and right), such as to increase the ability of the distal arm 104 to be inserted into tissue and/or to increase the ability of the distal arm 104 to grasp tissue during the tissue clipping operation. Further, the distal arm 104 may include a hypotube with shorter tines on either side of the distal tine 112.

In some embodiments, the distal tines 112 are further configured to better grasp tissue. For example, one or more distal tines 112 may include one or more barbs 119. The barbs 119 may extend substantially laterally from one or both sides of the respective distal tine 112. The barbs 119 may be arranged and configured to assist with securing the distal tine(s) 112, such as within tissue during the clipping procedure. The barbs 119 may be sized, shaped, and configured to be inserted into tissue and to sufficiently prevent the distal tine 112 from being retracted from the tissue, such as after the tissue clipping assembly 102 has been deployed in the closed position.

In the illustrated embodiment, the barbs 119 extend from the top of the distal tine 112. However, it will be understood that the distal arm 104 may have other configurations and assemblies. For example, the distal arm 104 may also include barbs 119 extending downwardly from the distal tine(s) 112 and/or the distal arm 104 may include barbs 119 extending from one or more sides of the distal tine(s) 112.

Figure 9A:
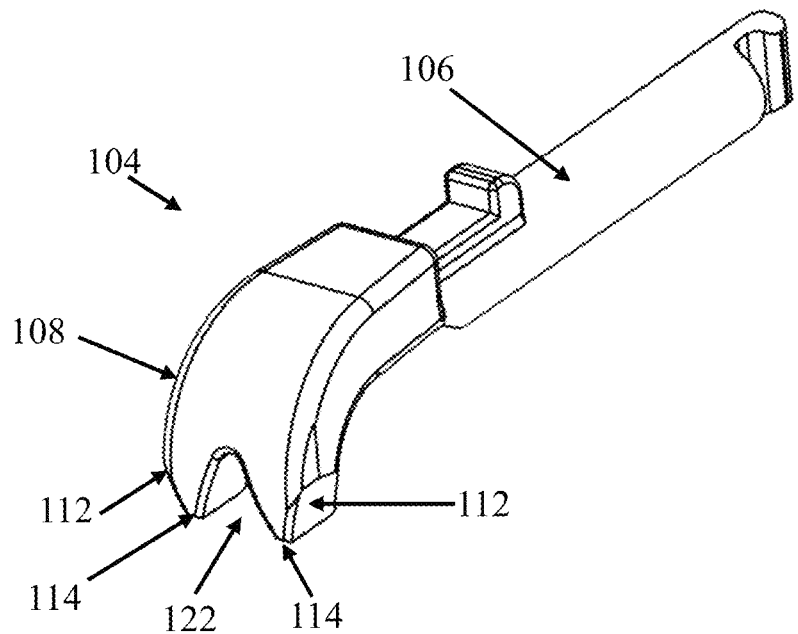
FIG. 9A is a perspective view of a distal arm according to another embodiment.
Figure 9B:
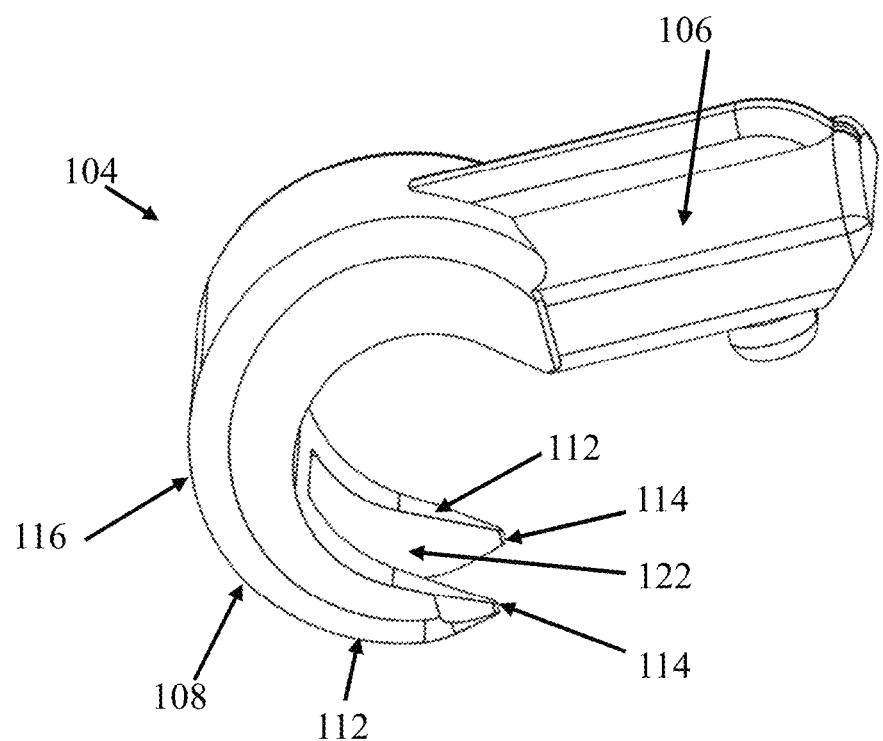
FIG. 9B is a perspective view of a distal arm according to another embodiment.
Figure 9C:
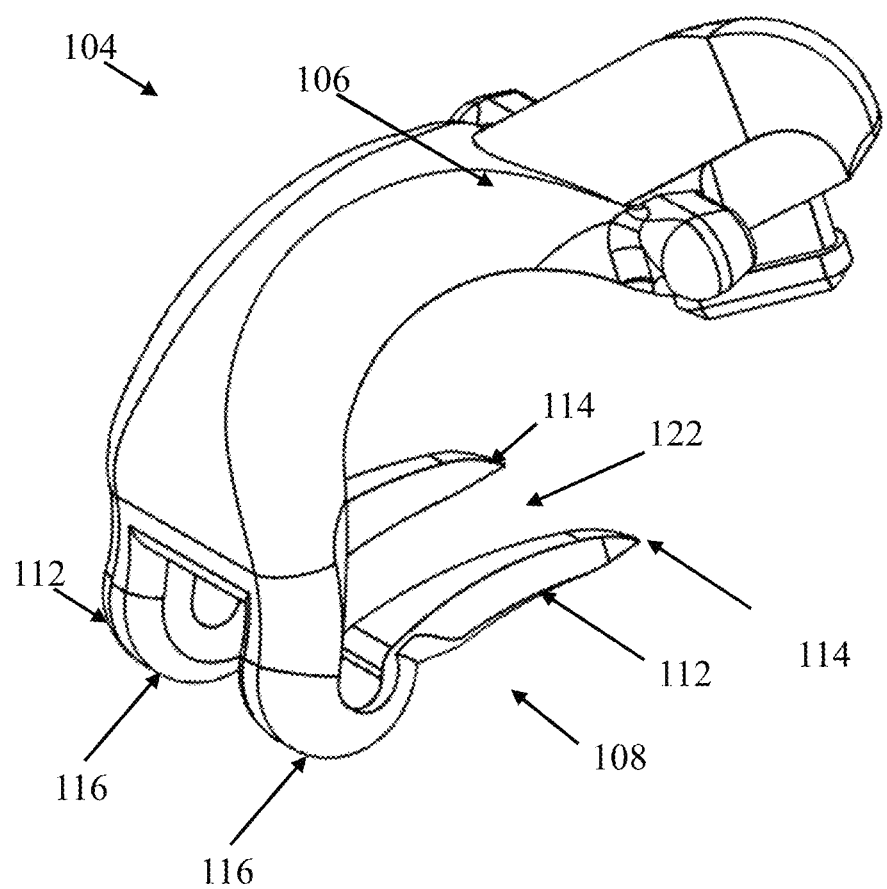
FIG. 9C is a perspective view of a distal arm according to another embodiment.

The distal arm 104 may include more than one distal tine 112 to grasp and recruit tissue during the tissue clipping operation. As shown in FIGS. 9A-9C, the distal arm 104 includes two distal tines 112, each having a tip 114. The distal tines 112 may have other shapes, sizes, and configurations than the distal tine 112 of FIGS. 8A and 8B, such as based upon the location of the target tissue to be clipped. For example, the distal tines 112 may be oriented substantially downwardly (FIG. 9A). The distal tines 112 may also be rounded and shorter such that the grasping portion 108 of the distal arm 104 forms a semi-circle (FIG. 9B).

The distal tines 112 may also include rounded portions 116 extending distally and downwardly from the remainder of the distal tine 112 (FIG. 9C) to reduce trauma to the tissue when the distal arm 104 is extended from the collar 120 and/or prevent damage to the catheter 212 and/or the endoscope such as when extending the tissue clipping assembly 102 through the catheter 212 and/or endoscope. The rounded portions 116 may also extend beneath the remainder of the distal tines 112, such as to lift the distal tines 112 in relation to the surface of the tissue when the distal arm 104 is retracted to clip tissue. The rounded portion(s) 116 may also shroud the proximal arm 110 when the distal arm 104 is disposed near the proximal arm 110 such as to protect the proximal arm 110 when the tissue clipping assembly 102 is extended through the catheter 212 and/or endoscope and to protect users from the proximal arm 110 during handling. The rounded portions 116 may be configured such that the tissue clipping assembly 102 is atraumatic when the distal arm 104 is disposed near the proximal arm 110, such as when the tissue clipping assembly 102 is in the closed position, such as to protect the operator, the endoscope, the catheter 212, and/or the patient. Further, the distal arm 104 may include more than two distal tines 112.

The distal tines 112 may be separated by a distal gap 122. The distal gap(s) 122 may separate the distal tines 112 such that each distal tine 112 may separately grasp tissue. The distal gap(s) 122 may also be sized, shaped, and configure to receive a portion of the proximal arm 110 when the tissue clipping assembly 102 is in the closed position such that the distal arm 104 and proximal arm 110 overlap in the closed position. For example, the tissue clipping assembly 102 may be maneuvered, such as via the drive assembly 200, to grasp tissue on opposite sides of target tissue with the distal and proximal arms 104, 110 and the proximal arm 110 may extend distally into the distal gap 122 when then tissue clipping assembly 102 is moved to the closed position.

Figure 10A:
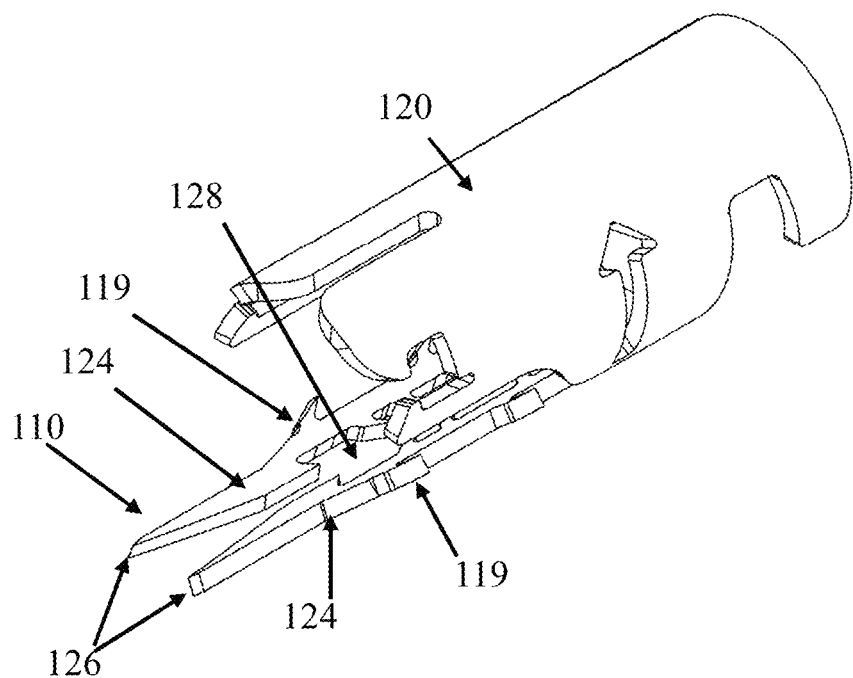
FIG. 10A is a perspective view of a collar with a proximal arm according to one embodiment.
Figure 10B:
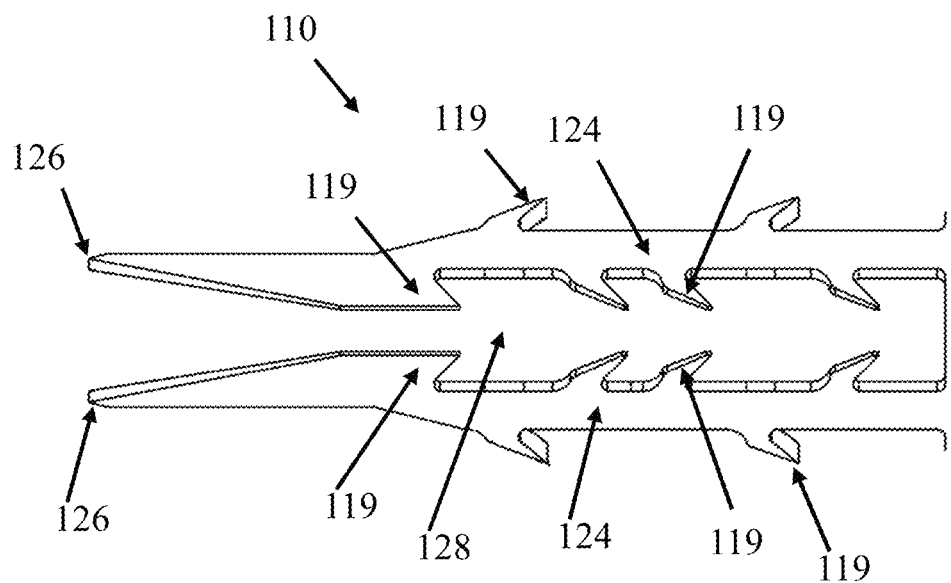
FIG. 10B is a bottom view of the proximal arm of FIG. 10A.
Figure 11A:
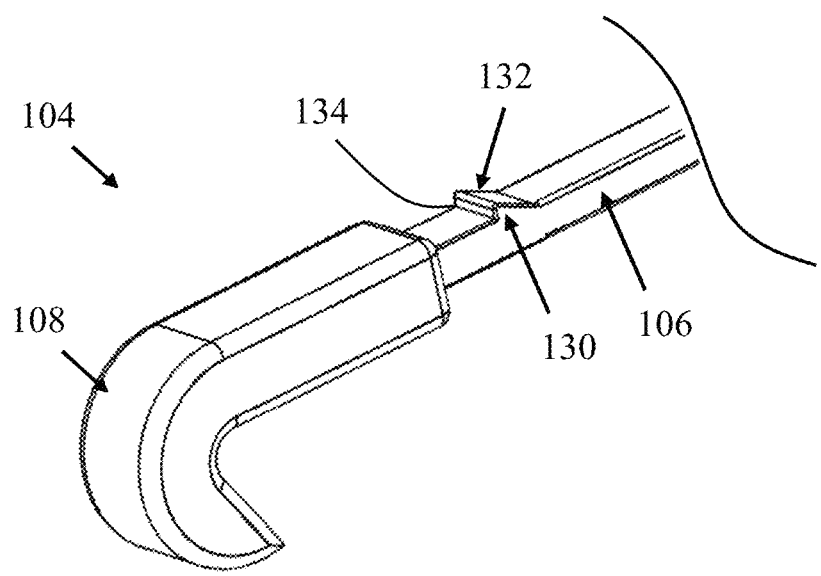
FIG. 11A is a perspective view of a distal arm according to one embodiment.
Figure 11B:
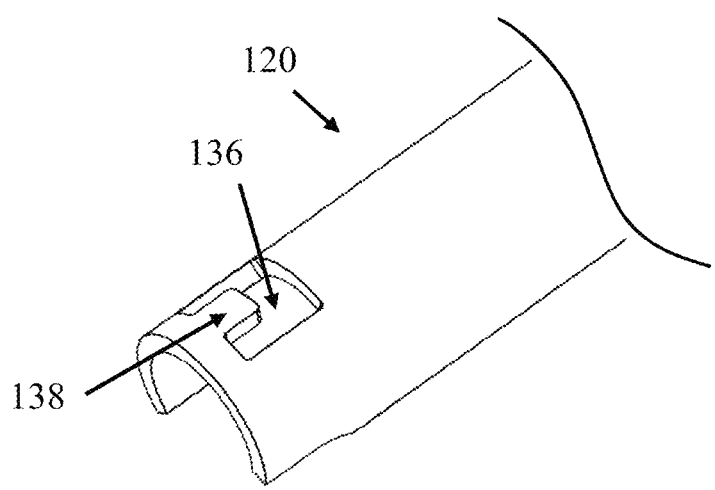
FIG. 11B is a perspective view of a collar according to one embodiment for use with the distal arm of FIG. 11A.
Figure 11C:
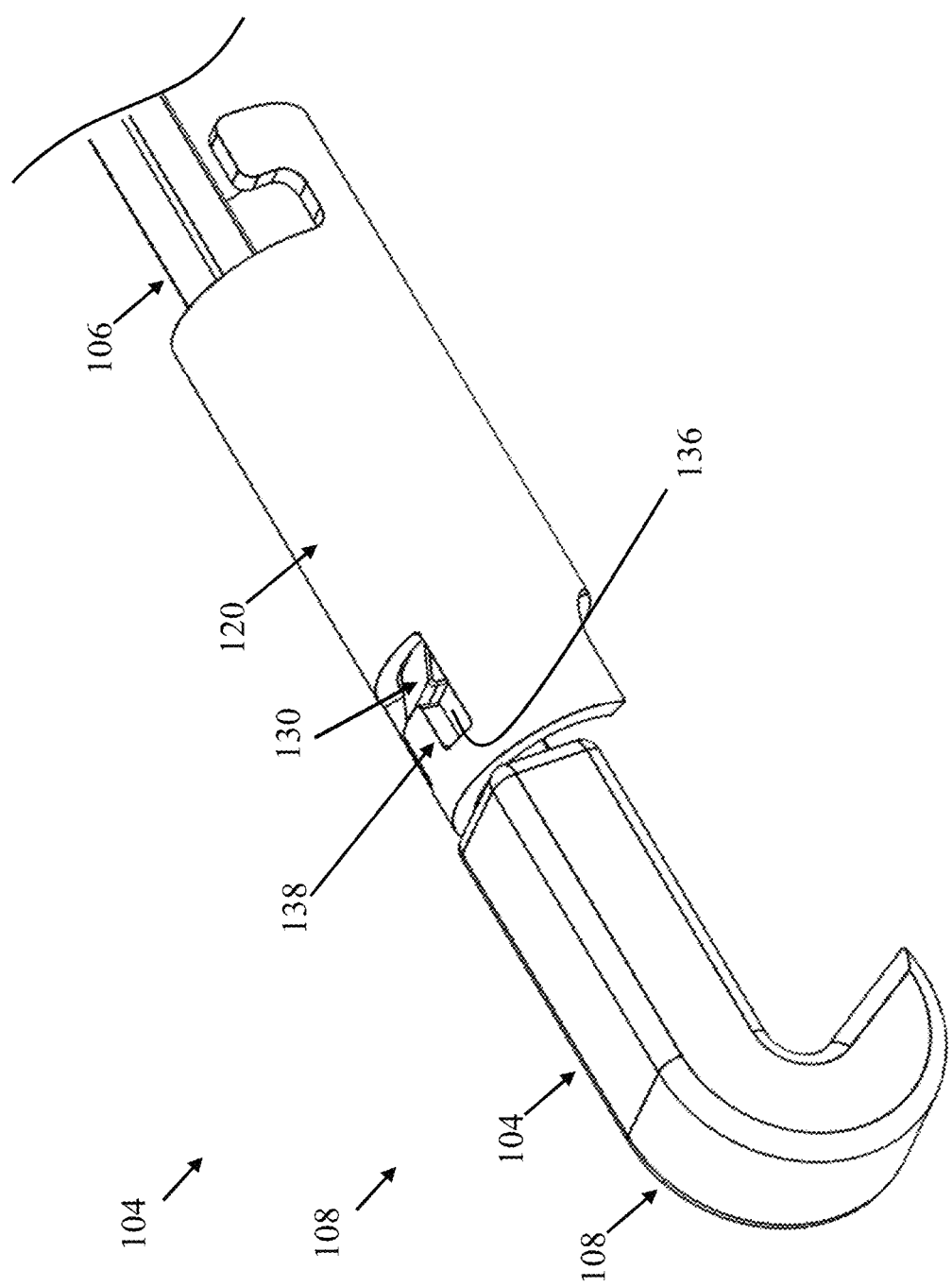
FIG. 11C is a perspective view of the distal arm of FIG. 11A in a locked position in the collar of FIG. 11B.

In some embodiments, as shown in FIGS. 10A and 10B, the proximal arm 110 includes one or more proximal tines 124 configured to increase the grasp of the proximal arm 110 on target tissue, such as on the first side of target tissue. The proximal tines 124 may be attached to or integrally formed with the proximal arm 110. The proximal tines 124 may extend distally from the collar 120 and may be operable to further increase the grasp of the proximal arm 110 on tissue. In embodiments in which the proximal arm 110 is integral with the collar 120, the proximal tines 124 may be integral with the collar 120. In some embodiments, the proximal tines 124 comprise stainless steel, Nitinol, ceramic, polymer, or composite material, or any combination thereof.

The proximal tines 124 may each include a tip 126 at a distal end of the proximal tine 124 that is operable to pierce tissue. The tips 126 of the proximal tines 124 may be inserted into tissue at a first side of target tissue to grasp tissue during the tissue clipping operation. In some embodiments, the proximal tines 124 may be substantially arcuate. For example, the proximal tines 124 may extend from the distal end of the collar 120 such that the upper surfaces of the proximal tines 124 substantially correspond to the shape of the inner surface of the collar 120.

In some embodiments, the proximal tines 124 are further configured to better grasp tissue. The more proximal tines 124 may also include one or more barbs 119. The barbs 119 may extend substantially laterally from one or more sides of the respective proximal tine 124 The barbs 119 may be arranged and configured to assist with securing the proximal tine(s) 124, such as within tissue during the clipping procedure. For example, the barbs 119 may be arranged and configured to be inserted into tissue and to prevent or otherwise restrict the proximal arm 110 from being retracted from the tissue.

In the illustrated embodiment, the proximal arm 110 includes two proximal tines 124. However, it will be understood that the proximal arm 110 may have other configurations and assemblies. For example, the proximal arm 110 may include one or three or more proximal tines 124.

In some embodiments, the proximal tines 124 of the proximal arm 110 define one or more proximal gaps 128 between the proximal tines 124. The proximal gaps 128 may increase the ability of the proximal arm 110 to grasp tissue. For example, the proximal gaps 128 between the proximal tines 124 may allow each proximal tine 124 to separately grasp tissue. The proximal gaps 128 may also be sized, shaped, and configure to receive a portion of the distal arm 104, such as the distal tines 112, when the tissue clipping assembly 102 is in the closed position. For example, the tissue clipping assembly 102 may be maneuvered, such as via the drive assembly 200, to grasp tissue on opposite sides of target tissue with the distal and proximal arms 104, 110 and the distal tines 112 may extend into the proximal gaps 128 when then tissue clipping assembly 102 is moved to the closed position. In some embodiments, the proximal tines 124 are shaped and configured such that the proximal gaps 128 are narrower near the distal end of the proximal arm 110 to increase the ability of the proximal arm 110 to be inserted into tissue, such as to allow the proximal tines 124 to be inserted into tissue substantially simultaneously. The distal tines 112 may also be configured such that the distal gaps 122 are narrower near the proximal end of distal arm 104 to increase the ability of the distal arm 104 to be inserted into tissue, such as to allow the distal tines 112 to be inserted into tissue substantially simultaneously. In other embodiments, the proximal gaps 128 are wider near the distal end of the proximal arm 110 and/or the distal gaps 122 are wider near the proximal end of the distal arm 104, such as to allow each proximal tine 124 and/or distal tine 112 to separately grasp tissue.

While the proximal gaps 128 have been described as being formed between the proximal tines 124, it will be understood that the proximal arm 110 may include additional proximal gaps 128 and/or the proximal gaps 128 may be formed in other manners. For example, the proximal arm 110 may include one or more proximal gaps 128 extending along the proximal arm 110, such as within the proximal tines 124. Further, the collar 120 may also be configured to include one or more proximal gaps 128 such as extending into the collar 120.

In some embodiments, at least a portion of the proximal arm 110, such as portions of the proximal tines 124, may be flexible such that the proximal arm 110 may flex when the proximal arm 110 is maneuvered to grasp tissue. The proximal arm 110 may be flexible such to allow the proximal tine(s) 124 to be placed against tissue during the tissue clipping operation. For example, the proximal arm 110 may be flexible such that the proximal tines 124 may be oriented downwardly toward the target tissue, such as at an angle, such that the proximal arm 110 may grasp tissue at the first side of the target tissue and such that the distal arm 104 may be maneuvered to grasp tissue at the second side of the target tissue. The proximal arm 110 may also be stiff enough such that the proximal arm 110 may retain the grasped tissue, such as during the tissue clipping operation, and clip tissue against the distal arm 104.

Referring now to FIGS. 11A-13, the tissue clipping device 100 is configured such that the collar 120 is operable to lock the position of the distal arm 104 when the distal arm 104 is fully retracted toward the catheter 212, such as when the distal arm 104 is moved to the closed position. The collar 120 may maintain the position of the distal arm 104 when the distal arm 104 is in the locked position, such as to allow the distal arm 104 to continue to clip tissue against the proximal arm 110. In some embodiments, after the position of the distal arm 104 has been retracted to the locked position and secured relative to the collar 120, the distal arm 104 may be decoupled from the drive element 204. In some embodiments, the force required to lock the distal arm 104 with the collar 120 is between about 0.1 pounds and about 6 pounds, such as between about 2 pounds and about 4 pounds. In some embodiments, the force required to lock the distal arm 104 with the collar is about 2 pounds or greater, such as to prevent unintentional locking of the distal arm 104.

In some embodiments, as shown in FIGS. 11A-13, the extending portion 106 of the distal arm 104 includes one or more locking projections 130 extending outwardly from the outer surface of the extending portion 106. The locking projection 130 may be sized, shaped, and configured to couple the distal arm 104 with the collar 120 when the distal arm 104 is moved to the locked position, such as when the tissue clipping assembly 102 is moved to the closed position. The locking projection 130 may be positioned and configured, such as being spaced apart from the distal end of the distal arm 104 and/or extending to a distance from the outer surface of the distal arm 104, such as to prevent scratching or otherwise injuring tissue during the tissue clipping operation. In some embodiments, the locking projection 130 is initially bent radially inwardly to avoid damage to tissue when the distal arm 104 is extended and the locking projection 130 extends radially outwardly when the distal arm 104 is in the locked position in the collar 120.

The collar 120 includes or defines one or more receiving portions 136 configured to operably receive the locking projection 130 of the distal arm 104 when the distal arm 104 is moved to the locked position. The receiving portion(s) 136 may be disposed along a length of the collar 120 corresponding to the position of the locking projection 130 when the distal arm 104 is moved to the closed position. When the distal arm 104 is moved to the locked position, the locking projection 130 may extend into receiving portion 136 of the collar 120 to maintain the position of the distal arm 104 relative to the collar 120. The receiving portion 136 and the locking projection 130 may be sized, shaped, and configured such that the locking projection 130 is prevented from withdrawing from the receiving portion 136, such as to maintain the distal arm 104 in the closed position after the tissue clipping assembly 102 is decoupled from the drive assembly 200. The locking projection 130 may remain in the receiving portion 136 of the collar 120 after the tissue clipping assembly 102 is deployed from the drive assembly 200, such as to keep the tissue clipping assembly 102 in the closed position to clip tissue.

In some embodiments, the locking projection 130 includes a ramp portion 132 at a proximal end and a shoulder portion 134 at a distal end. The ramp portion 132 may be configured to permit the locking projection 130 to be moved into the receiving portion 136 of the collar 120. For example, the ramp portion 132 may be angled or sloped such that the locking projection 130 may slide beneath the inner surface of the collar 120 as the distal arm 104 is retracted into the collar 120 to position the locking projection 130 in the receiving portion 136. The shoulder portion 134 may be configured to retain the locking projection 130 in the receiving portion 136 of the collar 120 such that the distal arm 104 is prevented from moving distally relative to the collar 120 (e.g., to lock the distal arm 104 with the collar 120 prior to releasing the tissue clipping assembly 102). For example, the shoulder portion 134 may abut a side of the receiving portion 136 to prevent the locking projection 130 from retracting from the receiving portion 136.

In some embodiments, the collar 120 includes one or more locking tabs 138 extending into the receiving portion 136 to retain the locking projection 130 in the receiving portion 136 of the collar 120. The locking tabs 138 may be flexed or bent radially inwardly to retain the locking projection 130 in the receiving portion 136. In the illustrated embodiment, the collar 120 includes one locking tab 138 extending proximally into the receiving portion 136. However, it will be understood that the collar 120 may have other configurations and assemblies. For example, the collar 120 may include two or more locking tabs 138, and the locking tabs 138 may extend proximally, distally, or laterally into the receiving portion 136.

Figure 12A:
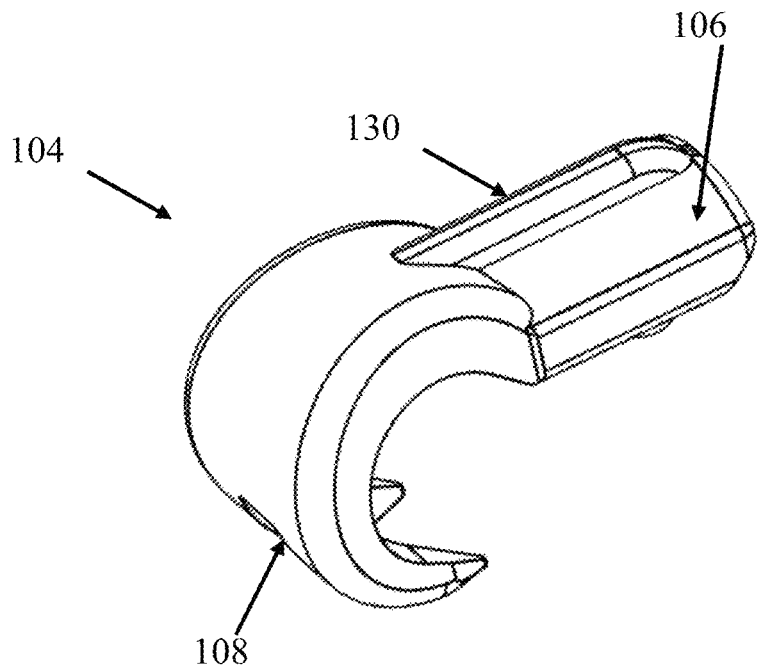
FIG. 12A is a perspective view of a distal arm according to another embodiment.
Figure 12B:
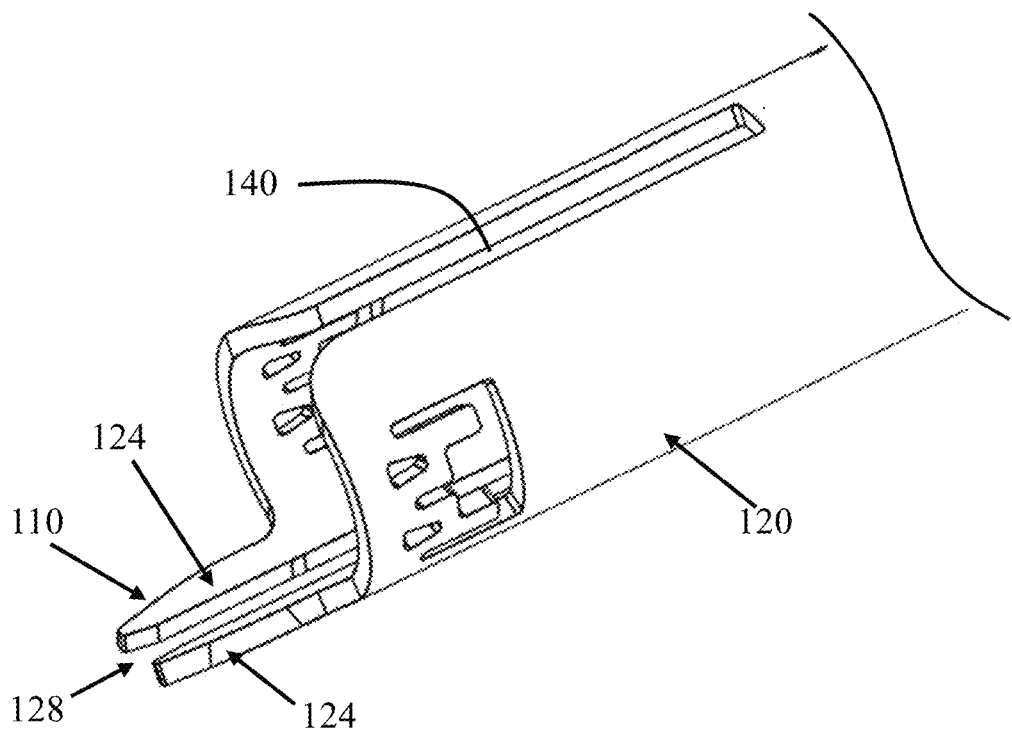
FIG. 12B is a perspective view of a collar according to another embodiment for use with the distal arm of FIG. 12A.
Figure 12C:
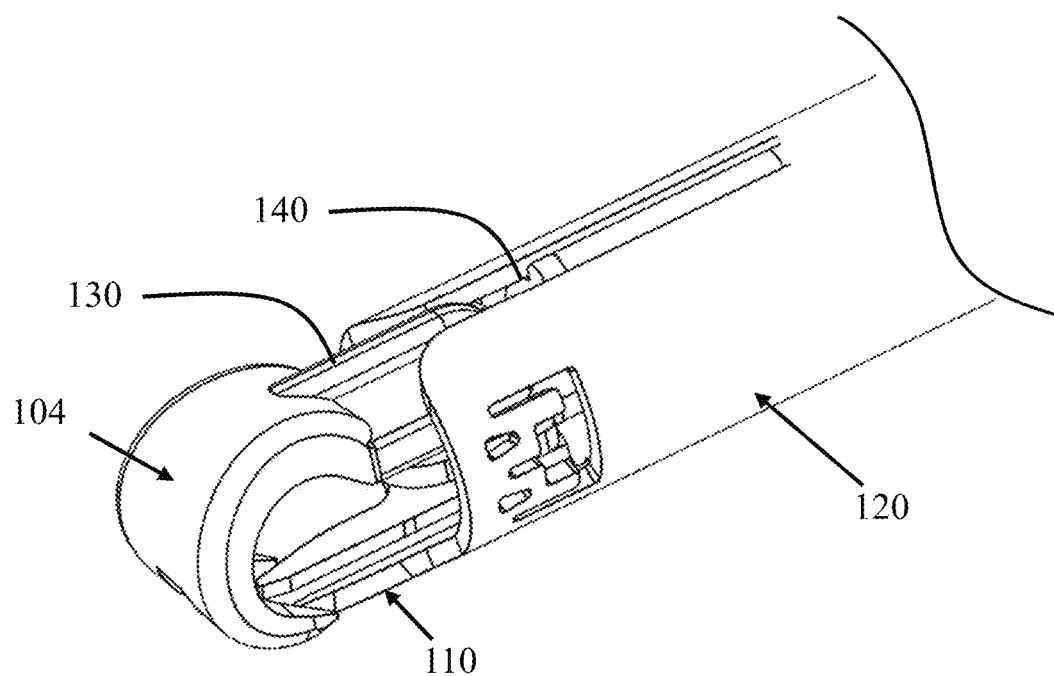
FIG. 12C is a perspective view of distal arm of FIG. 12A retracted into a guiding slot of the collar of FIG. 12B.

In some embodiments, as shown in FIGS. 12A-12C, the collar 120 may include one or more guiding slots 140 extending from the distal end of the collar 120. The guiding slots 140 may be operable to align the distal arm 104 as the distal arm 104 is retracted into the collar 120, such as when the distal arm 104 is retracted into the locked position. In some embodiments, the guiding slots 140 extend distally into receiving portions 136 (not shown). In some embodiments, the guiding slots 140 operate as the receiving portions 136 and lock the distal arm 104 in the closed position. In some embodiments, the guiding slot is separate from the receiving portion 136 and aligns other locking projections 130 with the receiving portion(s) 136 of the collar 120.

During the tissue clipping operation, one of the locking projections 130 of the distal arm 104 may be received in the guiding slot 140 of the collar 120 when the distal arm 104 is retracted. One of the locking projections 130 or another portion of the distal arm 104 may extend into the guiding slot 140 of the collar 120, such as when the distal arm 104 is oriented in the desired position. In some embodiments, the distal ends of the guiding slot 140 are flared or rounded such as to guide the locking projection 130 into the guiding slot 140 and orient the distal arm 104 into the desired position as the distal arm 104 is proximally retracted. The disposition of the locking projection 130 in the guiding slot 140 may also orient the distal arm 104 during the tissue clipping operation, such as to prevent the distal arm 104 from unintentionally rotating during operation.

In some embodiments, the guiding slot 140 may be configured to guide one of locking projections 130 into the receiving portion 136 of the collar 120 to couple the distal arm 104 with the collar 120. For example, the receiving portion 136 may be connected with the proximal end of the guiding slot or the guiding slot 140 may orient the distal arm 104 during retraction such that one of the other locking projections 130 extends into the receiving portion 136. In other embodiments, the guiding slot 140 may be configured to retain the locking projections 130 to maintain the distal arm 104 in the locked position. For example, the proximal portion of the guiding slot 140 may be narrower to provide a compression fit on the locking projection 130 to maintain the distal arm 104 in the locked position.

Figure 13:
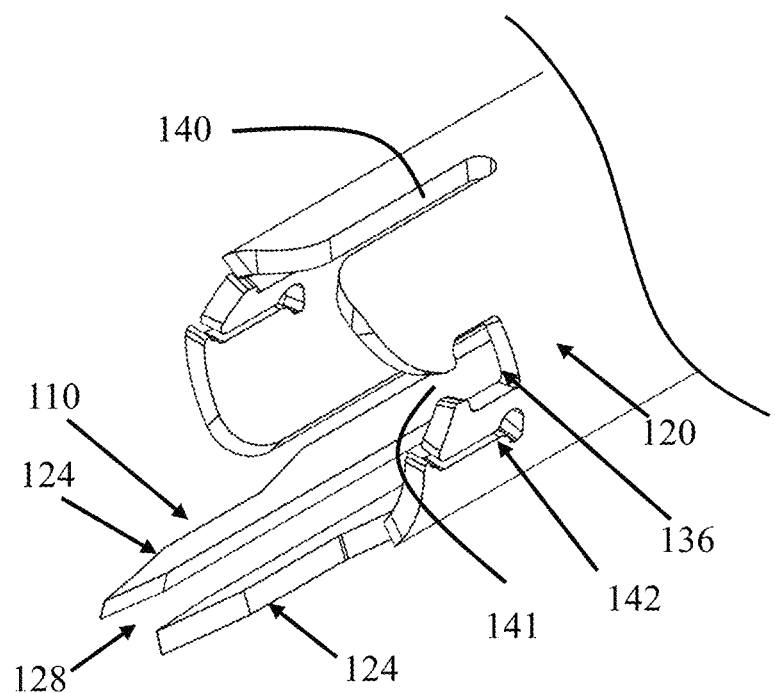
FIG. 13 is a perspective view of a collar according to another embodiment.
Figure 14A:
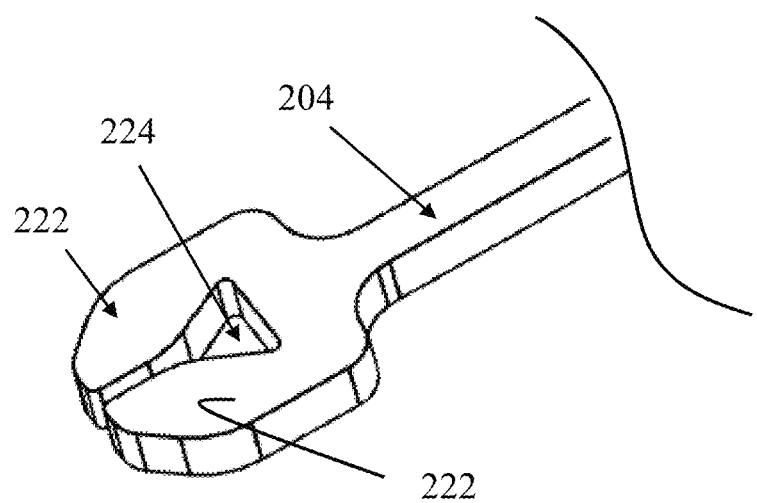
FIG. 14A is a perspective view of a distal end of a drive element according to one embodiment.
Figure 14B:
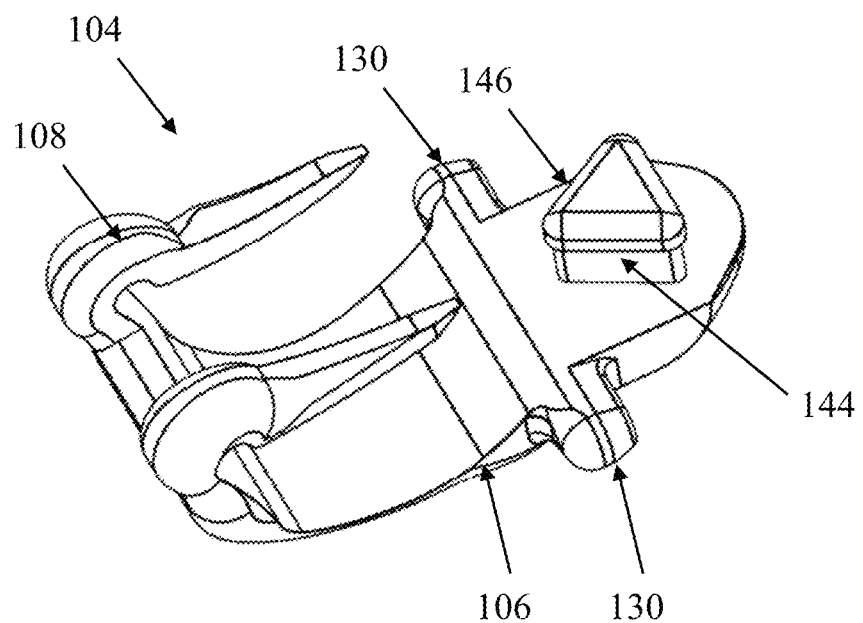
FIGS. 14B and 14C are perspective and side views of a distal arm for use with the drive element of FIG. 14A.
Figure 14C:
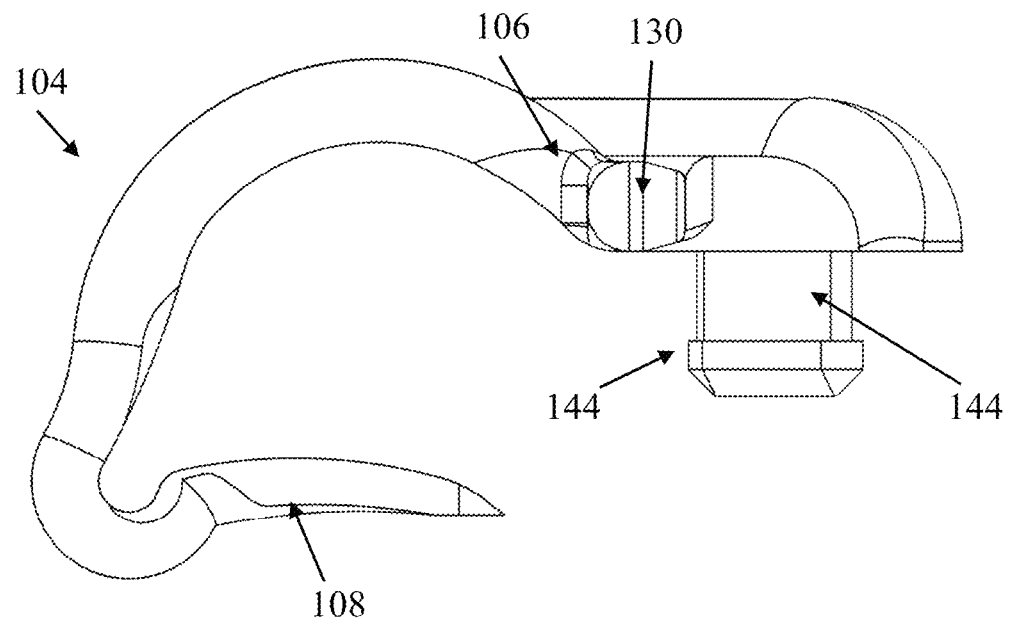
Figure 14D:
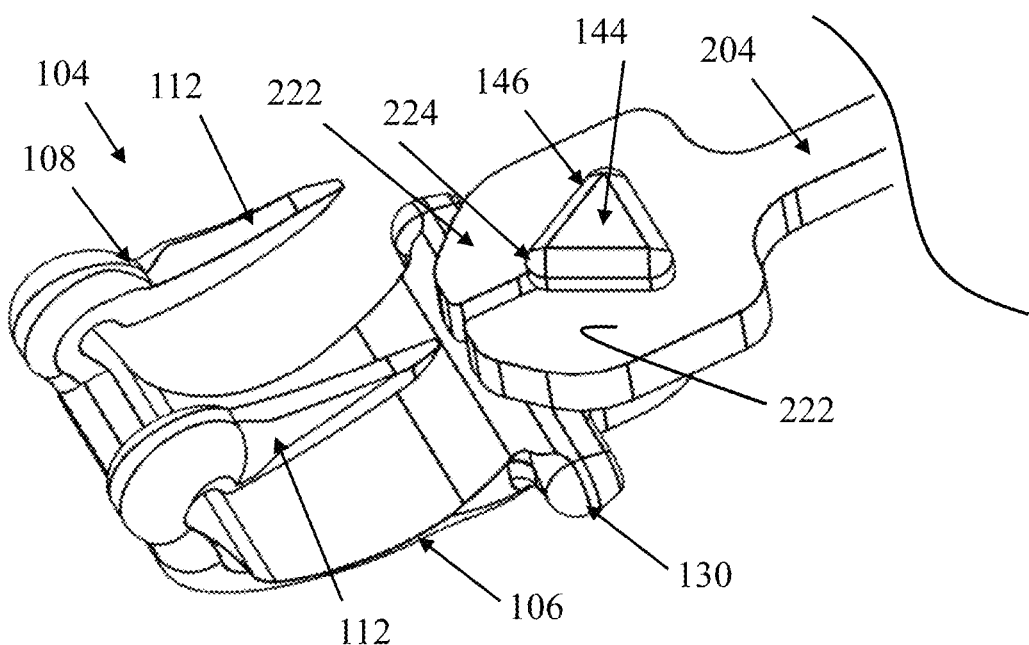
FIG. 14D is a perspective view of the drive element of FIG. 14A coupled with the distal arm of FIGS. 14A-14B.

In some embodiments, as shown in FIG. 13, the collar 120 may include setting recesses 141 at the distal end of the collar 120 and in line with the receiving portions 136. Each setting recess 141 may be configured to allow the tissue clipping assembly 102 to be moved near the closed position and to allow the operator to observe the clipping of the tissue with the tissue clipping assembly 102 before the distal arm 104 is locked with the collar 120. The setting recesses 141 may be a distally opening channel or groove in the distal end of the collar 120. The collar 120 may narrower between the setting recesses 141 and the receiving portions 136, such as to prevent accidental locking of the distal arm 104 and to maintain the distal arm 104 in the locked position when one of the locking projections 130 are disposed in the receiving portions 136. In some embodiments, the device 100 may be extended through the catheter 212 and/or the endoscope with the locking projection(s) 130 disposed in the setting recess (es) 141.

During operation, the distal arm 104 may be retracted, such as via the drive element 204, such that the locking projection 130 of the distal arm 104 is disposed in the setting recess 141. The operator may observe the clipping of the tissue with the tissue clipping assembly 102 to determine if the tissue clipping assembly 102 is properly clipping tissue. The operator may regrasp tissue with the distal and proximal arms 104, 110 if it is determined that the tissue clipping assembly 102 is not properly grasping tissue. Alternatively, the distal arm 104 may be retracted, such as via the drive element 204 to move the locking projection 130 of the distal arm 104 into the receiving portion 136 if it is determined that the tissue clipping assembly 102 is properly grasping tissue. The distal arm 104 may remained locked with the collar 120 when the locking projection(s) 130 are moved from the setting recess(es) 141 to the receiving portion(s) 136 of the collar 120.

In the illustrated embodiment, the collar 120 includes setting recesses 141 and receiving portions 136 on both sides of the collar 120 and a guiding slot 140 at the top of the collar 120. The collar 120 also includes a stress relief 142 on one side of each setting recess 141 and receiving portion 136 pair. The stress relief 142 may permit the collar 120 to flex, bend, or compress such that the locking projection 130 may be moved from the setting recess 141 to the receiving portion 136. The collar 120 may regain its shape after the locking projection 130 is disposed in the receiving portion 136 to maintain the distal arm 104 in the locked position. The stress reliefs 142 may be grooves or cut outs which permit the collar 120 to flex, bend, or compress. Further, it will be understood that any of the features of the collar 120 of FIG. 13 may be incorporated into any of the collars 120 described herein.

Referring now to FIGS. 14A-18, the one or more drive elements 204 may be operably coupled with the tissue clipping assembly 102, such as the distal arm 104, in a variety of manners such that the drive elements 204 may be decoupled from the tissue clipping assembly 102, such as after the tissue clipping assembly 102 clips tissue. In some embodiments, the drive element 204 is operably coupled directly to the proximal end of the distal arm 104. In other embodiments, the drive element 204 is operably coupled to the proximal end of the distal arm 104 via one or more couplers 214. The one or more couplers 214 may be fixed to the distal end of the drive element 204 via welding, crimping, swaging, soldering, adhesives, fasteners, or the like. The coupler 214 may also be integral with the drive element 204.

In some embodiments, the drive element 204 may be decoupled from the distal arm 104 by proximally retracting the drive element 204 with sufficient force, such as after the tissue clipping assembly 102 has been moved to the closed and locked positions. In some embodiments, the proximal force applied to the drive element 204, such as a force applied by the operator via the handle 202, to decouple the drive element 204 from the distal arm 104 is between about 10 pounds and about 25 pounds such that the force applied to the coupling between the drive element 204 and the distal arm 104 is between about 5 pounds and about 10 pounds.

In some embodiments, the distal end of the drive element 204 is sized, shaped, and configured to operably couple with the distal arm 104 during operation of the distal arm 104 and to operably decouple from the distal arm 104 after the tissue clipping assembly 102 has been moved to the closed position. As shown in FIGS. 14A-14D, the distal end of the drive element 204 includes two prongs 222 extending distally from the remainder of the drive element 204. The prongs 222 may be shaped and configured to define a coupling area 224 between the prongs 222. The prongs 222 may be closer together at the distal end such that the distal opening to the coupling area 224 is narrower than the proximal portion of the coupling area 224.

The distal arm 104, such as the extending portion 106, includes one or more coupling projections 144 configured to be operably received in the coupling area 224 defined by the prongs 222 of the drive element 204. The coupling projection 144 may extend from the extending portion 106 of the distal arm 104 in a manner to increase the recruitment of tissue, such as during the clipping operation, by increasing the space beneath the grasping portion 108 of the distal arm 104 in which tissue may be grasped. For example, the coupling projection 144 may extend a distance below the extending portion 106 to increase the space beneath and/or proximal to the distal tines 112 such that the distal tines 112 may grasp tissue.

The coupling projection(s) 144 and the prongs 222 may be sized, shaped, and configured such that the coupling projection 144 may be operably received in the coupling area 224 defined between the prongs 222 during operation and operably released from the coupling area 224, such as after the tissue clipping assembly 102 has been moved to the closed and locked positions. The coupling projection 144 may be inserted through the distal opening between the prongs 222 and be disposed in the coupling area 224 defined by the prongs 222. The distal ends of the prongs 222 may extend around a distal portion of the coupling projection 144 to operably retain the coupling projection 144 in the coupling area 224. In some embodiments, the prongs 222 snap fit around the coupling projection 144 to retain the coupling projection 144 in the coupling area 224. When the coupling projection 144 is disposed in the coupling area 224 and the prongs 222 extend distally around the coupling projection 144, the coupling projection 144 may be retained in the coupling area 224 and the distal arm 104 may be coupled with the drive element 204 such that linear and/or rotational movement of the drive element 204 is transferred to the distal arm 104. The prongs 222 may be sized, shaped, and configured to retain the coupling projection 144 in the coupling area 224 and maintain the coupling of the drive element 204 and the distal arm 104 during the tissue clipping operation. In some embodiments, the prongs 222 are configured to bias radially inwardly around the coupling projection 144 such that the prongs 222 retain the coupling projection 144 in the coupling area 224 during operation.

The coupling projection 144 may also be withdrawn from the coupling area 224 to decouple the distal arm 104 from the drive element 204, such as after the tissue clipping assembly 102 has been moved to the closed and locked positions. The drive element 204 may be proximally retracted, such as via the handle 202, with sufficient force such that the prongs 222 are proximally retracted from the coupling projection 144 and the coupling projection 144 is pulled out of the coupling area 224 and through the distal opening between the prongs 222. The prongs 222 may flex or bend radially outwardly, such as by contacting wider proximal portions of the coupling projection 144, as the drive element 204 is retracted such that the prongs 222 release the coupling projection 144 from the coupling area 224. The force required to pull the tissue clipping assembly 102 out of the coupling area 224 defined by the prongs 222 may be greater than the force required to recruit tissue with the distal arm 104 such that the distal arm 104 is not prematurely decoupled from the drive element 204. After the prongs 222 are retracted proximally from the coupling projection 144, the distal arm 104 may be decoupled from the drive element 204 and the drive element 204 may be withdrawn from the distal arm 104, such as with the tissue clipping assembly 102 in the closed and locked positions and clipping tissue.

In some embodiments, the coupling projection 144 includes a shoulder 146 extending outwardly from the remainder of the coupling projection 144. The shoulder 146 of the coupling projection 144 may be spaced apart from the remainder of the distal arm 104 and sized, shaped, and configured to receive the drive element 204 between the shoulder 146 and the outer surface of the distal arm 104 from which the coupling projection 144 extends. The shoulder 146 may abut the top or bottom of the drive element 204, such as the top and bottom of the prongs 222, such that the distal end of the drive element 204 is substantially prevented from sliding off the top or bottom of the coupling projection 144. For example, in the illustrated embodiment, the shoulder 146 is disposed at the bottom of the coupling projection 144 such that the prongs 222 may be disposed around the remainder of the coupling projection 144 and such that the shoulder 146 abuts the bottom of the drive element 204, thereby preventing the prongs 222 from slipping off the bottom of the coupling projection 144.

In the illustrated embodiment, the coupling projection 144 is oriented substantially downwardly from the extending portion 106 and is substantially triangular and pointed distally with the proximal end being wider than the proximal end. The narrower distal end of the coupling projection 144 may permit the coupling projection 144 to be withdrawn from the coupling area 224 defined by the prongs 222 of the drive element 204, such as after the tissue clipping assembly 102 has clipped tissue, to decouple the distal arm 104 from the drive element 204. For example, the narrower distal end of the coupling projection 144 may be angled such that the prongs 222 radially separate as the drive element 204 is retracted relative to the coupling projection 144. However, it will be understood that the coupling projection 144 may have other shapes and configurations. For example, the coupling projection 144 may have a circular, elliptical, ovular, rectangular, or other suitable shape and the coupling projection 144 may be oriented substantially upwardly from the extending portion 106.

While the prongs 222 have been described as forming a part of the distal end of the drive element 204, it will be understood that the drive assembly 200 may have other assemblies and configurations. For example, the prongs 222 may be formed on a coupler 214 that is fixed to the distal end of the drive element 204 such that the distal end of the drive element 204 may be releasably coupled with the distal arm 104 via the coupler 214.

Figure 15A:
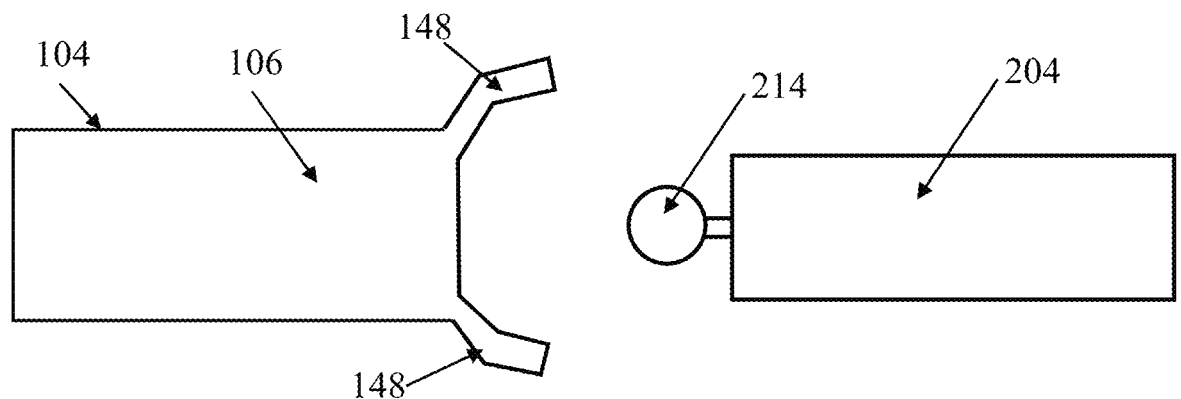
FIGS. 15A and 15B are schematic illustrations showing a distal arm coupled to a drive element via a coupler according to one embodiment.
Figure 15B:
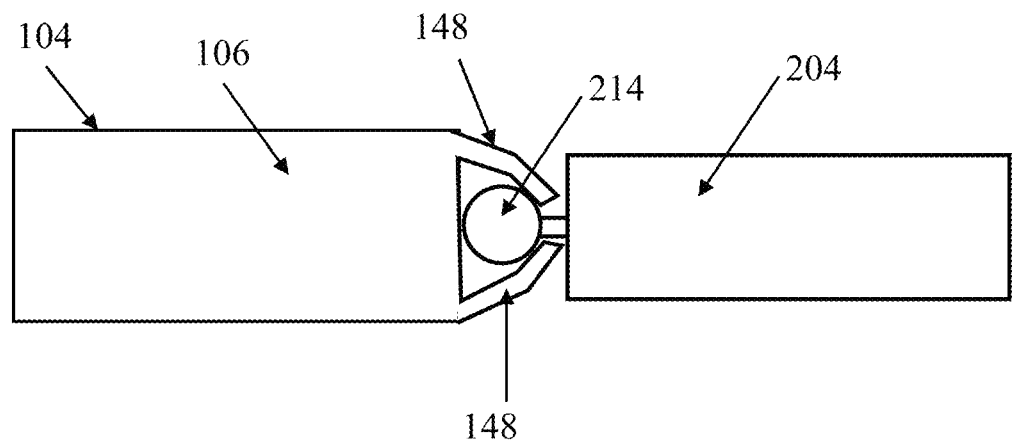

In some embodiments, as shown in FIGS. 15A and 15B, the proximal end of the distal arm 104, such as the proximal end of the extending portion 106, includes one or more tabs 148 configured to operably couple the distal arm 104 with the drive element 204. The tabs 148 extend from the proximal end of the distal arm 104 and are flexible or pivotable to operably couple the distal arm 104 with the drive element 204. The drive element 204 may include or be coupled with a coupler 214. The coupler 214 may be sized, shaped, and configured to be operably retained by the tabs 148 of the distal arm 104 to couple the distal arm 104 with the drive element 204.

In the illustrated embodiment, the coupler 214 has a substantially spherical coupling portion at a distal end configured to couple with the tabs 148 of the distal arm 104. In some embodiments, the coupler 214 is welded to the distal end of the drive element 204. In some embodiments, the coupler 214 includes a neck portion fixed to the distal end of the drive element 204 such that the drive element 204 may control the position and/or rotation of the distal arm 104. In some embodiments, the coupler 214 is rectangular, helical, obround, asymmetric, or otherwise shaped to provide translational and/or rotational force to the distal arm 104 when coupled between the drive element 204 and the distal arm 104.

The tabs 148 of the distal arm 104 may be configured to flex or bend around the coupler 214, such as the spherical coupling portion of the coupler 214, to couple the drive element 204 with the distal arm 104. The bent tabs 148 may prevent or otherwise restrict the coupler 214 from being retracted from distal arm 104 during the tissue clipping operation. For example, the tabs 148 may be sized and shaped to substantially cover a proximal side of the coupler 214. Additionally, the tabs 148 may remain disposed around the coupler 214 during operation such that linear and/or rotational motion of the drive element 204 may be transferred to the distal arm 104.

The tabs 148 may be flexed outwardly to decouple the drive element 204 from the distal arm 104, such as after the tissue clipping assembly 102 has been moved to the closed position. The drive element 204 may be retracted proximally with sufficient force, such as via the handle 202, to disengage the tabs 148 from retaining the coupler 214 to the distal arm 104. The drive element 204 may be retracted with a force sufficient to retract the coupler 214 such that the tabs 148 bend radially outwardly and no longer surround the coupling portion of the coupler 214. The force required to release the tabs 148 may be greater than the force required to recruit tissue with the distal arm 104. After tabs 148 have bent radially outwardly, the drive element 204 and the coupler 214 may be retracted proximally from the distal arm 104, such as with the tissue clipping assembly 102 clipping tissue.

Additionally or alternatively, the distal end of the drive element 204 may include one or more detents extending radially into the outer surface of the drive element 204 which are each configured to receive a tab 148 extending from the proximal end of the extending portion 106 of the distal arm 104. The tabs 148 of the distal arm 104 may be pivoted or flexed such that the tabs extend into the detents to operably couple the drive element 204 with the distal arm 104. The tabs 148 may be disengaged by proximally retracting the drive element 204 relative to the distal arm 104 to bend the tabs 148 out of the detents, thereby decoupling the drive element 204 from the distal arm 104.

In some embodiments, the proximal end of the distal arm 104 may include a bore or recess configured to receive the coupler 214, such as the spherical coupler. The coupler 214 may be inserted into the bore of the distal arm 104 and the distal arm 104 may be connected the coupler 214, such as by crimping, swaging, or welding the distal arm 104 around the coupler 214 to couple the drive element 204 and the distal arm 104. The drive element 204 may be decoupled from the distal arm 104 by retracting the drive element 204 relative to the distal arm 104 to break or otherwise disrupt the one or more connections, such as the crimp, such that the coupler 214 may be retracted from the distal arm 104.

In some embodiments, the distal arm 104 may be coupled with the drive element 204 by a frangible coupling. The distal arm 104 may be coupled with the drive element 204 until a sufficient proximal force is applied to the drive element 204, such as via the handle 202, to break or otherwise disrupt the coupling between the drive element 204 and the distal arm 104, such as after the tissue clipping assembly 102 has been moved to the closed position to clip tissue.

Figure 16A:
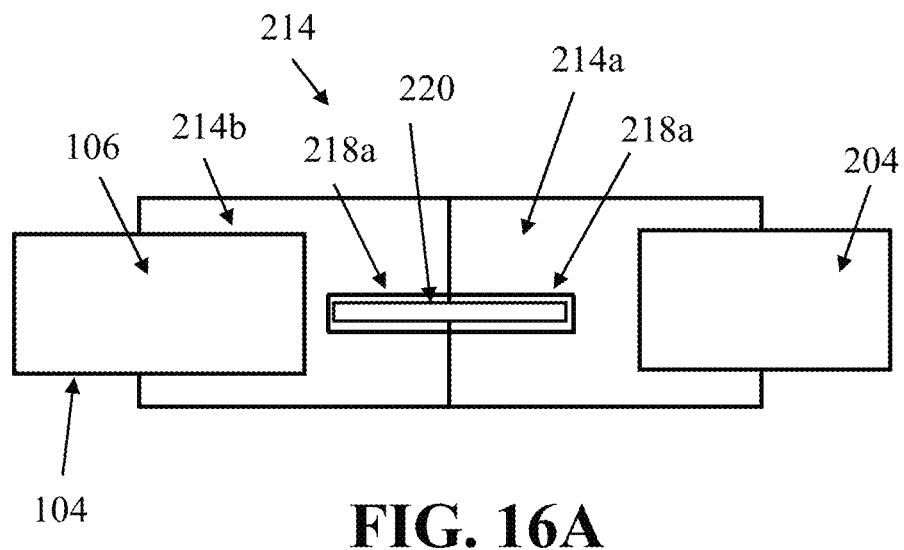
FIGS. 16A and 16B are schematic illustrations showing a distal arm coupled to a drive element via a coupler according to another embodiment.
Figure 16B:
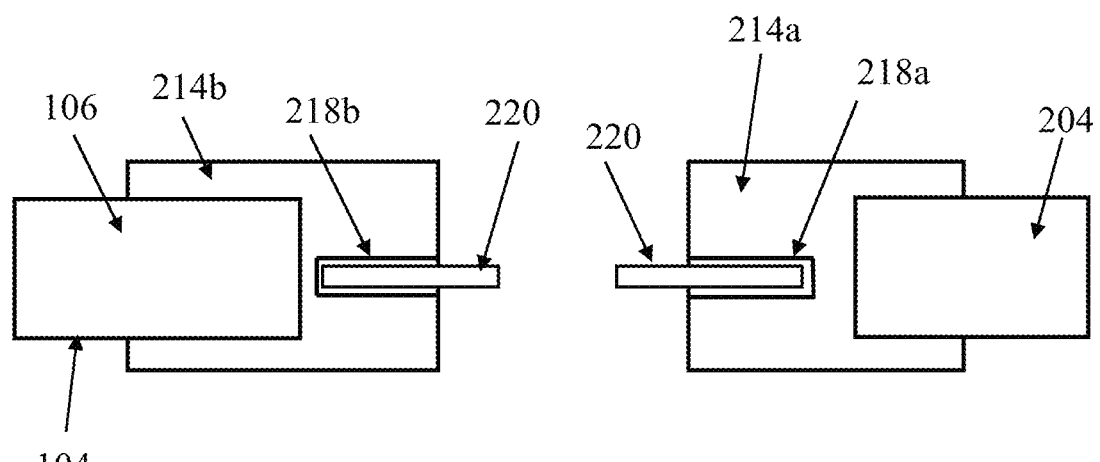

As shown in FIGS. 16A and 16B, the coupler 214 may be substantially cylindrical with a first portion 214a fixed around the distal end of the drive element 204 and a second portion 214b fixed around the proximal portion of the distal arm 104, such as fixed around the proximal portion of the extending portion 106 of the distal arm 104. The coupler 214 includes a channel 218 extending into the coupler 214, such as with a first channel portion 218a extending proximally into the first portion 214a from a distal end of the first portion 214a and a second channel portion 218b extending distally into the second portion 214b from a proximal end of the second portion 214b. A coupling link 220 extends into and is secured in the channel 218, such as with a proximal portion of the coupling link 220 secured in the first channel portion 218a and a distal portion of the coupling link 220 secured in the second channel portion 218b. When secured, the coupling link 220 may operably couple the drive element 204 with the distal arm 104. In some embodiments, the coupling link 220 is laser welded into the first and second channel portions 218a, 218b of the channel 218.

The coupling link 220 may be sized, shaped, and configured such that translation and/or rotation of the drive element 204 is transmitted to the distal arm 104 when the coupling link 220 couples the drive element 204 and the distal arm 104. The coupling link 220 may also be sized, shaped, and configured such that it breaks when subjected to a desired tensile load, such as the force applied to the coupling link 220 when the tissue clipping assembly 102 is in the closed position and the drive element 204 is proximally retracted. When the coupling link 220 is broken, the distal arm 104 may be decoupled from the drive element 204 such that the drive element 204 may be retracted from the distal arm 104. In some embodiments, the coupling link 220 comprises stainless steel or Nitinol, or combinations thereof.

While the coupler 214 of FIGS. 16A and 16B has been described as including a first portion 214a disposed around the drive element 204, a second portion 214b disposed around the distal arm 104, and a channel 218, it will be understood that the coupler 214 may have other configurations and assemblies. For example, the coupler 214 may form the coupling link 220 by directly coupling the distal end of the drive element 204 with the proximal end of the distal arm 104. The coupling link 220 may be operable to transmit the movement and/or rotation of the drive element 204 to the distal arm 104 when the coupling link 220 couples the drive element 204 and the distal arm 104. The coupling link 220 may also be configured to break and thereby decouple the drive element 204 from the distal arm 104 when the coupling link 220 is subjected to a desired tensile load, as described above. Additionally or alternatively, a portion of the distal arm 104 and/or a portion of the drive element 204 may be frangible such that the drive element 204 may be coupled with the distal arm 104 during operation and broken under a predetermined load to decouple the distal arm 104 from the drive element 204.

Figure 17A:
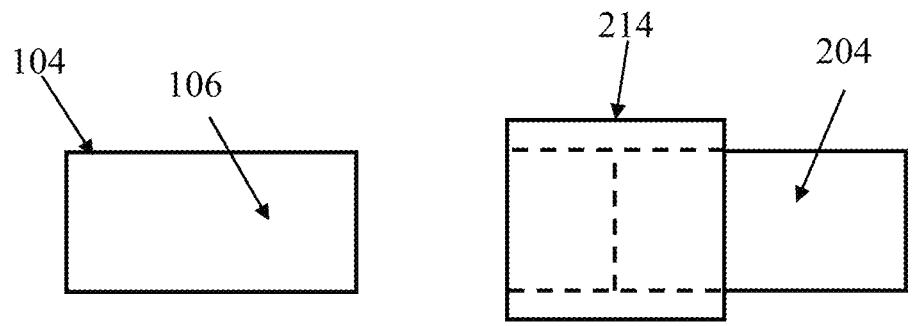
FIGS. 17A-17C are schematic illustrations showing a distal arm coupled to a drive element via a coupler according to another embodiment.
Figure 17B:
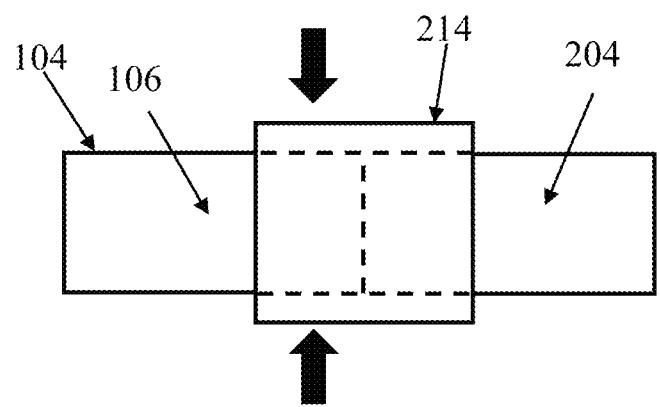
Figure 17C:
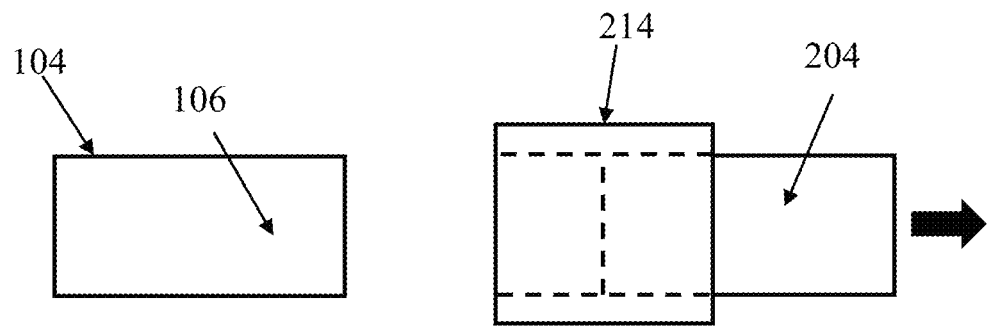

As shown in FIGS. 17A-17C, the drive assembly 200 may include a coupler 214 that is substantially tubular and disposed around the distal end of the drive element 204. The coupler 214 may be a hypotube. The coupler 214 may be disposed around the distal end of the drive element 204 such that a portion of the coupler 214 extends distally beyond the distal end of the drive element 204 (FIG. 17A). The coupler 214 may be fixed to the drive element 204 via a swage, such as a swaging the inner surface of the coupler 214 to the drive element 204. The coupler 214 may also be crimped or welded to the drive element 204. The proximal end of the distal arm 104, such as the proximal end of the extending portion 106, may be inserted into distal end of the coupler 214 and the coupler 214 may be operably secured with the distal arm 104. The distal end of the coupler 214 may be connected, such as via crimping, distally to the proximal end of distal arm 104 (FIG. 17B) such that distal arm 104 is coupled with the drive element 204 via the coupler 214, such as to maneuver the distal arm 104 to grasp tissue.

The coupler 214 may operably decouple the distal arm 104 from the drive element 204, such as after the tissue clipping assembly 102 has been moved to the closed and locked positions to clip tissue. The drive element 204 may be retracted proximally with sufficient force to break or otherwise disrupt the connection, such as the crimp, between the coupler 214 and the distal arm 104. When the connection (e.g., the crimp) of the coupler 214 to the distal arm 104 is broken or disrupted, the distal arm 104 may be decoupled from the drive element 204 (FIG. 17C). The force required to break or disrupt the connection may be less than the force required to pull the tissue clipping assembly 102 from the tissue. After connection has been broken, the drive element 204 and the coupler 214 may be retracted from the distal arm 104, such as with the tissue clipping assembly 102 clipping tissue. While the coupler 214 has been described as being connected to the distal arm 104 via a crimp, it will be understood that the coupler 214 may be connected to the distal arm 104 in other manners, such as via swaging, soldering, and welding.

Further, it will be understood that the proximal end of the distal arm 104 may be further coupled with the distal end of the drive element 204 within the coupler 214. For example, the proximal end of the distal arm 104, such as the proximal end of the extending portion 106, may be configured to operably interlock with the distal end of the drive element 204 (see FIG. 9A).

Figure 18:
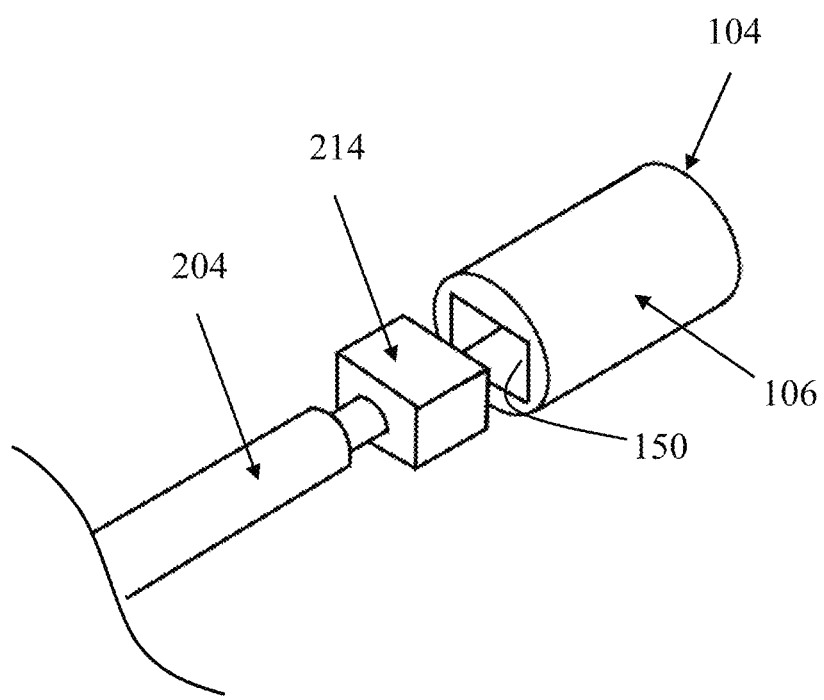
FIG. 18 is a perspective view of a drive element coupling with a distal arm via a coupler according to another embodiment.

In some embodiments, the coupler 214 has a size, shape, and configuration that permits the coupler 214 to be inserted into and interlocked with a portion of the distal arm 104 until the coupler 214 is moved to an unlocked position. As shown in FIG. 18, the proximal end of the distal arm 104, such as the proximal end of the extending portion 106, includes a coupling bore 150 extending distally into the distal arm 104. The coupling bore 150 may be a bore with a proximal opening which substantially corresponds to a shape of the coupler 214. The distal portion of the coupling bore 150 may have a width or diameter larger than the proximal opening of the coupling bore 150. The coupler 214 may be inserted into the coupling bore 150 in a position corresponding to the shape of the proximal opening. After the coupler 214 is inserted through the proximal opening into the coupling bore 150, the coupler 214 may be rotated to operably secure the coupler 214 in the coupling bore 150.

In some embodiments, the coupling bore 150 is configured such that the coupler 214 may be rotated a predetermined amount in the coupling bore 150 such that the coupler 214 operably locks in place in the coupling bore 150. For example, rotating the coupler 214 may cause the cross section of the coupler 214 to have a shape which prevents the coupler 214 from being retracted from the proximal opening of the coupling bore 150. The coupling bore 150 may include one or more locking elements which prevent or otherwise restrict the coupler 214 from rotating or translating in the coupling bore 150 during operation of the distal arm 104. For example, the coupling bore 150 may include one or more tabs which bend once the coupler 214 is properly disposed in the coupling bore 150 and restrict the opposite rotation of the coupler 214 to operably retain the coupler 214 in position in the coupling bore 150. In some embodiments, the coupler 214 may be magnetically locked in the coupling bore 150 until a sufficient force is exerted on the drive element 204 to overcome the magnetic attraction.

The coupler 214 may be interlocked with the coupling bore 150 of the distal arm 104 such that the distal arm 104 may be translated and/or rotated via the drive element 204 during operation. The coupler 214 may be rotated in the coupling bore 150, such as via the drive element 204, such that the coupler 214 may be retracted from the coupling bore 150 to decouple the drive element 204 from the distal arm 104, such as after the tissue clipping assembly 102 clips tissue. For example, the coupler 214 may be rotated in a direction opposite the direction the coupler 214 is rotated to lock the coupler 214 in the coupling bore 150 such that the cross section of the coupler 214 is aligned with the proximal opening of the coupling bore 150.

In the illustrated embodiment, the coupler 214 is a substantially rectangular block and the proximal opening of the coupling bore 150 is similarly rectangular. However, it will be understood that the coupler 214 and the proximal opening of the coupling bore 150 may have any suitable shapes and configurations. For example, the coupler 214 may be ovular, elliptical, triangular, pentagonal, hooked, or any other suitable shape. Further, while the coupler 214 has been described as extending from the distal end of the drive element 204, it will be understood that the distal end of the drive element 204 may be sized, shaped, and configured to function similarly to the coupler 214 of FIG. 18.

In other embodiments, the coupler 214 may be substantially spherical and the coupling bore 150 may be sized, shaped, and configured to operably receive the coupler 214 in a ball-and-socket connection. The coupler 214 may be inserted, such as via a snap fit or press fit, into the coupling bore 150 of the distal arm 104 to retain the coupler 214 in the coupling bore 150 during operation. The coupling bore 150 may be sized, shaped, and configured to retain the coupler 214, such as having a narrower opening, such that the distal arm 104 may be controlled via the drive element 204 during operation. The coupler 214 may be retracted with a sufficient force, such as sufficient force to overcome the snap fit, to release the coupler 214 from the coupling bore 150 to thereby decouple the drive element 204 from the distal arm 104.

While the coupler 214 of FIG. 18 has been described as having a shape which may be correspond to the shape of the proximal opening of the coupling bore 150 of the distal arm 104, it will be understood that the coupler 214 may have other configurations such that coupler 214 may be retained in the coupling bore 150. For example, the coupler 214 may form or include the coupling link 220 that is deformable such that the coupling link 220 may couple the distal arm 104 to couple the drive element 204. The opening of the receiving portion 136 may be narrower than the distal portion of the coupling bore 150. The coupling link 220 be inserted into the coupling bore 150 and may bend or deform in the coupling bore 150 such that the coupling link 220 has a width greater than the proximal opening of the coupling bore 150 thereby coupling the drive element 204 and the distal arm 104 and preventing the coupling link 220 from being retracted from the coupling bore 150 during operation. The drive element 204 may be proximally retracted with sufficient force to pull the coupling link 220 out of the deformed state such that the coupling link 220 may be retracted from the coupling bore 150 to decouple the drive element 204 from the distal arm 104. The coupling link 220 may comprise a shape memory and/or superelastic material, such as Nitinol.

Further, the distal end of the drive element 204 may be sized, shaped, and configured to operably couple with the proximal end of the distal arm 104. For example, the distal end of the drive element 204 may be bent into a shape, such as an L-shape, which is received through a portion of the distal arm 104. The distal arm 104 may be linearly extendable and retractable when the drive element 204 is disposed through the portion of the distal arm 104. After the tissue clipping assembly 102 has been moved to the closed position, the shape of the distal end of the drive element 204 may be pulled out of the distal arm 104 such that the drive element 204 is decoupled from the distal arm 104, such as by lifting the L-shaped bend out of a receiving portion of the distal arm 104. Furthermore, it will be understood that the distal arm 104 may be operably coupled with the drive element 204 in other manners, such as described below.

In embodiments in which the distal arm 104 is releasably coupled with the drive element 204, the drive assembly 200 may include one or more components configured to further maintain the coupling of the distal arm 104 and the drive element 204 during operation. For example, the drive assembly 200 may include a sheath or tube disposed around the drive element 204 and substantially covering the coupling of the drive element 204 to the distal arm 104. The sheath or tube may extend to the proximal end of the distal arm 104 to prevent or otherwise restrict the distal arm 104 from decoupling from the drive element 204 during the tissue clipping operation. In some embodiments, the sheath or tube has a distal portion operably interlocked with a proximal portion. When the distal arm 104 is decoupled from the drive element 204, the distal portion may decouple from the proximal portion, such as by proximal retraction of the drive element 204.

While the coupler 214 has been described as being a part of the drive assembly 200 and attached to the distal end of the drive element 204, it will be understood that the coupler 214 may be part of the tissue clipping assembly 102 and be attached to the proximal end of the distal arm 104. Additionally, it will be understood that any of methods of coupling described above may be switched such that the coupling component(s) of the drive element 204 is disposed on the tissue clipping assembly 102 and vice versa. Further, in embodiments in which the proximal arm 110 is translatable by a drive element 204, it will be understood that the proximal end of the proximal arm 110 may similarly be coupled with the drive element 204 such that the proximal arm 110 may be decoupled from the drive element 204.

Referring now to FIGS. 19A-21B the distal arm 104 includes a housing 154 toward the distal end of the distal arm 104. The housing 154 may be configured to reduce trauma to tissue as the distal arm 104 is extended from the catheter 212 and/or to prevent damage to the catheter 212 and/or the endoscope, such as when extending the tissue clipping assembly 102 through the catheter 212 and/or endoscope. The housing 154 may deflect tissue such that the extension of the distal arm 104 is substantially atraumatic when the distal arm 104 is extended from the collar 120. The housing 154 may shroud the proximal arm 110, such as when the tissue clipping assembly 102 is in the closed position, such as to protect the operator, the endoscope, the catheter 212, and/or the patient. The housing 154 may also be configured to operably lock with the collar 120 to secure the distal arm 104 in the closed and locked positions. In some embodiments, the housing 154 and/or the distal tine 112 of the distal arm 104 are releasably coupled to the distal end of the drive element 204.

Figure 19A:
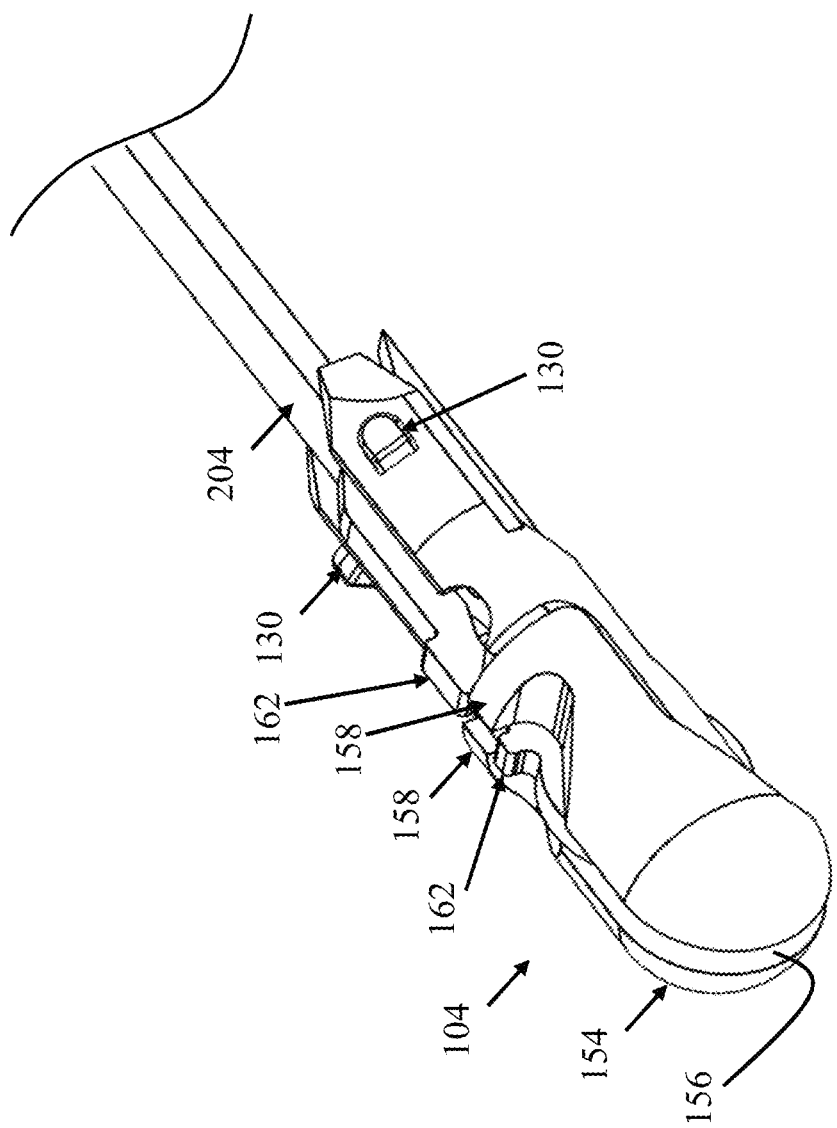
FIGS. 19A and 19B are top and bottom perspective views of a distal arm with a housing according to one embodiment.
Figure 19B:
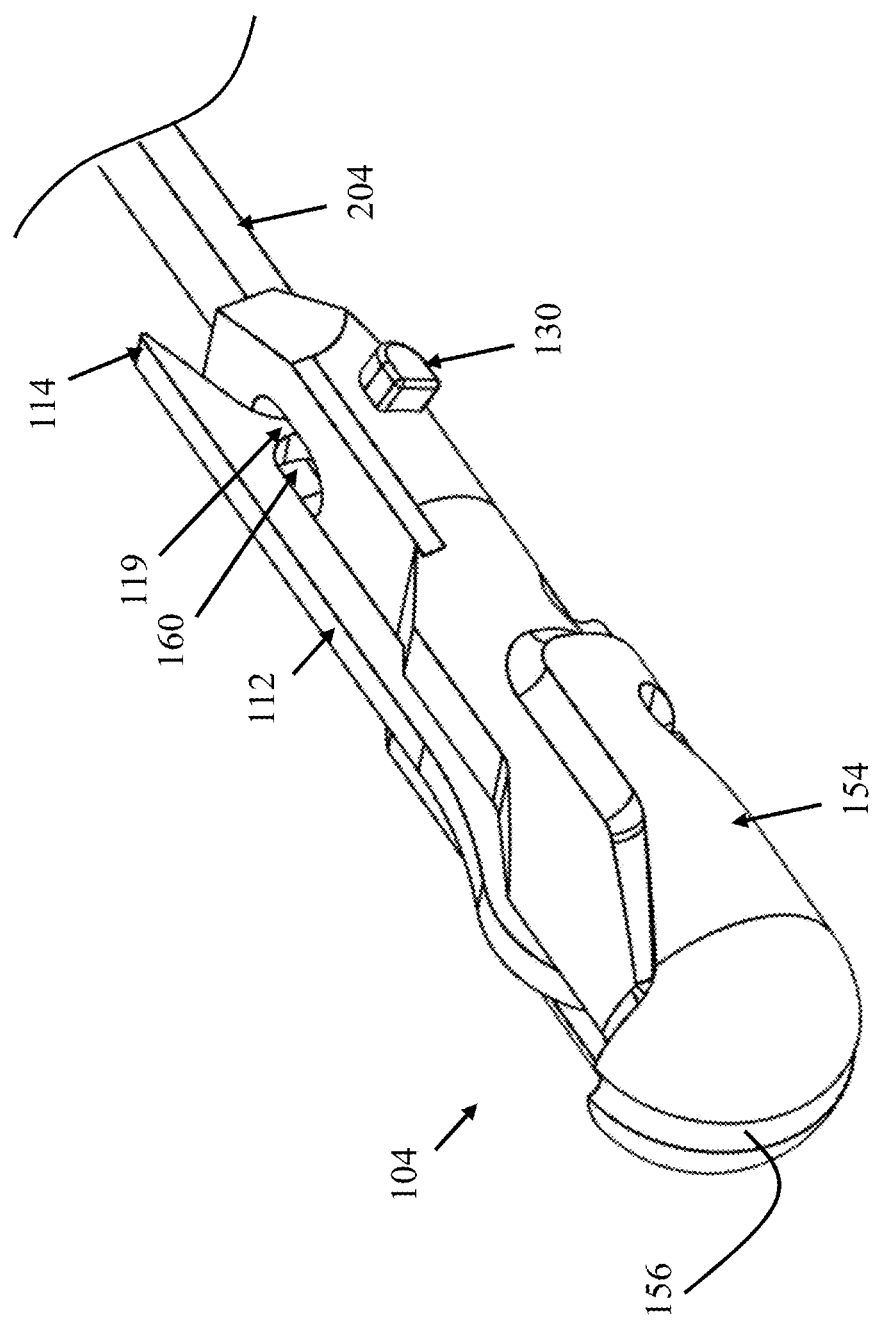
Figure 19C:
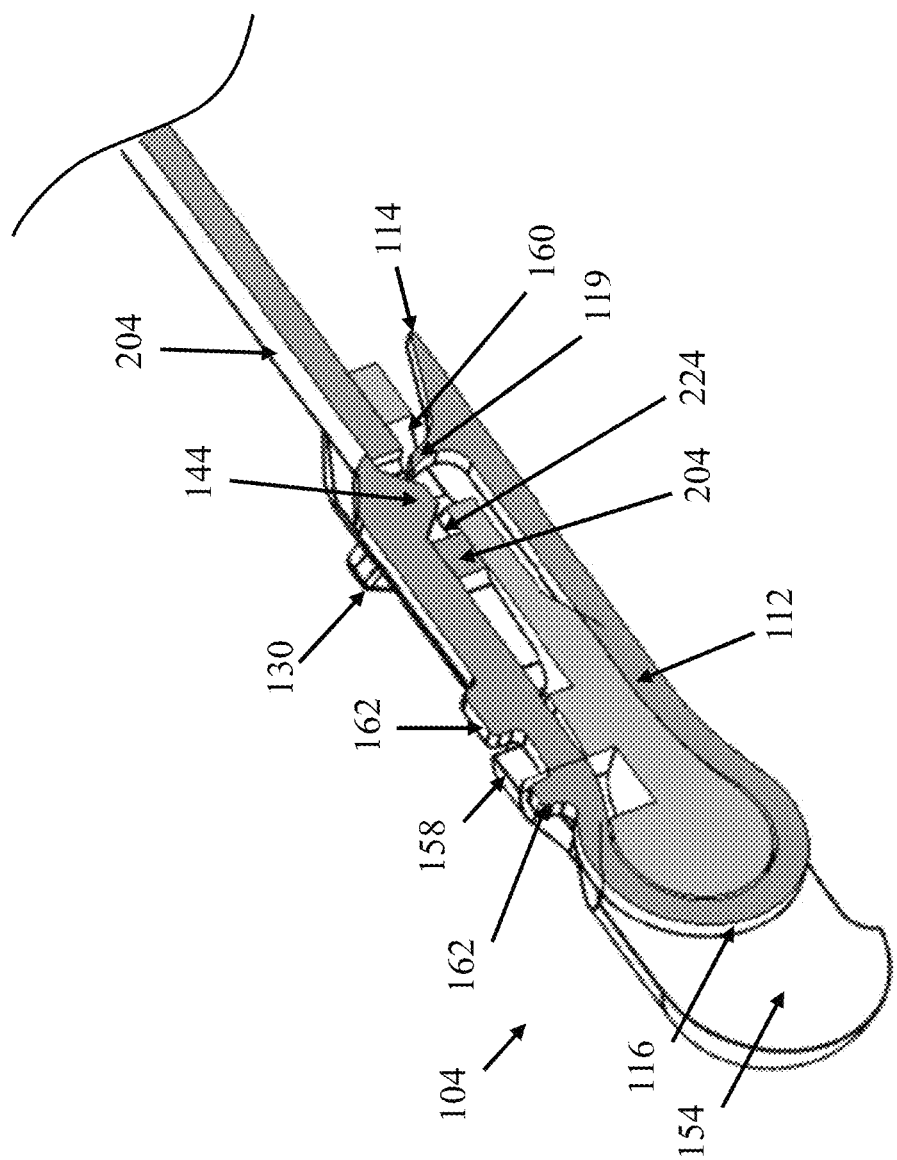
FIG. 19C is a perspective cross section view of the distal arm of FIGS. 19A-19B.
Figure 19D:
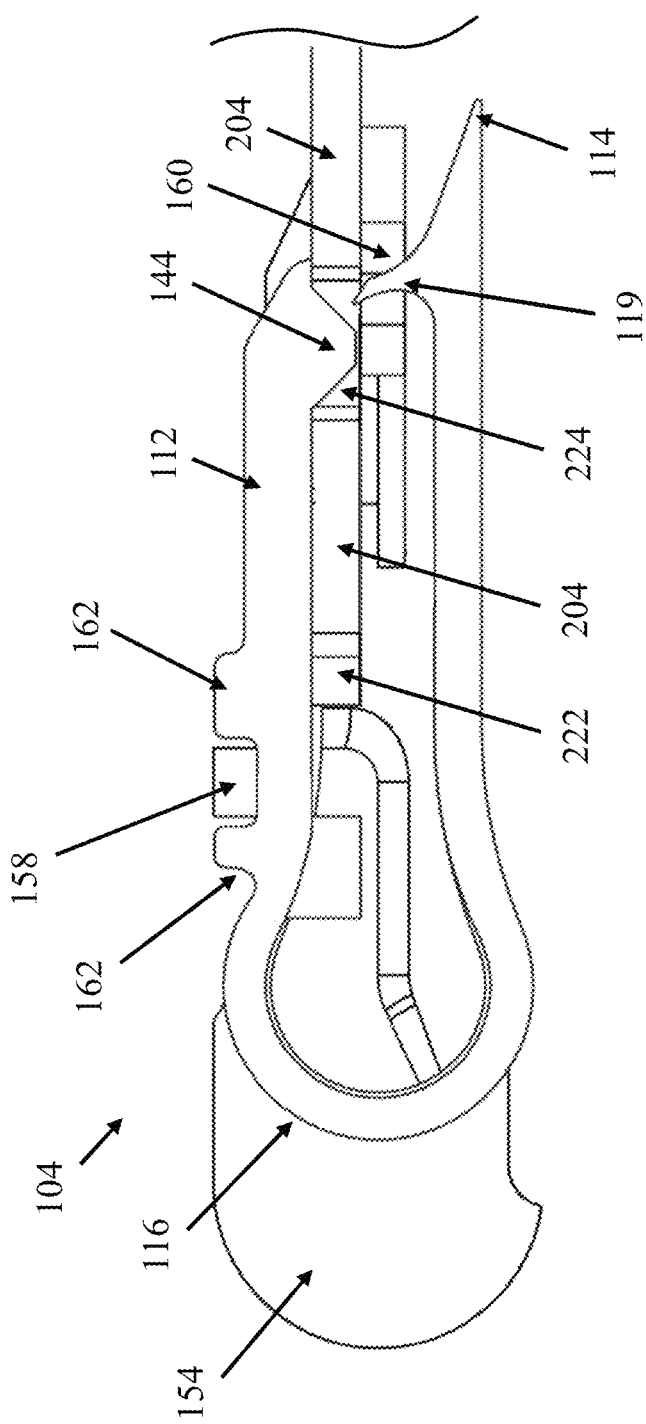
FIG. 19D is a side cross section view of the distal arm of FIGS. 19A-19B.
Figure 19E:
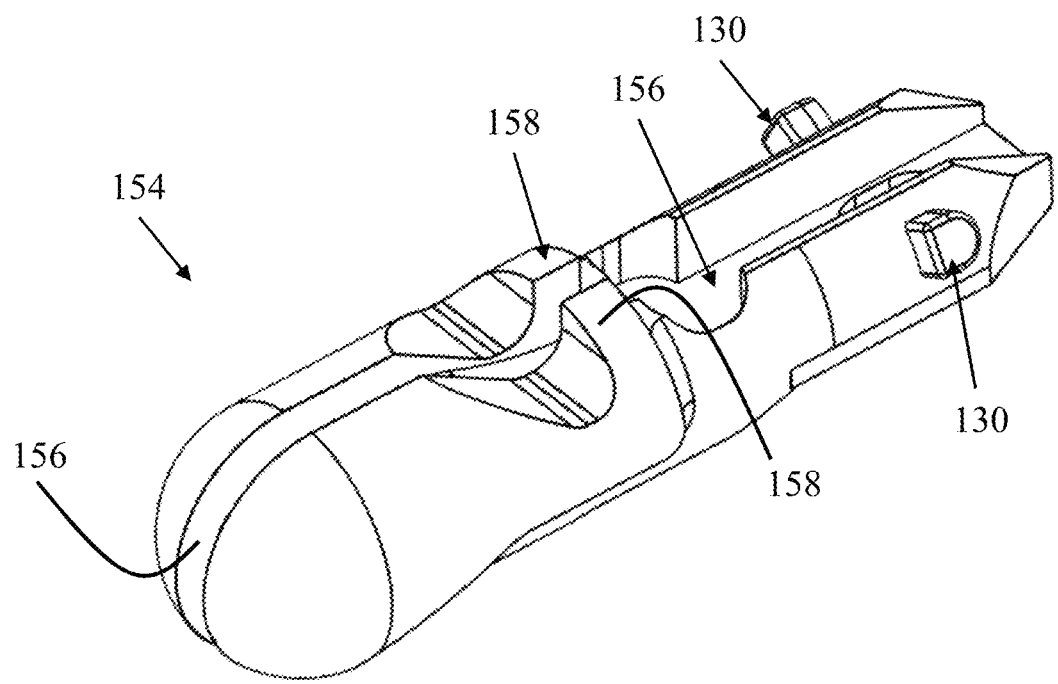
FIGS. 19E-19H are various views of the housing of the distal arm of FIGS. 19A-19B.
Figure 19F:
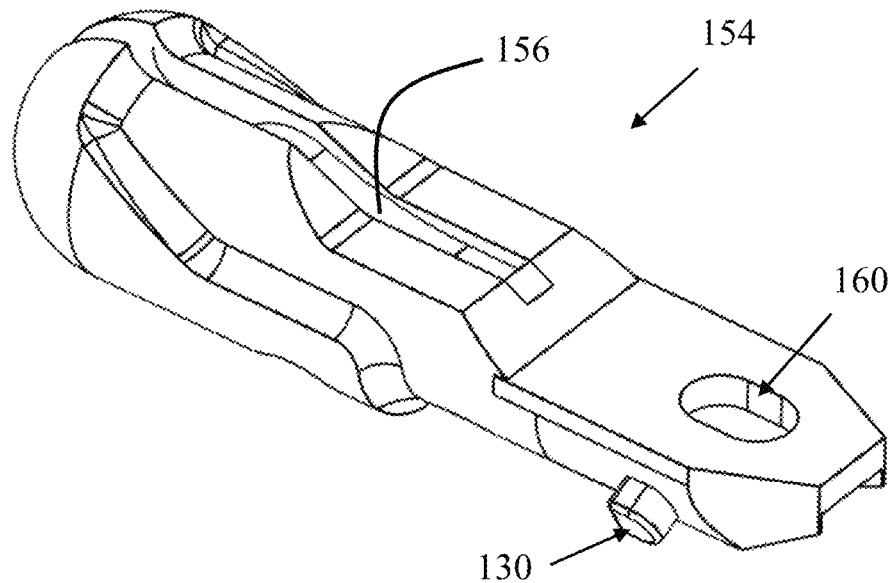
Figure 19G:
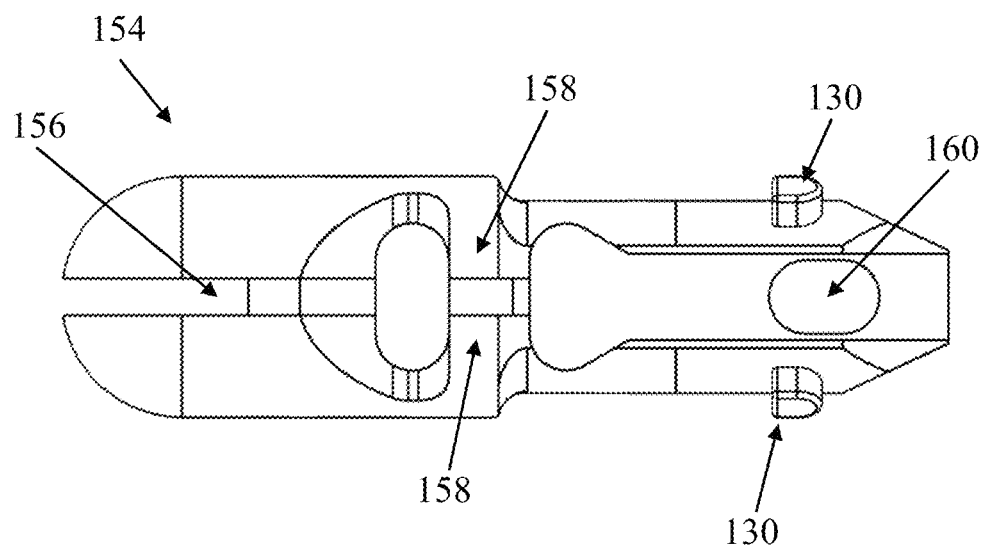
Figure 19H:
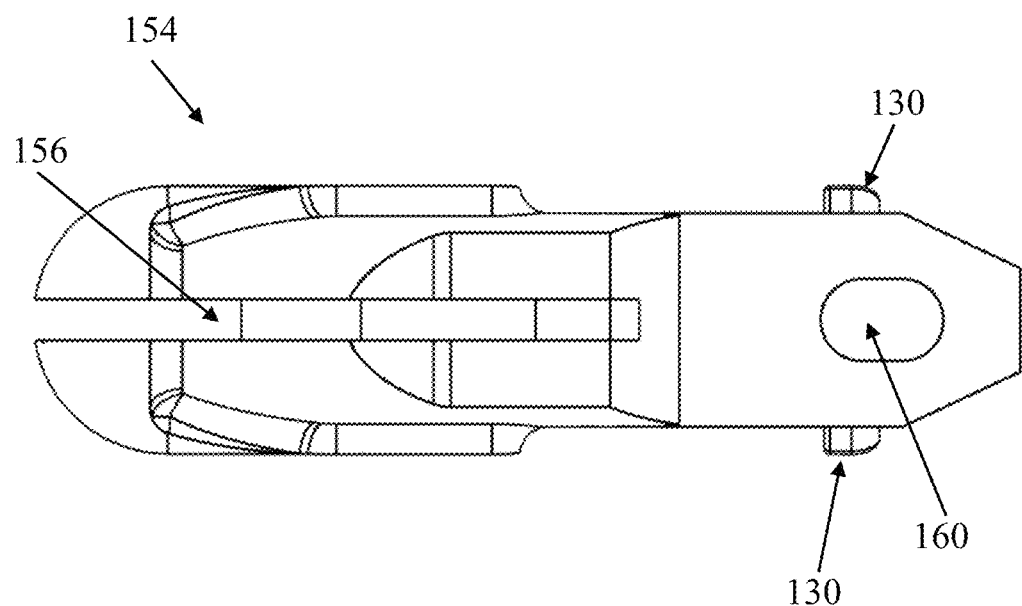
Figure 19I:
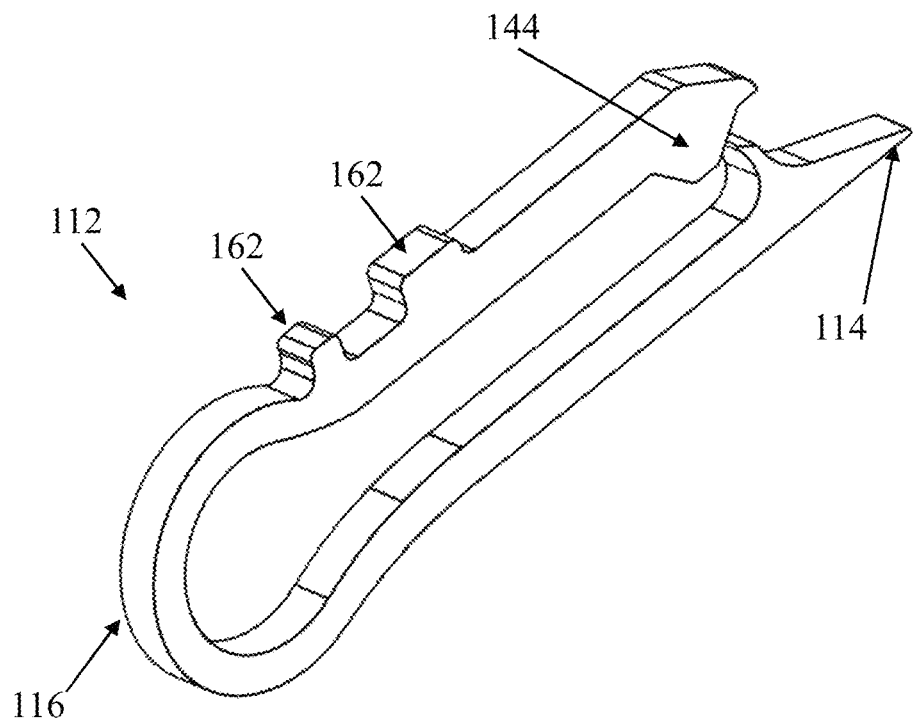
FIGS. 19I and 19J show various views of a distal tine of the distal arm of FIGS. 19A-19B.
Figure 19J:
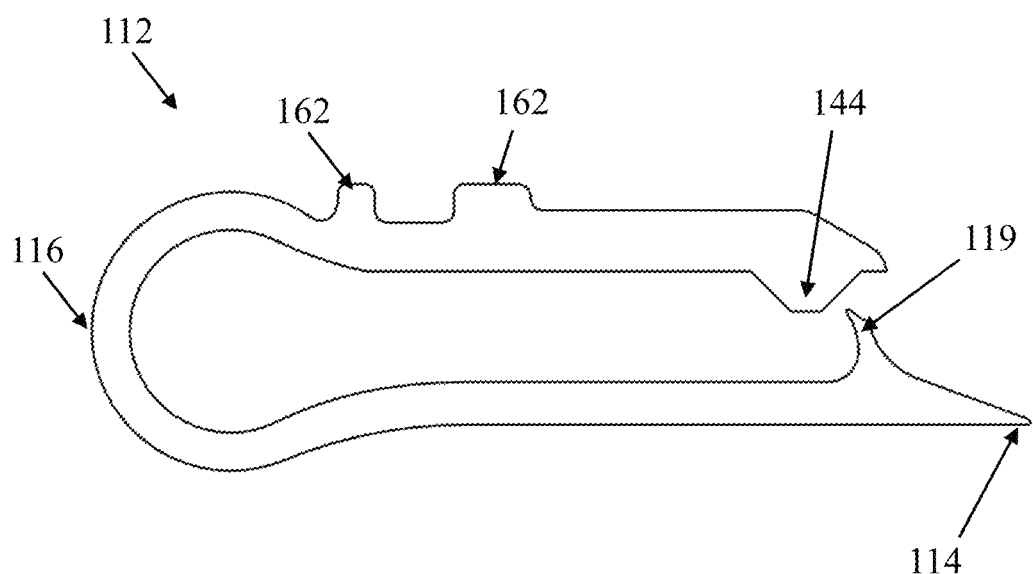
Figure 19K:
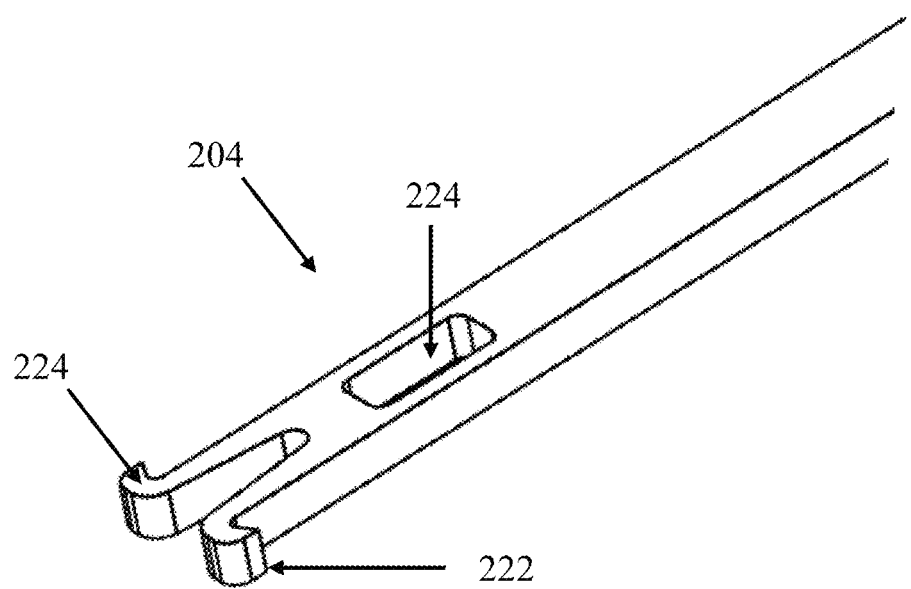
FIG. 19K is a perspective view of a distal portion of a drive element for use with the housing of FIGS. 19E-19H and the distal tine of FIGS. 19I-19J.
Figure 19L:
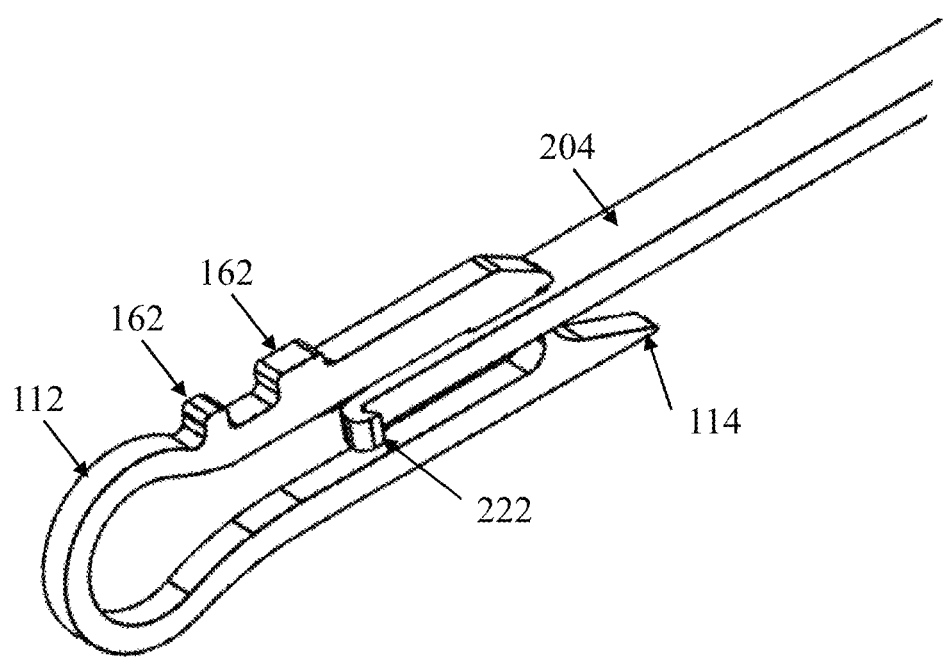
FIG. 19L is a perspective view of the drive element of FIG. 19K coupled with the distal tine of FIGS. 19I-19J.
Figure 19M:
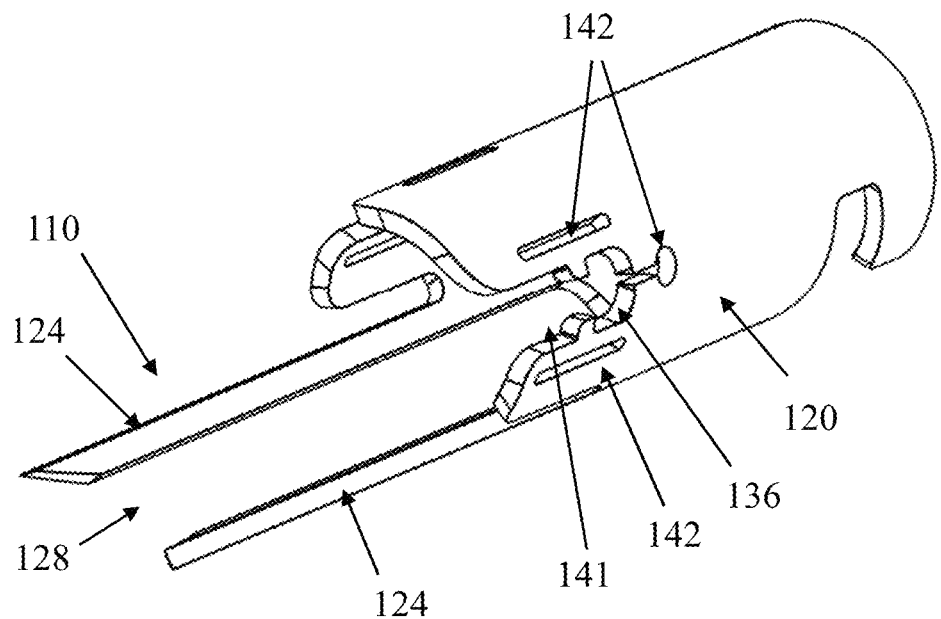
FIGS. 19M and 19N are top and bottom views of a coupler for use with the distal arm of FIGS. 19A-19B.
Figure 19N:
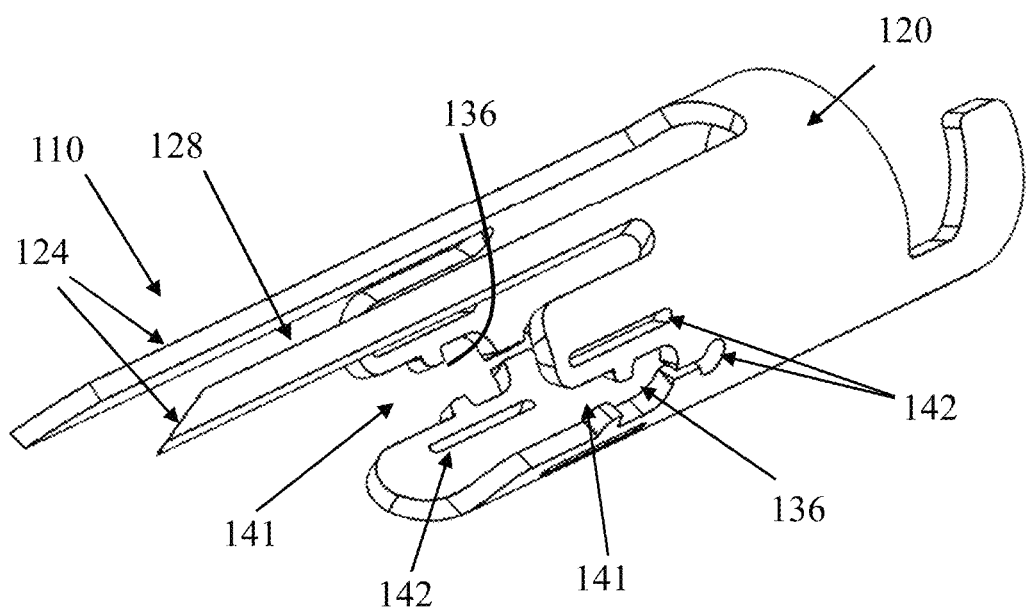
Figure 19O:
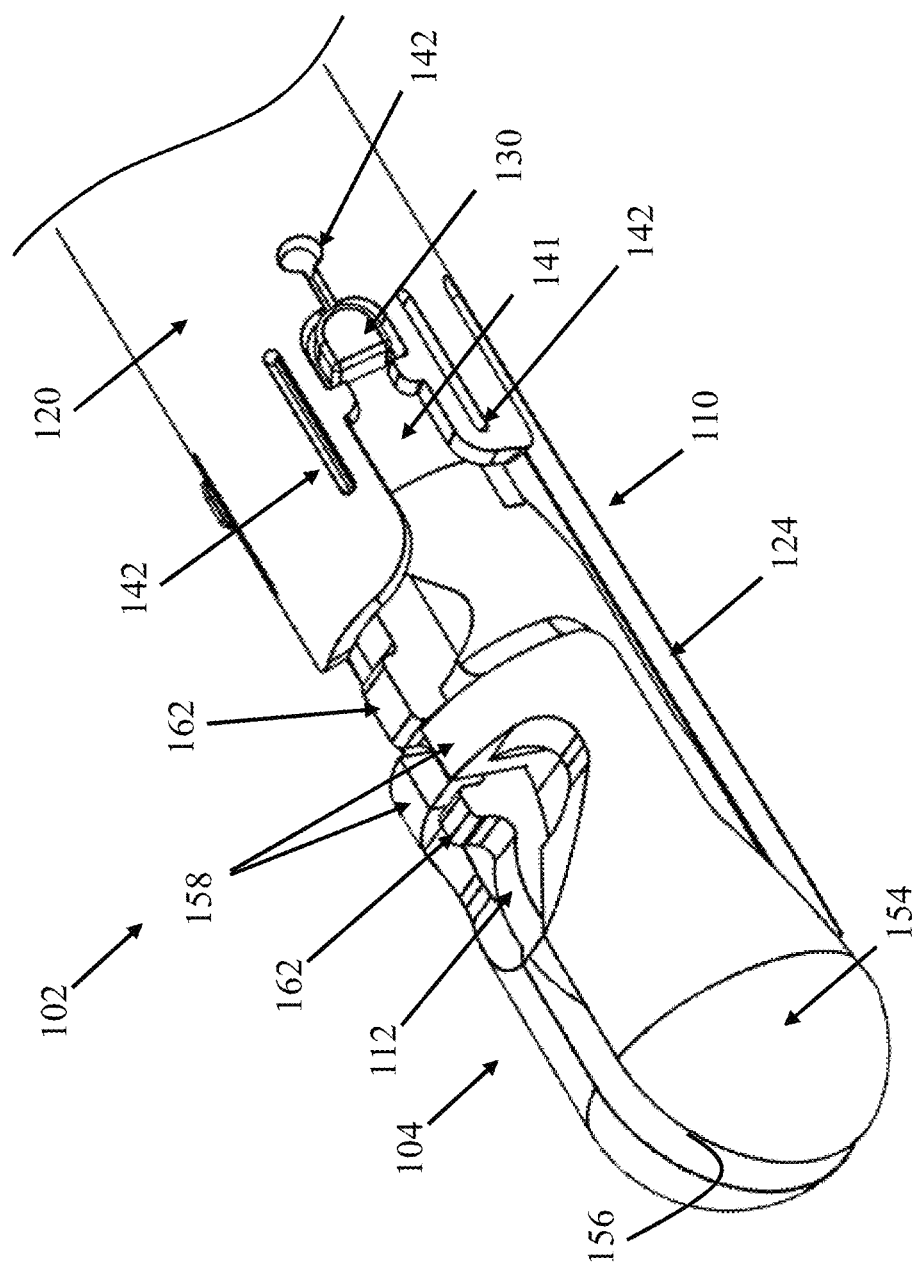
FIGS. 19O and 19P are top and bottom perspective views of the distal arm of FIGS. 19A-19B in a locked position with the coupler of FIGS. 19M and 19N.
Figure 19P:
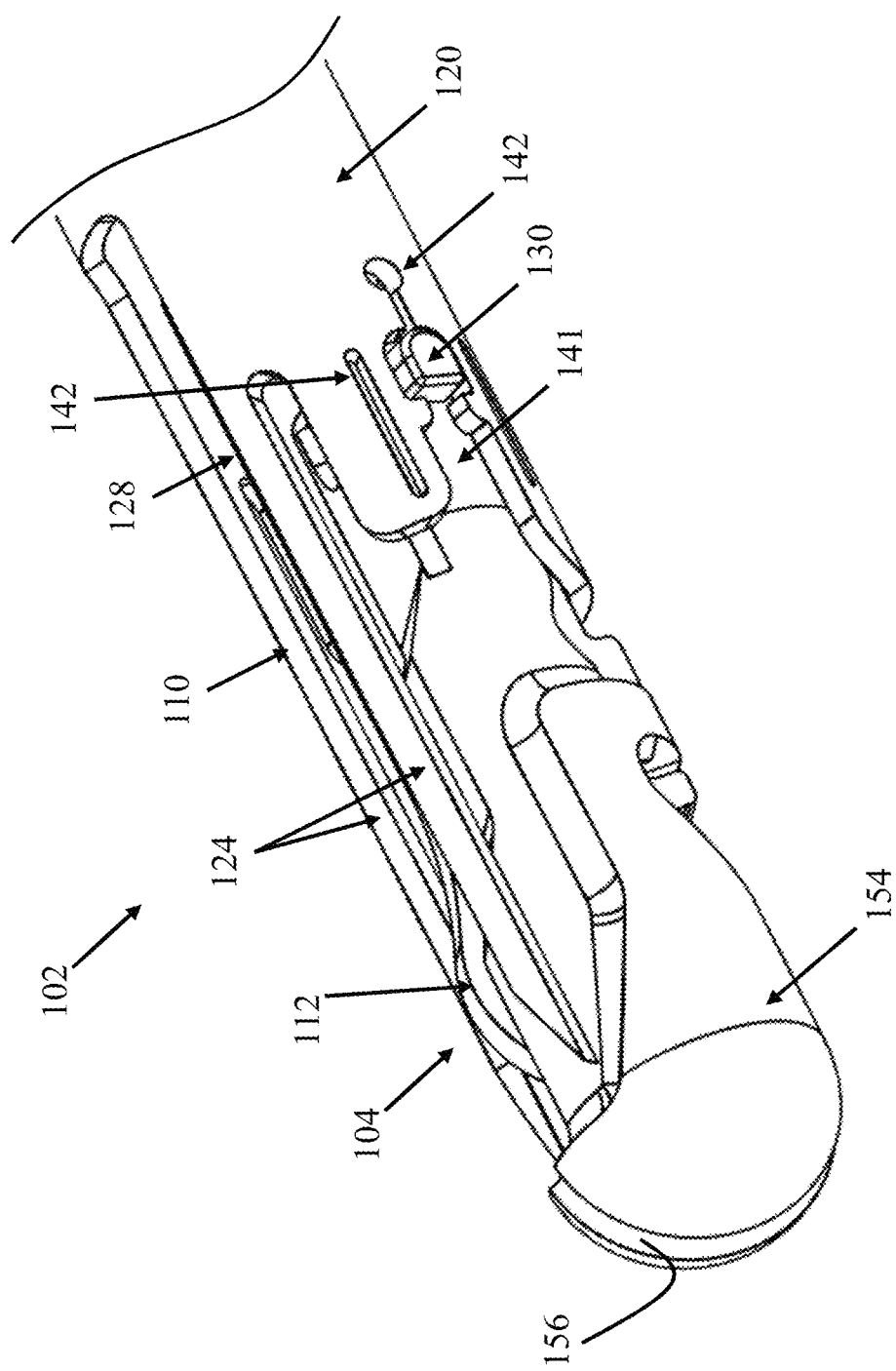

As shown in FIGS. 19A-19P, the housing 154 of the distal arm 104 includes a tine channel 156 operable to receive the distal tine 112 therein. The tine channel 156 may be substantially linear and extend around the top, front, and bottom of the housing 154 to substantially correspond to the shape of the distal tine 112. The tine channel 156 may be sized, shaped, and configured to receive at least a portion of the distal tine 112 therein. In some embodiments, the distal tine 112 is snap fit or press fit into the tine channel 156 to secure the distal tine 112 in the tine channel 156. Additionally or alternatively, the distal tine 112 may be secured in the tine channel 156 via welding, crimping, swaging, soldering, adhesives, fasteners, or the like.

The housing 154 may include one or more housing extensions 158 extending radially outwardly from and at least partially laterally across the tine channel 156. The housing extensions 158 may be sized, shaped, and configured to prevent the distal tine 112 from being retracted from the tine channel 156. For example, the housing extensions may be operable to abut an outer surface of the distal tine 112 disposed in the tine channel 156 to prevent the distal tine 112 from moving radially out of the tine channel 156. The housing extensions 158 may be crimped, swaged, pressed, or otherwise mechanically deformed such as to hold the distal tine 112 in place relative the housing 154 and within the tine channel 156.

The distal tine 112 may include one or more retaining tabs 162 extending radially outwardly from the remainder of the distal tine 112. The retaining tabs 162 may be disposed at a location along the distal tine 112 and extend outwardly from the remainder of the distal tine 112 to retain the distal tine 112 in the tine channel 156. The retaining tabs 162 may extend radially outwardly above a bottom surface of the housing extensions 158. The retaining tabs 162 may be sized, shaped, positioned, and configured to abut the proximal and distal sides of the housing extensions 158. The retaining tabs 162 may be disposed on both sides of the housing extensions 158 to prevent or otherwise restrict the distal tine 112 from translating linearly within the tine channel 156 relative to the housing 154.

The distal tine 112 and/or the housing 154 may be configured to releasably couple with the distal end of the drive element 204. As shown in FIG. 19K, the distal end of the drive element 204 may include a coupling area 224 proximally inset from the prongs 222. The coupling area 224 may be sized, shaped, and configured to receive a portion of the distal tine 112 and/or the housing 154 to releasably couple the distal arm 104 to the drive element 204 such that the position of the distal arm 104 may be controlled by the drive element 204.

As shown in FIGS. 19I and 19J, the coupling projection 144 of the distal tine 112 extends downwardly from the upper portion of the distal tine near the proximal end of the distal tine 112. The proximal and/or distal sides of the coupling projection 144 may be sloped or rounded, such as to permit the coupling projection 144 to be withdrawn from the coupling area 224 defined by the drive element 204, as described below.

As shown in FIGS. 19C and 19D, the coupling projection 144 may extend into the coupling area 224 defined by the drive element 204 to couple the distal arm 104 with the drive element 204. The coupling projection 144 may extend substantially from the proximal end of the coupling area 224 to the distal end of the coupling area 224 such that the movement of the drive element 204 is translated to the distal arm 104.

The distal arm 104 may be decoupled from the drive element 204 by applying sufficient proximal force to the drive element 204 to withdraw the coupling projection 144 from the coupling area 224, such as after the tissue clipping assembly 102 has been moved to the closed and locked positions. The drive element 204 may be proximally retracted such that the distal end of the coupling projection 144 contacts the distal side of the coupling area 224. The side of the coupling projection 144 may be sized, shaped, and configured such that the distal tine 112 moves upwardly by virtue of the contact between the distal of the coupling projection 144 and the distal side of the coupling area 224 as the drive element 204 is proximally retracted. In the illustrated embodiment, the sides of the coupling projection 144 are angled or sloped. However, it will be appreciated that the coupling projection 144 may have other shapes and configurations. For example, the sides of the coupling projection 144 may be rounded. The drive element 204 may be proximally retracted such that the coupling projection 144 is lifted out of the coupling area 224. The drive element 204 may be decoupled from the distal arm 104 when the coupling projection 144 is removed from the coupling area 224 and the drive element 204 is proximally retracted.

While the distal tine 112 has been described as releasably coupling with the distal end of the drive element 204, it will be understood that the distal arm 104 may have other configurations and assemblies. For example, the coupling projection 144 may be disposed on the housing 154 to be operably received in the coupling area 224 defined by the drive element 204.

In some embodiments, the housing 154 also includes a lateral passage 160 near the proximal end of the housing 154. The lateral passage 160 may be sized, shaped, and configured to at least partially receive one of the barbs 119 of the distal tine 112 therethrough. The disposition of the barb 119 in the lateral passage 160 may permit the distal tine 112 to substantially close in the tine channel 156 of the housing 154.

As shown in FIGS. 19A-19C and 19E-19H, the locking projections 130 of the distal arm 104 may be disposed on the outer surface of the housing 154, such as at a proximal end of the housing 154. As shown in FIGS. 19M-19O, the housing 154 may be retracted into and locked with the collar 120, such as when the tissue clipping assembly 102 is moved to the closed and locked positions. The collar 120 includes setting recesses 141 at a distal end of the collar 120 and extending into the receiving portions 136. The setting recesses 141 and receiving portions 136 may be positioned corresponding to the position of the locking projections 130 of the housing 154. The distal arm 104 may be retracted such that the locking projections 130 are disposed in the setting recesses 141, such as to orient the distal arm 104 and ensure the tissue clipping assembly 102 is properly clipping tissue.

The distal arm 104 may be proximally retracted, such as via the drive element 204, to move the locking projections 130 into the receiving portions 136 of the collar to move the distal arm 104 to the closed and locked positions. The collar 120 may also include stress reliefs 142 disposed on both sides of the setting recesses 141 and the receiving portions 136 and at the distal end of the receiving portions 136 to permit the locking projections 130 to move from the setting recesses 141 to the receiving portions 136 of the collar 120. In some embodiments, as shown in FIG. 19P, the distal tine 112 may be disposed between the proximal tines 124 of the proximal arm 110 as the distal arm 104 is retracted such that the proximal tines 124 operate as the guiding slot 140.

As shown in FIGS. 19O and 19P, the housing 154 may substantially surround the proximal tines 124 of the proximal arm 110 when the tissue clipping assembly 102 is in the closed and locked positions. The housing 154 may be sized, shaped, and configured to maintain the clipping of tissue between the distal and proximal arms 104, 110 and to reduce trauma to surrounding tissue when the tissue clipping assembly 102 is in the closed and locked positions.

Figure 20A:
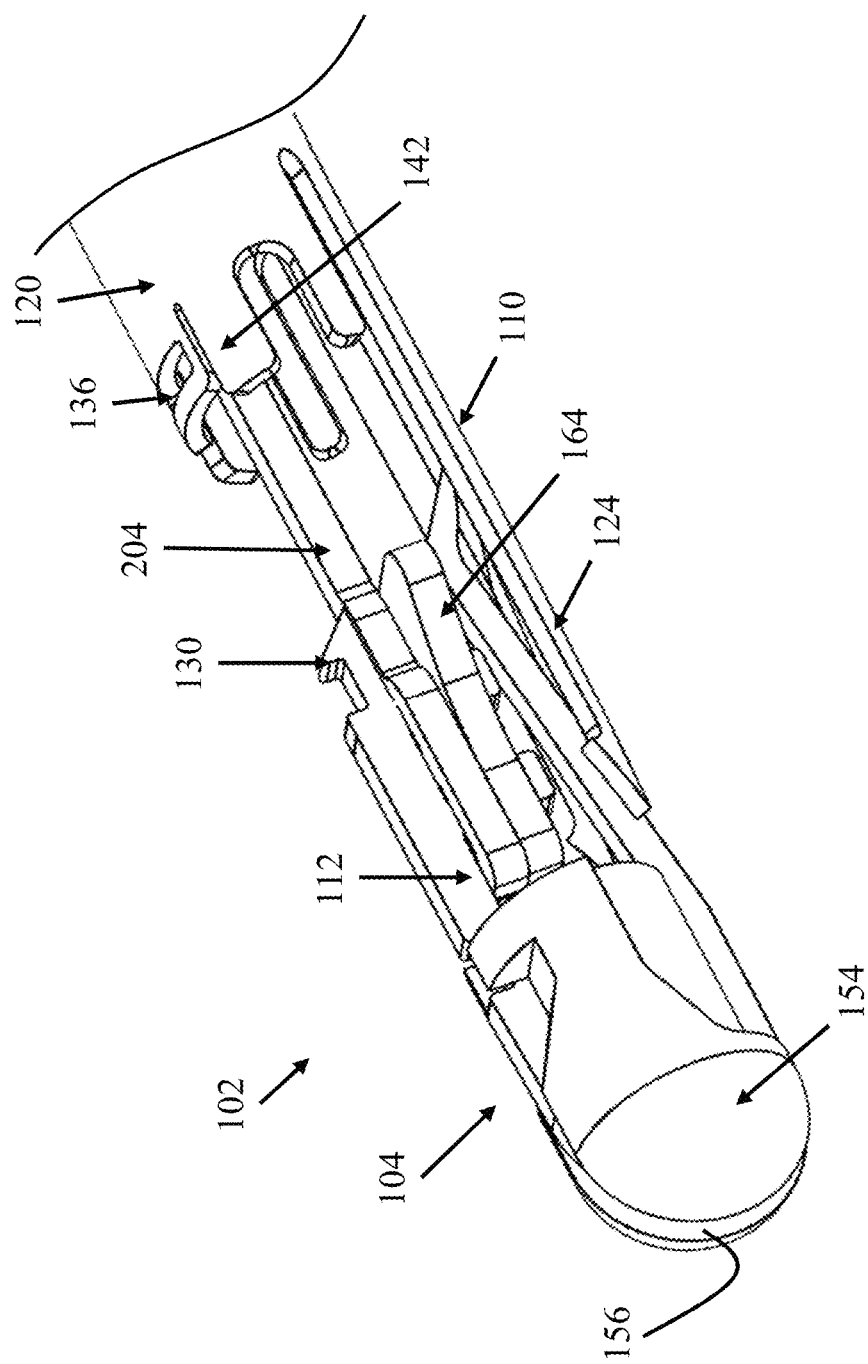
FIG. 20A is a perspective view of a distal arm with a housing according to another embodiment.
Figure 20B:
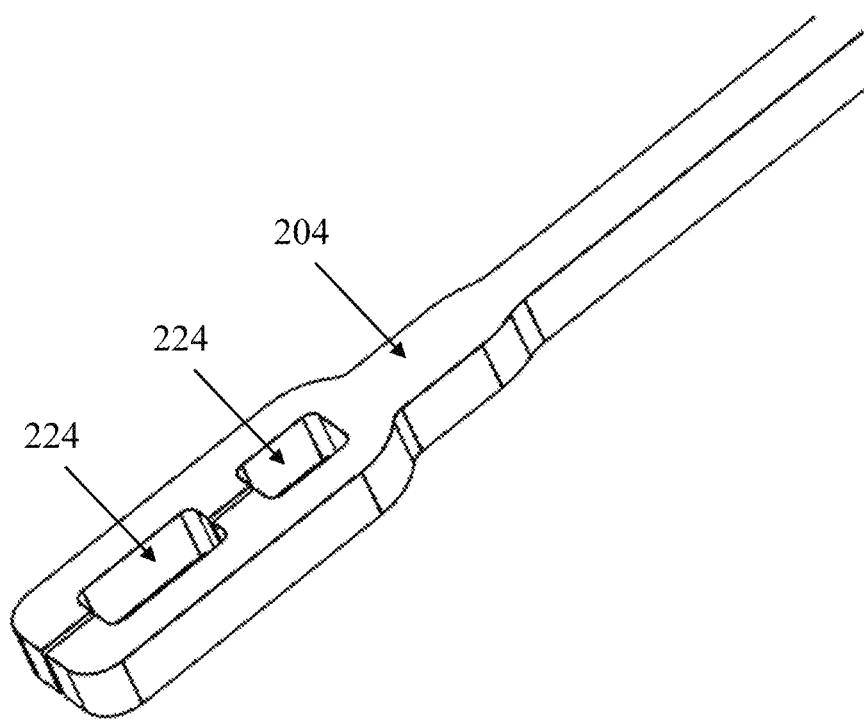
FIG. 20B is a perspective view of a distal portion of a drive element for use with the housing of FIG. 20A.
Figure 20C:
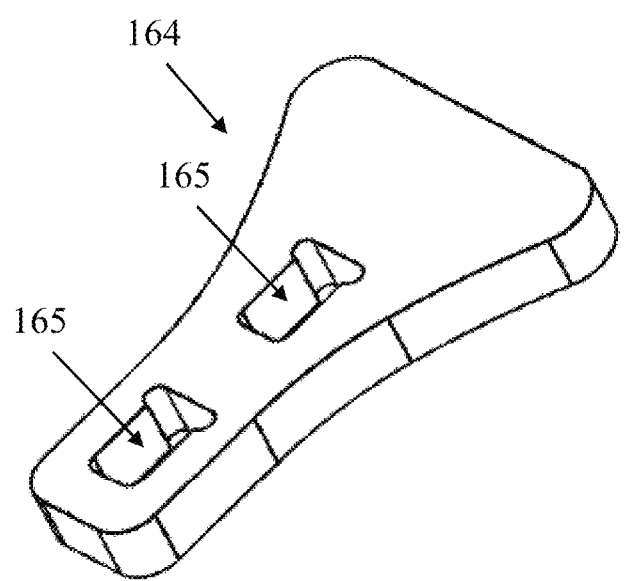
FIG. 20C is a perspective view of a housing coupler for use with the housing of FIG. 20A.
Figure 20D:
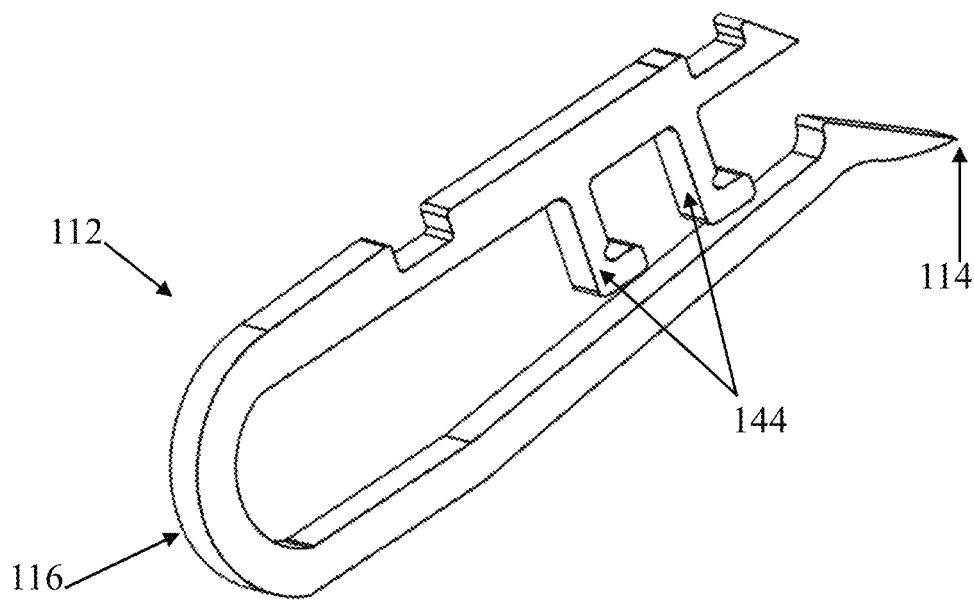
FIG. 20D is a perspective view of a distal tine for use with the housing of FIG. 20A.

As shown in FIGS. 20A-20E, the housing 154 may include a drive coupler 164 configured to further couple the distal arm 104 with the drive element 204. As shown in FIG. 20B, the drive element 204 may define one or more coupling areas 224 along the distal end of the drive element 204. As shown in FIG. 20C, the drive coupler 164 may be substantially triangular with a wider proximal end and include one or more projection apertures 165 extending from a top of the drive coupler 164 to a bottom of the drive coupler 164. The projection apertures 165 may substantially correspond to the position of the coupling areas 224 of the drive element 204. As shown in FIG. 20D, the distal tine 112 includes one or more coupling projections 144 extending substantially downwardly. The coupling projections 144 may be sized and positioned corresponding to the coupling areas 224 of the drive element 204 and the projection apertures 165 of the drive coupler 164. The coupling projections 144 may be substantially L-shaped with the elongated portion extending proximally.

Figure 20E:
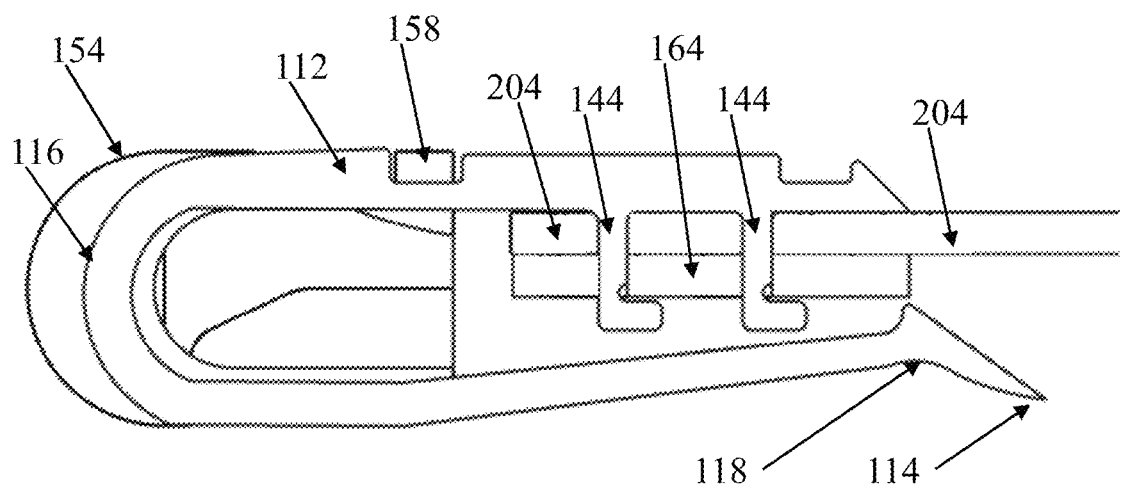
FIG. 20E is a cross-sectional side view of the housing of FIG. 20A.

As shown in FIG. 20E, when the distal tine 112 is coupled with the housing 154, the coupling projections 144 may extend through the coupling areas 224 of the drive element 204 and the projection apertures 165 of the drive coupler 164 to couple the distal arm 104 to the drive element 204. The elongated portion of the coupling projections 144 may partially extend along the bottom surface of the drive coupler 164, such as to prevent the drive coupler 164 from sliding off the coupling projections 144. The drive coupler 164 may maintain the coupling of the drive element 204 and the distal arm 104 by preventing the drive element 204 from prematurely sliding off the coupling projections 144. When the tissue clipping assembly 102 is moved to the closed and locked positions, the drive element 204 may be manipulated such that the coupling projections 144 are retracted through the drive coupler 164 and the drive element 204 to decouple the drive element 204 from the distal arm 104.

Further, it will be understood that the distal tine 112 may have a variety of configurations to maintain the distal tine 112 in the tine channel 156. For example, as shown in FIGS. 20D-20E, the top portion of the distal tine 112 may include a notch to receive the housing extension 158 therein. The disposition of the housing extension 158 in the notch may maintain the translational position of the distal tine 112 relative to the tine channel 156 and may prevent the distal tine 112 from moving radially out of the tine channel 156.

Figure 21A:
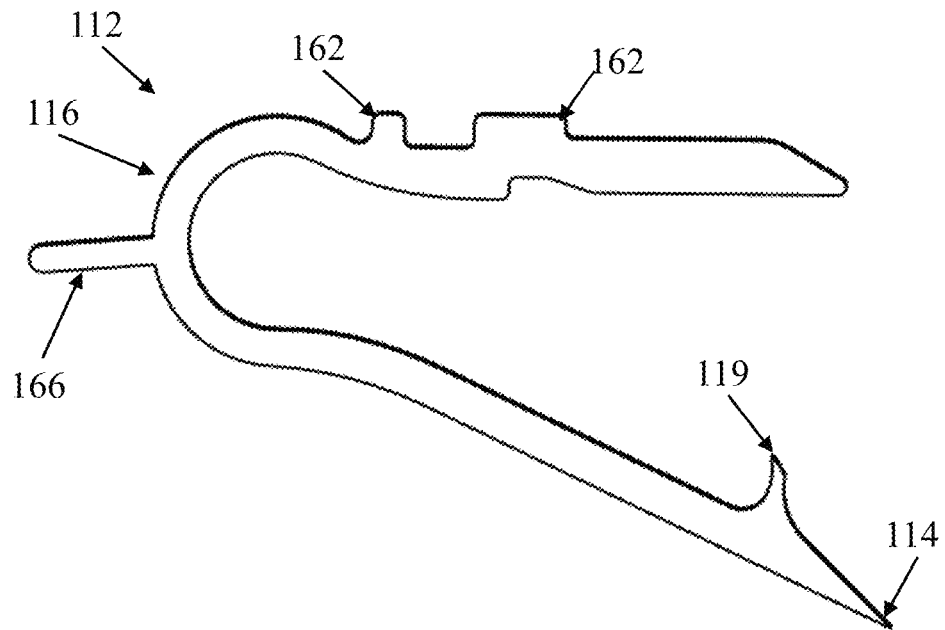
FIG. 21A is a side view of a distal tine for use with a housing according to one embodiment.
Figure 21B:
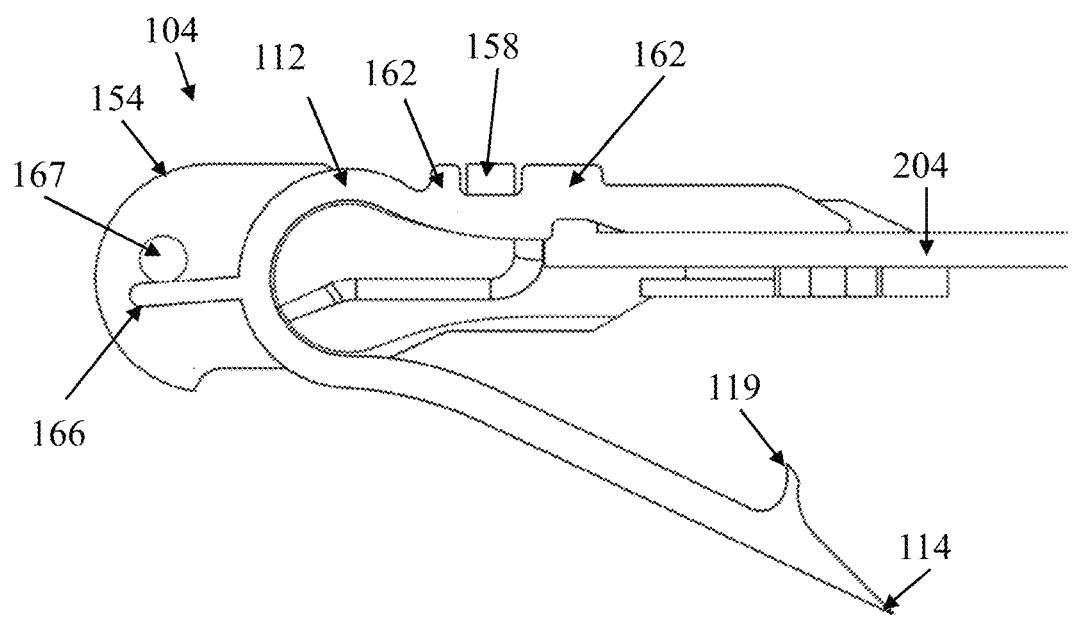
FIG. 21B is a cross-sectional side view of the distal tine of FIG. 21A coupled with a housing.

In some embodiments, the distal arm 104, such as the housing 154, may be sized, shaped, and configured to limit the flexing or rotation of the one or more distal tines 112, such as to limit the flexing or rotation of the distal tine 112 about the rounded portions 116 of the distal tines 112. As shown in FIGS. 21A and 21B, the distal tine 112 may include a flange 166 extending radially outwardly (e.g., proximally) from the rounded portion 116. The housing 154 may include a stop 167 radially outward (e.g., proximal) from the tine channel 156. As the bottom portion of the distal tine 112, such as the tip 114, flexes downwardly, such as into tissue, the flange 166 may abut the stop 167. The abutment between the flange 166 and the stop 167 may prevent the bottom portion of the distal tine 112, such as the tip 114, from flexing further downward. For example, the abutment between the flange 166 and the stop 167 may prevent the distal tine 112 from opening beyond a point from which the distal tine 112 cannot return to a closed position to clip tissue. Additionally or alternatively, the rounded portion 116 of the distal tine 112 may be thicker and/or comprise a stiffer material to prevent the distal tine 112 from opening too far. Further, the housing 154 may include one or more housing extensions 158 extending across the tine channel 156 at a bottom side of the housing 154 to similarly prevent the distal tine 112 from opening too far during the tissue clipping operation.

Figure 22A:
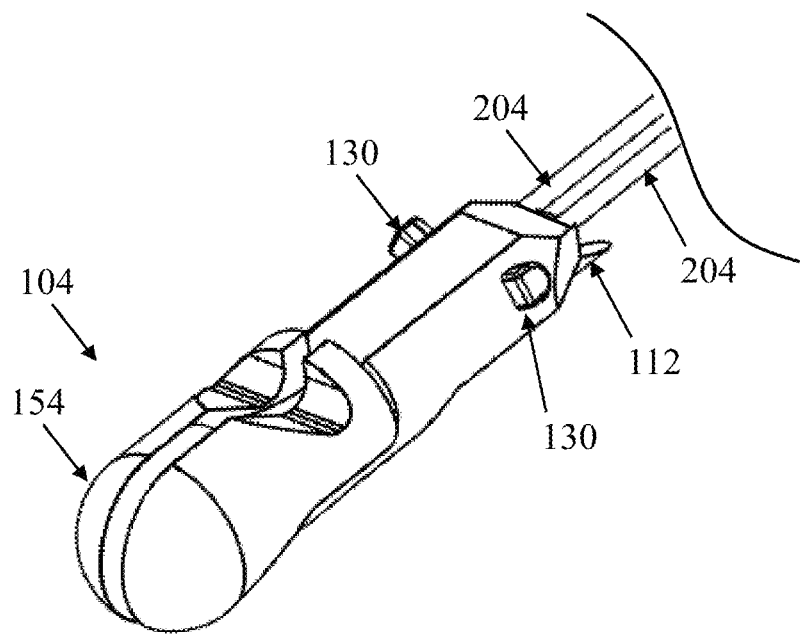
FIG. 22A is a perspective view of a distal arm according to another embodiment.
Figure 22B:
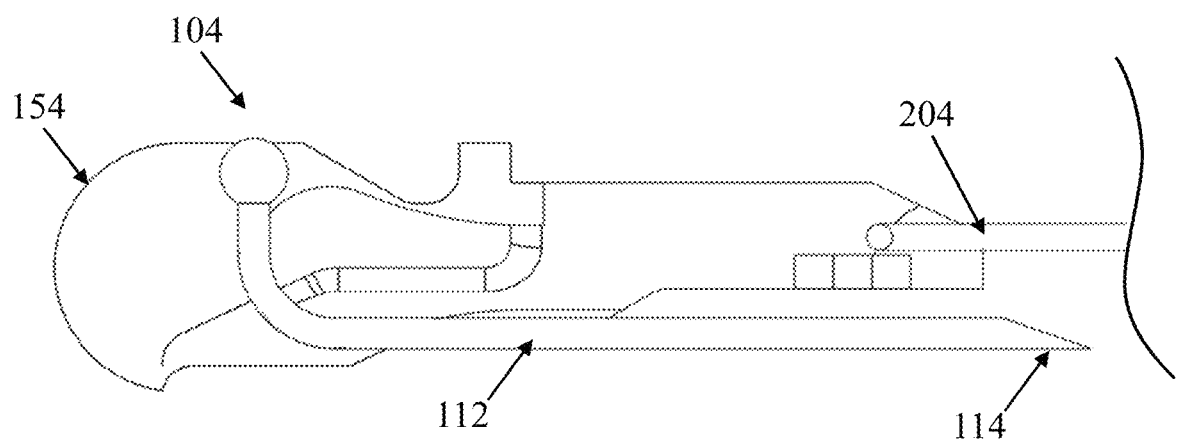
FIG. 22B is a cross-sectional view of the distal arm of FIG. 22A.

In some embodiments, the distal arm 104 and/or the drive element 204 may be configured to simplify the device 100 and/or to reduce the overall cost of the device 100. As shown in FIGS. 22A and 22B, the distal arm 104 may include a single bent distal tine 112. In some embodiments, the distal tine 112 may be a bent and cut tube or Nitinol wire. The distal tine 112 may have a spherical end which is secured in the housing 154. The housing 154 may be coupled with the distal end of the drive element 204, such as via a frangible coupling. The distal end of the drive element 204 may comprise two or more wires, such as stainless steel or Nitinol wires, instead of a single element with a substantially rectangular cross section, as described in more detail below.

While the housing 154 has been described as housing one distal tine 112, it will be understood that the housing 154 may have other configurations. For example, the housing 154 may include two or more tine channels 156 such that the housing 154 may be used with two or more distal tines 112. Further, any of the housings 154 may be used with any of the other distal tines 112 described herein, such as the distal tines of FIG. 8A-8B.

Referring now to FIGS. 23-32, the collar 120 of the tissue clipping assembly 102 may be operably coupled with the catheter such that the collar 120 may be decoupled from the catheter 212, such as after the tissue clipping assembly 102 clips tissue. The distal end of the catheter 212 may be coupled directly or indirectly with the proximal end of the collar 120 during operation. The catheter 212 may be decoupled from the collar 120 after the tissue clipping assembly 102 has been moved to the closed position, such as via continued proximal retraction of the drive element 204.

Figure 23:
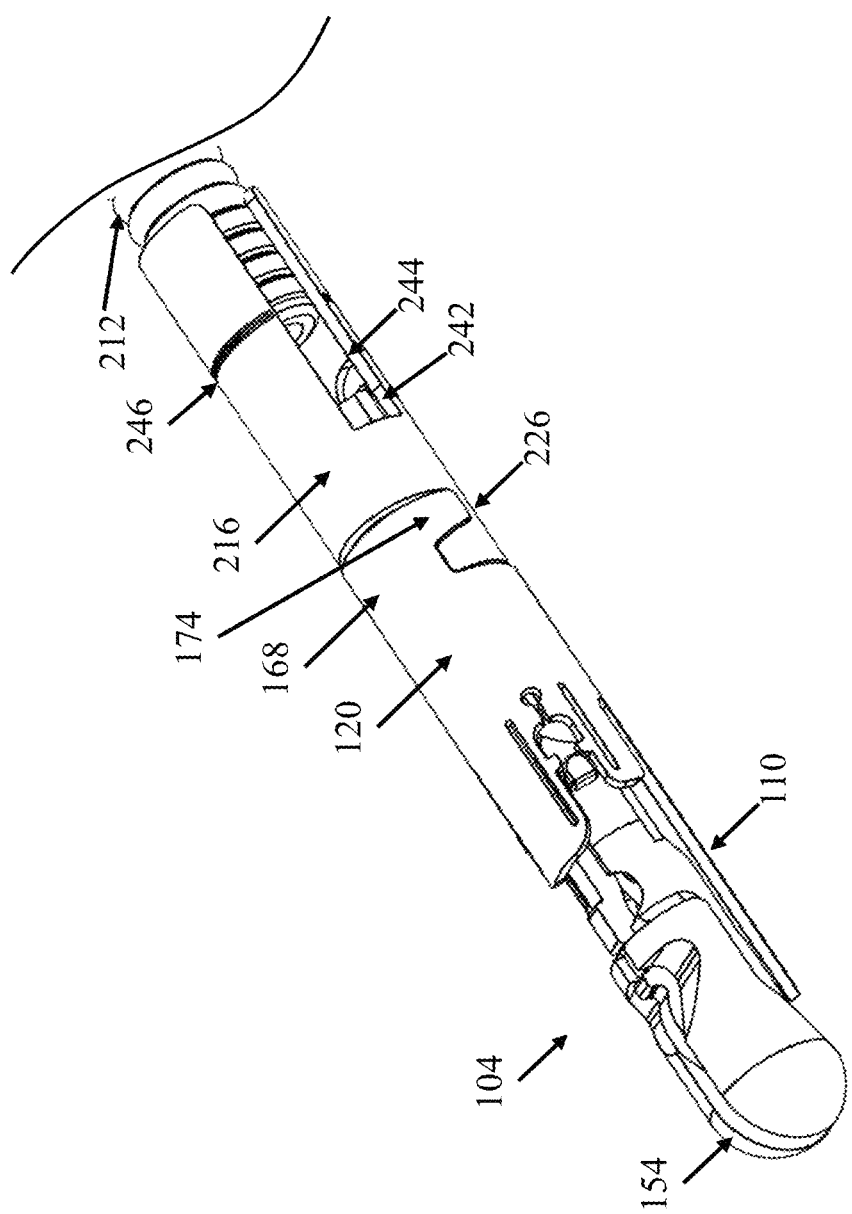
FIG. 23 is a perspective view of a tissue clipping assembly coupled with a catheter according to one embodiment.
Figure 24A:
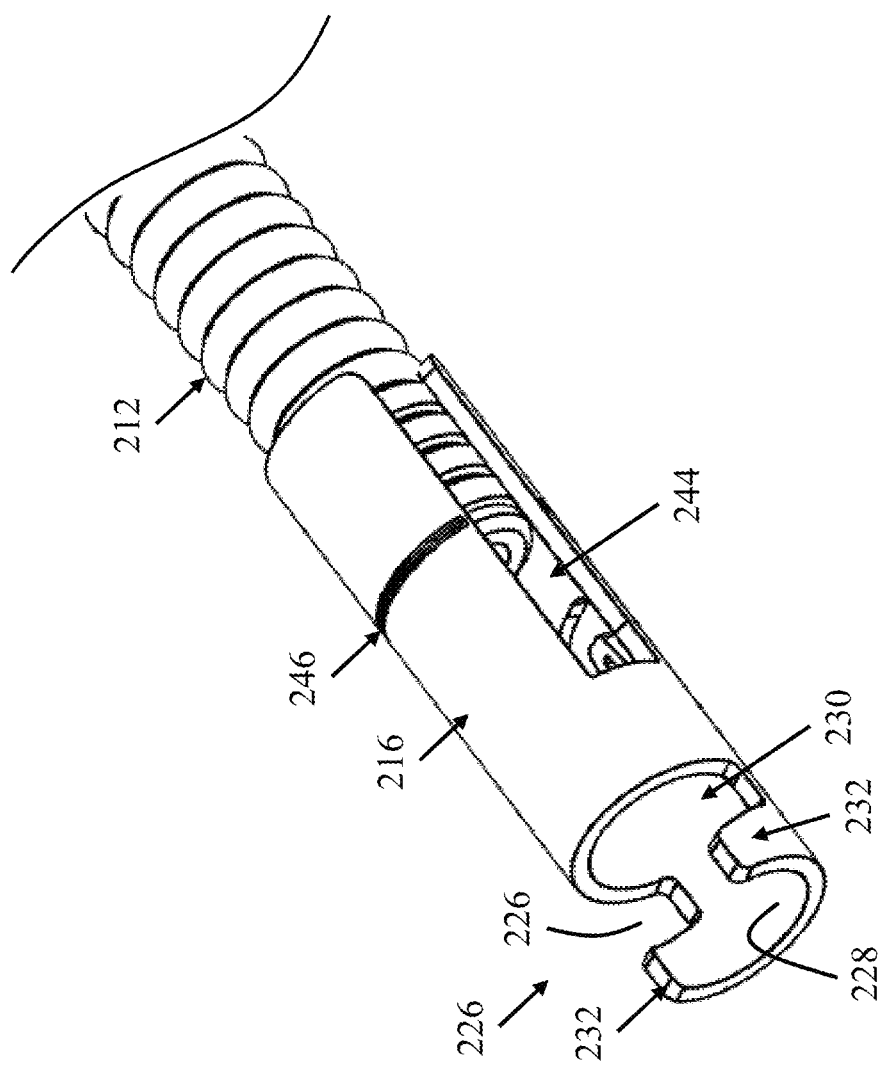
FIGS. 24A and 24B are top and bottom perspective views of the catheter of FIG. 23 coupled with a connector.

As shown in FIG. 23-24, the drive assembly 200 may include a connector 216 configured to operably couple the distal end of the catheter 212 with the proximal end of the collar 120. The connector 216 may couple the catheter 212 with the collar 120 while the tissue clipping assembly 102 is maneuvered to clip tissue. The connector 216 may also decouple the catheter 212 from the collar 120 after the tissue clipping assembly 102 has been moved to the closed and locked positions, such as to deploy the tissue clipping assembly 102 in the body to maintain the clipping of the tissue. The connector 216 may be a substantially hollow cylinder operable to slidably receive the drive element 204 therethrough.

In some embodiments, the proximal end of the connector 216 is fixed to the distal end of the catheter 212 such that the connector 216 remains coupled with the catheter 212 after the drive assembly 200 is decoupled from the tissue clipping assembly 102. The proximal end of the connector 216 may be coupled to the distal end of the catheter 212 via adhesives, welding, fasteners, heat bonding, or the like. In an exemplary embodiment, the proximal end of the connector 216 is welded to the distal end of the catheter 212. In other embodiments, the connector 216 is included as an integral part of the distal portion of the catheter 212.

The distal end of the connector 216 is operable to couple with the proximal end of the collar 120. As shown in FIG. 23-25B, the connector 216 includes a connecting portion 226 at a distal end of the connector 216 operable to couple with the collar 120. The connecting portion 226 of the connector 216 includes one or more connecting projections 228 and defines one or more receiving areas 230. The connecting projections 228 of the collar 120 may extend distally from the remainder of the connector 216 and may be substantially arcuate.

The collar 120 may also include a connecting portion 168 at a proximal end of the collar 120 operable to couple with the connecting portion 226 of the connector 216. The connecting portion 168 of the collar 120 may also include one or more connecting projections 170 and define one or more receiving areas 172. The connecting projections 170 of the collar 120 may extend proximally from the remainder of the collar 120 and may be substantially arcuate.

The connecting projections 170 of the collar 120 and the receiving areas 230 defined by the connector 216 may be sized, shaped, and configured such that the connecting projections 170 of the collar 120 may be received in the receiving areas 230 of the connector 216 to couple the collar 120 with the connector 216. The connecting projections 228 of the connector 216 and the receiving areas 172 defined by the collar 120 may also be sized, shaped, and configured such that the connecting projections 228 of the connector 216 may be received in the receiving areas 172 of the collar 120 to couple the collar 120 with the connector 216. The connecting projections 170 of the collar 120 may be received in the receiving areas 230 of the connector 216 and the connecting projections 228 of the connector 216 may be received in the receiving areas 172 of the collar 120 to operably couple the collar 120 to the connector 216. The connecting projections 170 and receiving areas 172 of the collar 120 and the connecting projections 228 and the receiving areas 230 of the collar 120 may operably interlock together to operably couple the collar 120 with the connector 216. The connecting portion 168 of the collar 120 may linearly overlap with the connecting portion 226 of the connector 216 when the connector 216 is coupled with the collar 120. For example, the connecting projections 170 of the collar 120 may extend proximally beyond a portion of the connecting projections 228 of the connector 216 and connecting projections 228 of the connector 216 may extend distally beyond a portion of the connecting projections 170 of the collar 120 when the connector 216 is coupled with the collar 120. The collar 120 may be translated and/or rotated with the catheter 212 when the collar 120 is coupled with the connector 216.

The connecting projections 170 of the collar 120 may each include lateral flanges 174 extending laterally (e.g., radially) from the proximal end of the connecting projection 170. The lateral flanges 174 of the collar 120 may be operable to retain the connecting projection 170 in the corresponding receiving area 230 of the connector 216 during operation. The lateral flanges 174 of the connecting projections 170 of the collar 120 may be sized, shaped, and configured to be received in the receiving areas 230 of the connector 216 and to laterally (e.g., radially) extend proximally behind a portion of the connector 216. The extension of the lateral flanges 174 of the connecting projections 170 of the collar 120 proximally behind a portion of the connector 216 may operably interlock the collar 120 with the connector 216 and prevent the collar 120 from moving distally relative to the connector 216.

The connecting projections 228 of the connector 216 may also include lateral flanges 232 extending laterally from the distal end of the connecting projections 228. The lateral flanges 232 of the connector 216 may be operable to retain the respective connecting projection 228 in the corresponding receiving area 172 of the collar 120 during operation. The lateral flanges 232 of the connecting projections 228 of the connector 216 may be sized, shaped, and configured to be received in the receiving areas 172 of the collar 120 and to laterally (e.g., radially) extend distally behind a portion of the collar 120. The extension of the lateral flanges 232 of the connecting projections 228 of the connector 216 distally behind a portion of the collar 120 may operably interlock the connector 216 with the collar 120 and prevent the connector 216 from moving proximally relative to the collar 120.

In some embodiments, the lateral flanges 174 of the connecting projections 170 of the collar 120 are disposed proximally behind the lateral flanges 232 of the connecting projections 228 of the connector 216 when the connecting projections 170 of the collar 120 are disposed in the receiving areas 230 of the connector 216. The lateral flanges 232 of the connecting projections 228 of the connector 216 may be disposed distally behind the lateral flanges 174 of the connecting projections 170 of the collar 120 when the connecting projections 228 of the connector 216 are disposed in the receiving areas 172 of the collar 120. The linear overlap of the lateral flanges 174 of the collar 120 and the lateral flanges 232 of the connector 216 may further secure the coupling between the connector 216 and the collar 120.

In the illustrated embodiment, the collar 120 and the connector 216 have one connecting projection 170, 228 and two receiving areas 172, 230. However, it will be understood that the collar 120 and the connector 216 may have any suitable number of connecting projections 170, 228 and receiving areas 172, 230 to operably interlock the collar 120 with the connector 216.

The connecting projections 170 of the collar 120 may be decoupled from the receiving areas 230 of the connector 216 and the connecting projections 228 of the connector 216 may be decoupled from the receiving areas 172 of the collar 120 to decouple the connector 216 from the collar 120. The connecting projections 170 of the collar 120 may be moved laterally and/or flexed radially outwardly from the receiving areas 230 of the connector 216 and the connecting projections 228 of the connector 216 may be moved laterally and/or flexed radially outwardly from the receiving areas 172 of the collar 120. For example, connecting projections 228 of the connector 216 and/or the connecting projections 170 of the collar 120 may be moved or flexed radially outwardly via sufficient proximal retraction of the drive element 204, as described below. After the connecting projections 170 of the collar 120 are removed from the receiving areas 230 of the connector 216 and the connecting projections 228 of the connector 216 are removed from the receiving areas 172 of the collar 120, the connector 216 may be decoupled from the collar 120. After the connector 216 is decoupled from the collar 120, the connector 216 and the catheter 212 may be withdrawn from the collar 120.

While the catheter 212 has been described as being releasably coupled to the collar 120 via the connector 216, it will be understood that the catheter 212 may be coupled with the collar 120 in other manners. For example, the connector 216 may be incorporated into the distal end of the catheter 212 and the catheter 212 may include a coupling portion operable to connect with the connecting portion 168 of the collar 120.

Figure 26:
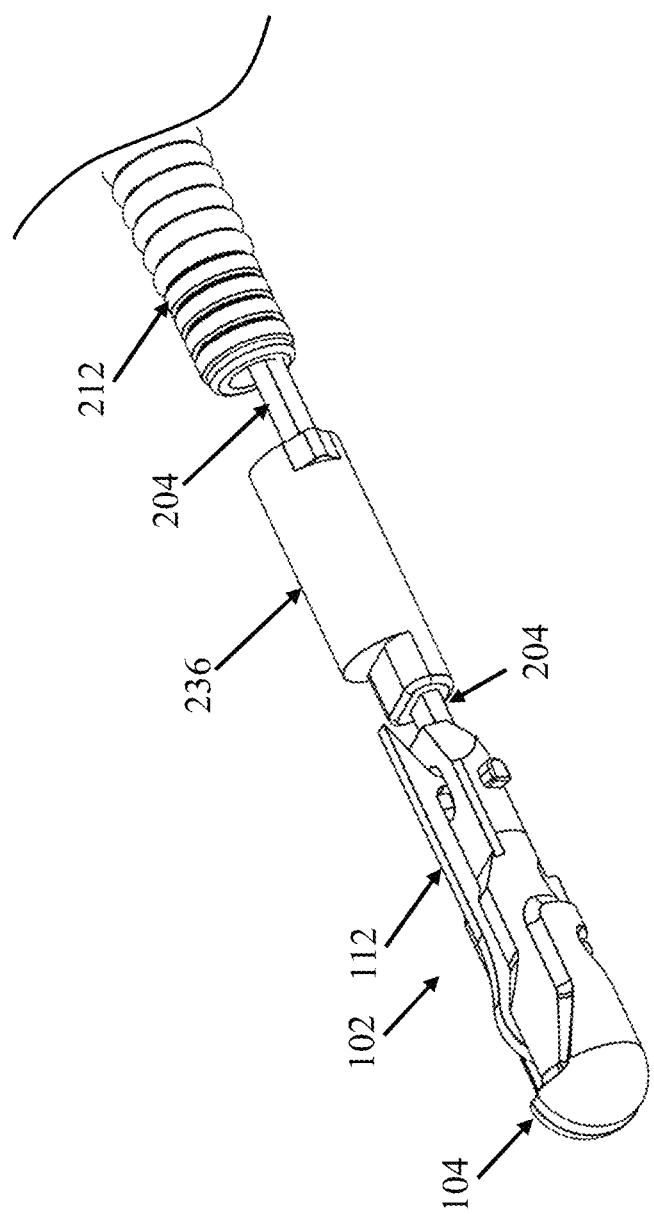
FIG. 26 is a bottom perspective view of the tissue clipping assembly of FIG. 23 with the collar and connector removed.
Figure 27A:
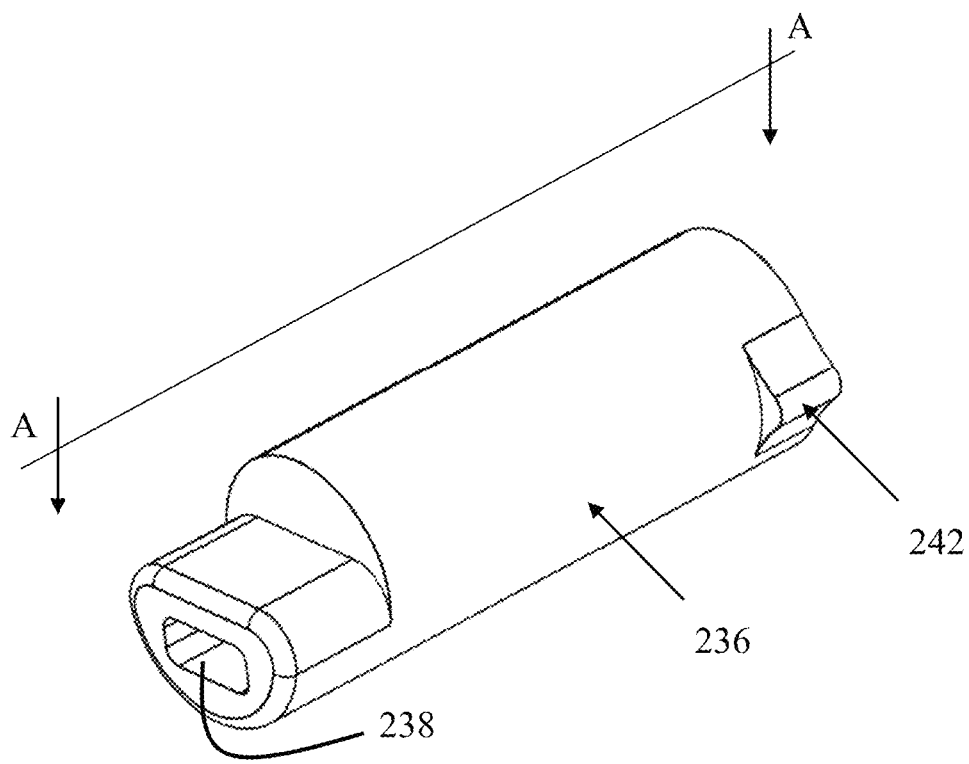
FIGS. 27A and 27B are front and rear perspective views of an alignment spacer for use with the tissue clipping assembly of FIG. 23.
Figure 27B:
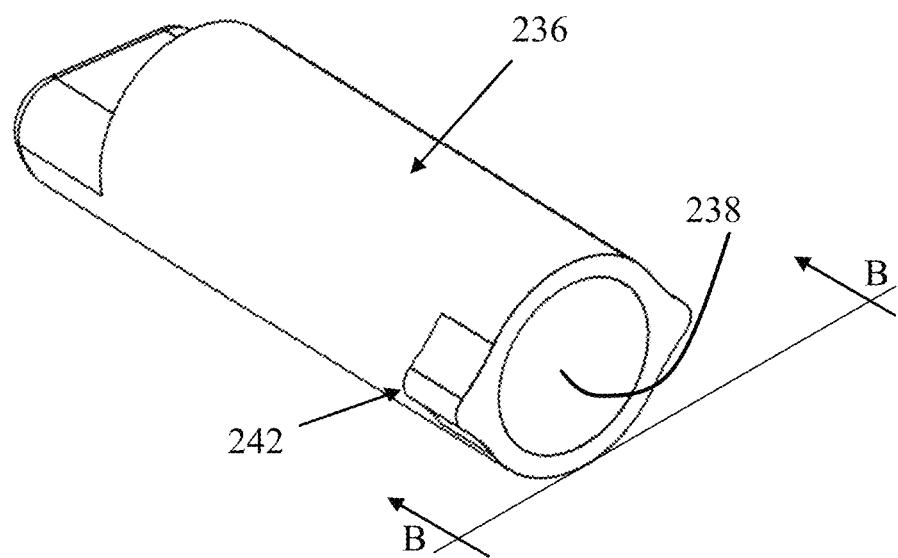
Figure 27C:
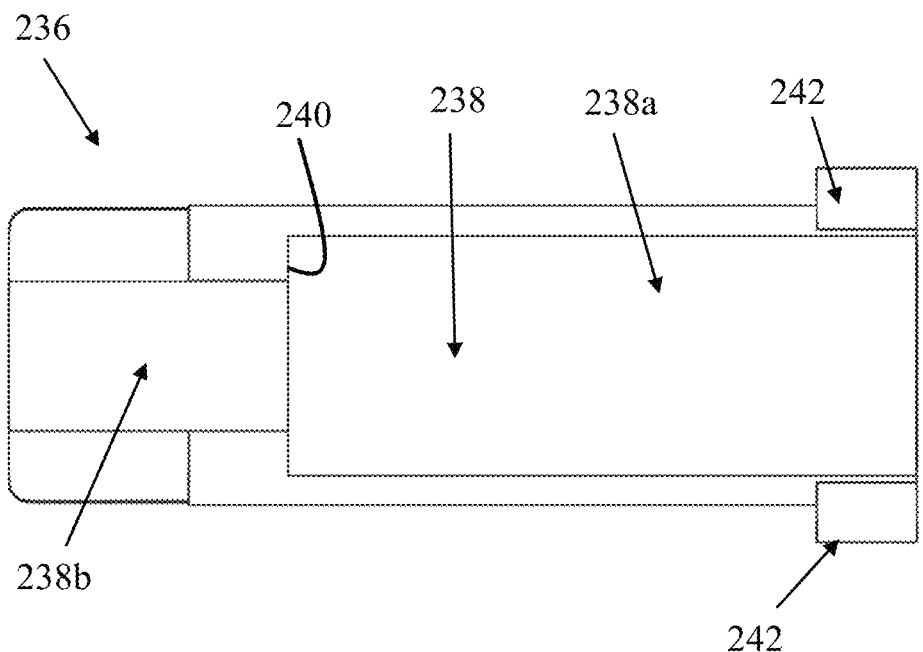
FIG. 27C is a cross-sectional view of the alignment spacer of FIGS. 27A-27B taken along the line B-B of FIG. 27B.
Figure 27D:
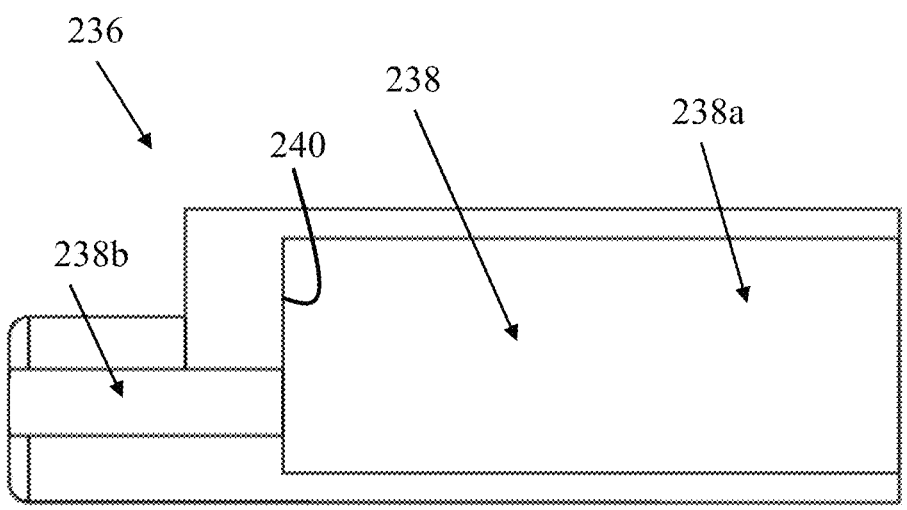
FIG. 27D is a cross-sectional view of the alignment spacer of FIGS. 27A-27B taken along the line A-A of FIG. 27A.

As shown in FIGS. 26-27D, the drive assembly 200 may include an alignment adapter or spacer 236 configured to substantially maintain the orientation of the distal arm 104 during operation and to operably decouple the collar 120 from the connector 216, such as after the tissue clipping assembly 102 has been moved to the closed and locked positions.

The alignment spacer 236 may be substantially cylindrical and sized, shaped, and configured to linearly slide within the inner surfaces of the collar 120 and the connector 216. The alignment spacer 236 may define a drive passage 238 extending through the length of the alignment spacer 236. The drive passage 238 may be sized, shaped, and configured to receive a portion of the drive element 204 therethrough such that the drive element 204 is translatable through the drive passage 238.

The alignment spacer 236 may be disposed in an operational position within and between the collar 120 and the connector 216 when the collar 120 and the connector 216 are coupled to maintain the coupling of the collar 120 and the connector 216. The alignment spacer 236 may be disposed within the collar 120 and the connector 216 such that the outer surface of the alignment spacer 236 abuts the inner surfaces of the collar 120 and the connector 216. The outer surface of the alignment spacer 236 may abut the inner surfaces of the connecting portions 168, 226 of the collar 120 and the connector 216 to prevent the collar 120 and the connector 216 from decoupling. For example, the outer surface of the alignment spacer 236 may simultaneously abut the connecting projections 170 of the collar 120 and the connecting projections 228 of the connector 216 to prevent the connecting projections 170 of the collar 120 from moving out of the receiving areas 230 of the connector 216 and to prevent the connecting projections 228 of the connector 216 from moving out of the receiving areas 172 of the collar 120. The distal end of the alignment spacer 236 may be disposed near the proximal end of the distal arm 104 when the alignment spacer 236 is in the operational position and the distal arm 104 is in the set position. During operation, the positioning of the alignment spacer 236 near the collar 120 may assist in guiding the distal arm 104 to recruit tissue.

The alignment spacer 236 may also be linearly translatable within the collar 120 and the connector 216 to decouple the connector 216 from the collar 120. The alignment spacer 236 may be linearly translated, such as proximally, from beneath the connecting portions 168, 226 of the collar 120 and the connector 216 such that the alignment spacer 236 no longer supports the coupling between the collar 120 and the connector 216. For example, the alignment spacer 236 may be proximally retracted entirely into the connector 216. Without the support of the alignment spacer 236, the connector 216 may be moved, such as via the catheter 212, such that the connecting projections 228 of the connector 216 are moved out of the receiving areas 172 of the collar 120 and vice versa, thereby decoupling the collar 120 from the connector 216 and the catheter 212.

Figure 28A:
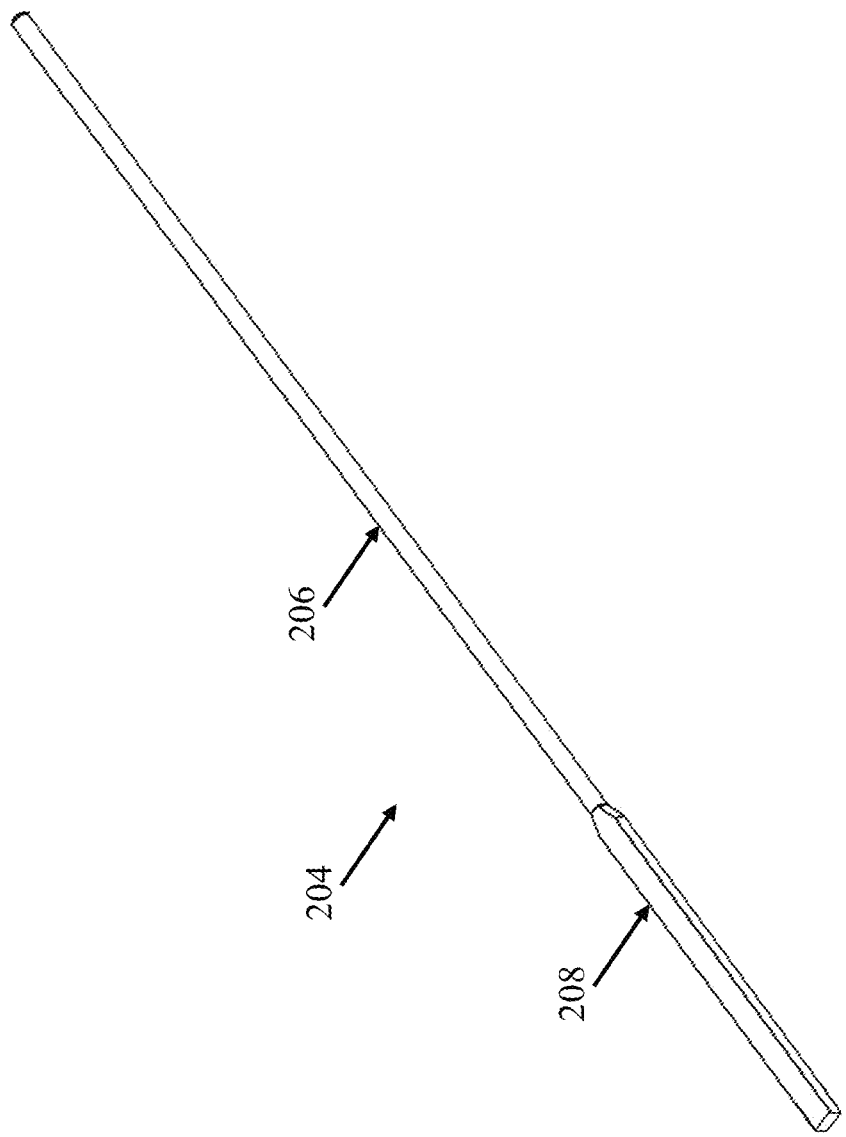
FIG. 28A is a perspective view of a drive element according to one embodiment.
Figure 28B:
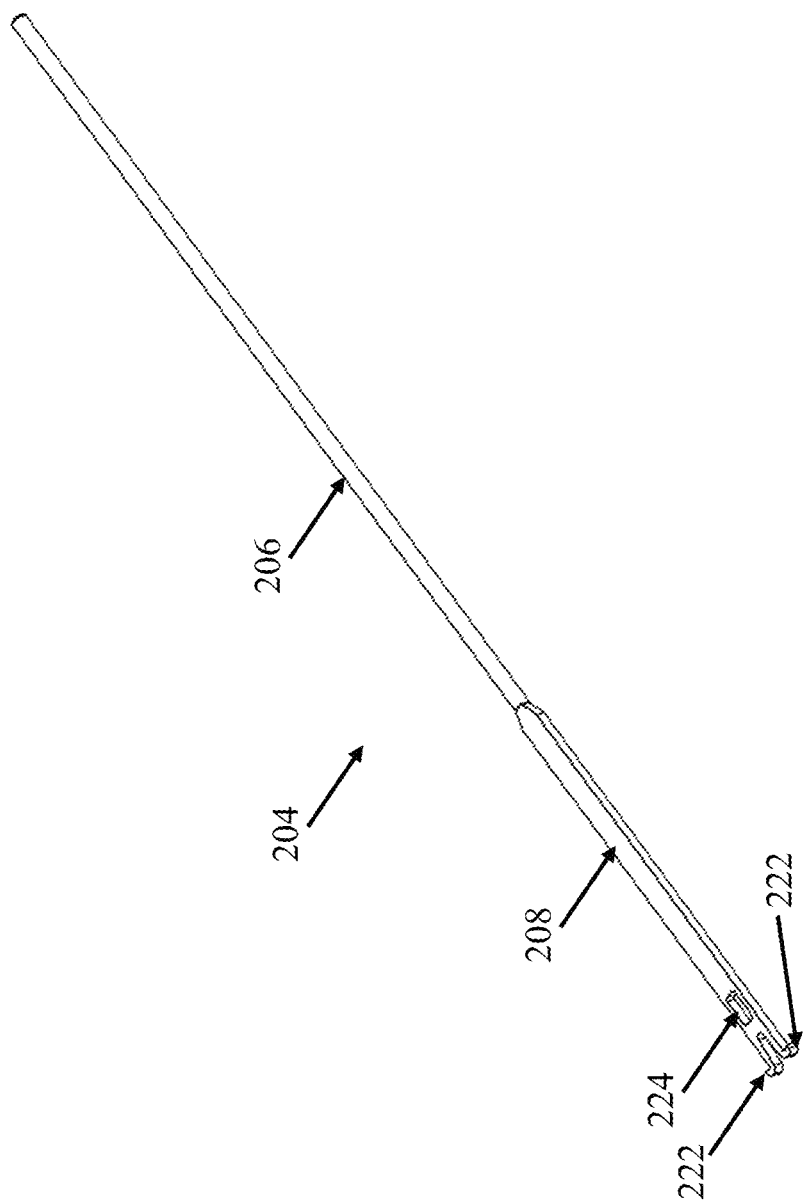
FIG. 28B is a perspective view of a drive element according to another embodiment.

Referring now to FIGS. 28A and 28B, the drive element 204 may include a proximal portion 206 which may be coupled to the handle 202, such as to the control actuator 210, and a distal portion 208 which may be operably coupled with the tissue clipping assembly 102, such as via the coupler 214. The proximal portion 206 may be sized, shaped, and configured to extend through the catheter 212 and transmit translational and rotational movement from the handle 202 toward the tissue clipping assembly 102. In some embodiments, the proximal portion 206 of the drive element 204 may be sized, shaped, and configured to decrease friction applied to the catheter 212 when the tissue clipping device 100 is operated. In an exemplary embodiment, the proximal portion 206 of the drive element 204 is configured to allow the distal arm 104 to flexibly recruit tissue and the distal portion 208 is configured to guide the distal arm 104 linearly out of and into the collar 120. The proximal portion 206 of the drive element 204 may be a toque shaft which may be translated and rotated by an operator, such as via the handle 202.

The distal end of the distal portion 208 of the drive element 204 may be coupled with the tissue clipping assembly 102, such as with the proximal end of the distal arm 104. The distal portion 208 may be sized, shaped, and configured to increase control of the distal arm 104 as the distal arm 104 is operated to clip tissue. The distal portion 208 of the drive element 204 may have a different cross section than the proximal portion 206 of the drive element 204. In some embodiments, the distal portion 208 of the drive element 204 has a wider cross section than the proximal portion 206 of the drive element 204, such as to decouple the drive assembly 200 from the tissue clipping assembly 102, as described below. In some embodiments, the distal portion 208 of the drive element 204 has a substantially rectangular cross section and comprises stainless steel or Nitinol. In other embodiments, the distal portion 208 of the drive element 204 includes multiple wires spaced laterally apart and extending in parallel toward the tissue clipping assembly 102.

While the proximal portion 206 of the drive element 204 has been described as having a circular cross section and the distal portion 208 of the drive element 204 has been described as having a rectangular cross section, it will be understood that the drive element 204 may have other shapes and configurations. For example, both the proximal and distal portions 206, 208 of the drive element 204 may have a substantially circular cross section or both the proximal and distal portions 206, 208 may have a substantially rectangular cross section. The distal portion 208 may also be wider to guide the linear extension and retraction of the distal arm 104 relative to the proximal arm 110. For example, the wider distal portion 208 may make the distal portion 208 stronger such that the distal portion 208 remains substantially in line with the distal opening of the alignment spacer 236 as the distal arm 104 is linearly extended and retracted, such as during the tissue clipping operation. The distal portion 208 may remain relatively in lace as the proximal portion 206 is maneuvered by an operator. For example, the distal portion 208 may be stiffer than the proximal portion 206.

The distal end of the proximal portion 206 of the drive element 204 may be fixed to the proximal end of the distal portion 208 of the drive element 204. In an exemplary embodiment, the distal end of the proximal portion 206 is welded to the proximal end of the distal portion 208. In other embodiments, the distal end of the proximal portion 206 is coupled with the proximal end of the distal portion 208 via adhesives, solder, fasteners, or other suitable means known in the art to couple the proximal portion 206 to the distal portion 208. In an exemplary embodiment, the proximal and distal portions 206, 208 are integral.

In some embodiments, the proximal portion 206 of the drive element 204 has a length nearly corresponding to the distance which the distal arm 104 is to be extended from the catheter 212. For example, the drive assembly 200 may be configured to limit the distal extension of the proximal portion 206 of the drive element 204 such that the extension length of the distal arm 104 is substantially equivalent to the length of the distal portion 208 of the drive element 204. In embodiments, where the distal arm 104 is configured to be extended about 3 cm from the catheter 212, the distal portion 208 of the drive element 204 may have a length of about 3 cm or slightly larger. The distal portion 208 may have a length similar to or longer than the length of the distal tine 112 such that the distal arm 104 may be effectively guided relative to the collar 120.

Referring back to FIGS. 27C-27D, the drive passage 238 of the alignment spacer 236 may be sized, shaped, and configured to permit a proximal portion of the distal portion 208 of the drive element 204 to be distally extended through the drive passage 238 and such that the alignment spacer 236 may be proximally retracted when the drive element 204 is proximally retracted, such as after the tissue clipping assembly 102 has been moved to the closed and locked positions. The drive passage 238 may include a proximal portion 238*a* at the proximal end and a distal portion 238*b* at the distal end. The proximal portion 238*a* of the drive passage 238 may be sized, shaped, and configured to receive the distal end of the proximal portion 206 of the drive element 204 therein and to allow the distal portion 208 of the drive element 204 to translate therethrough. The distal portion 238*b* of the drive passage 238 may be sized, shaped, and configured to permit the distal portion 208 of the drive element 204 to translate therethrough. The distal portion 238*b* of the drive passage 238 may also be sized, shaped, and configured to prevent the proximal portion 206 of the drive element 204 from extending therein. The distal portion 238*b* of the drive passage 238 may also be sized, shaped, and configured to prevent a distal portion of the drive element 204, such as the prongs 222, from extending therethrough.

In some embodiments, the cross section of the proximal portion 238*a* of the drive passage 238 is wider than the distal portion 238*b* of the drive passage 238. In some embodiments, the cross section of the proximal portion 238*a* of the drive passage 238 corresponds to the cross section of the proximal portion 206 of the drive element 204 (e.g., circular). In some embodiments, the cross section of the distal portion 238*b* of the drive passage 238 corresponds to the cross section of the distal portion 208 of the drive element 204 (e.g., rectangular).

In some embodiments, the alignment spacer 236 includes a shoulder 240 disposed at the distal end of the proximal portion 238*a* of the drive passage 238. The shoulder 240 may be configured to abut the distal end of the proximal portion 206 of the drive element 204. The shoulder 240 may be configured to prevent the proximal portion 206 of the drive element 204 from extending into the distal portion 238*b* of the drive passage 238 while allowing the distal portion 208 of the drive element 204 to extend into the distal portion 238*b* of the drive passage 238. The drive element 204 may also include a stop feature which abuts the shoulder 240 to prevent the proximal portion 206 of the drive element 204 from extending into the distal portion 238*b* of the drive passage 238.

The alignment spacer 236 may be disposed between the connecting portions 168, 226 of the collar 120 and the connector 216 when the device 100 is extended into the body and when the tissue clipping assembly 102 is maneuvered to clip tissue (e.g., the operational position), such as to maintain the coupling of the collar 120 and the connector 216. The alignment spacer 236 may allow the distal portion 208 of the drive element 204 to be extended through the drive passage 238 such that the distal arm 104 may be operated to grasp tissue as described above. The alignment spacer 236 may also prevent the proximal portion 206 of the drive element 204 from extending through the drive passage 238, such as to control the extension length of the distal arm 104. The cross section of the distal portion 238*b* of the drive passage 238 may substantially correspond to the cross section of the distal portion 208 of the drive element 204 such that the orientation of the distal portion 208 of the drive element 204 substantially corresponds to the orientation of the alignment spacer 236, such as to prevent the distal portion 208 of the drive element 204 and the distal arm 104 from rotating or twisting when the distal portion 208 is distally extended. In some embodiments, the distal end of the alignment spacer 236 is narrower to increase the stiffness of the alignment spacer 236 around the distal portion 238*b* of the drive passage 238.

In some embodiments, the alignment spacer 236 includes one or more ridges 242 extending radially outwardly from an outer surface of the alignment spacer 236. The ridges 242 may extend radially outward from a proximal portion of the alignment spacer 236. The ridges 242 may extend into slots 244 extending along a length of the connector 216 (see FIGS. 23-24B). The ridges 242 may be retained in the slots 244 of the connector 216 to maintain the orientation of the alignment spacer 236 during operation, such as to maintain the orientations of the distal portion 208 of the drive element 204 and the distal arm 104 during the tissue clipping operation. For example, the slots 244 may permit linear translation of the alignment spacer 236 but prevent rotation of the alignment spacer 236 when the ridges 242 are disposed in the slots 244.

The slots 244 of the connector 216 may also control the linear translation of the alignment spacer 236. For example, the alignment spacer 236 may be prevented from translating distally through the connector 216 when the ridges 242 abut the distal ends of the slots 244. In some embodiments, the distal ends of the slots 244 may be positioned such that the alignment spacer 236 is in the operational position between the connecting portions 168, 226 of the collar 120 and the connector 216 when the ridges 242 abut the distal ends of the slots 244 (e.g., the alignment spacer 236 may only translate proximally). In another embodiment, the slots 244 have narrower portions that abut the ridges 242 thereby preventing the alignment spacer 236 from being moved proximally until a sufficient force is delivered to the alignment spacer 236 via the drive element 204. The force required to proximally retract the alignment spacer 236 may be between about 1 pound and about 10 pounds, such as between about 2 pounds and about 4 pounds.

Figure 24B:
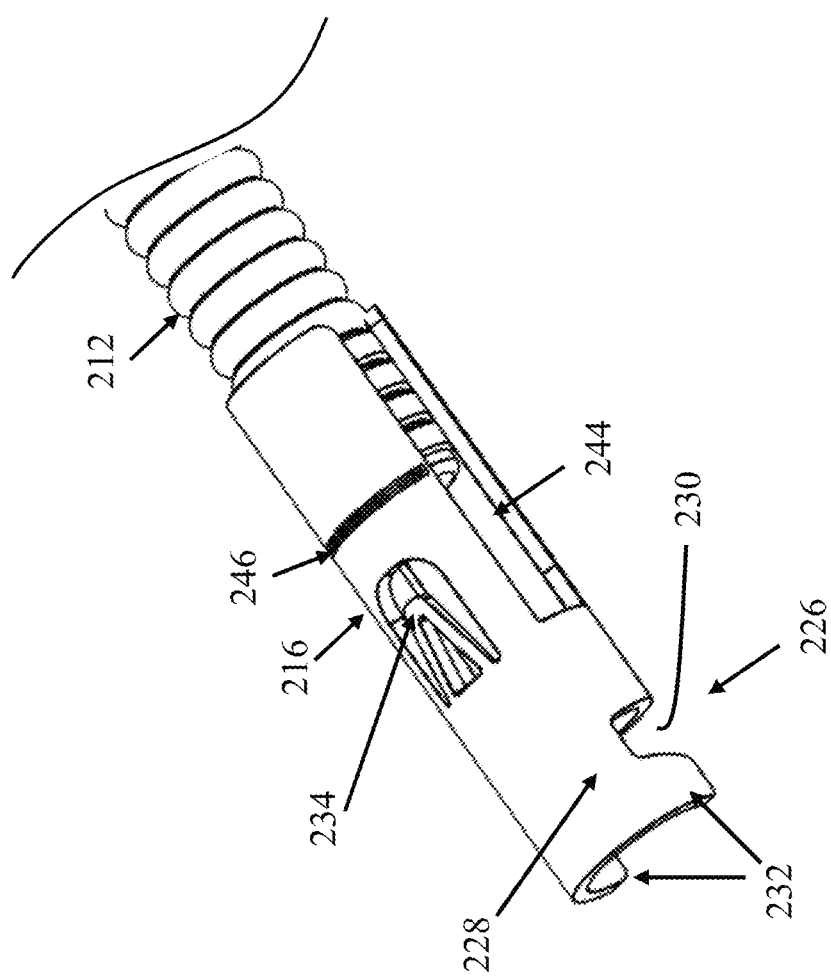
Figure 25A:
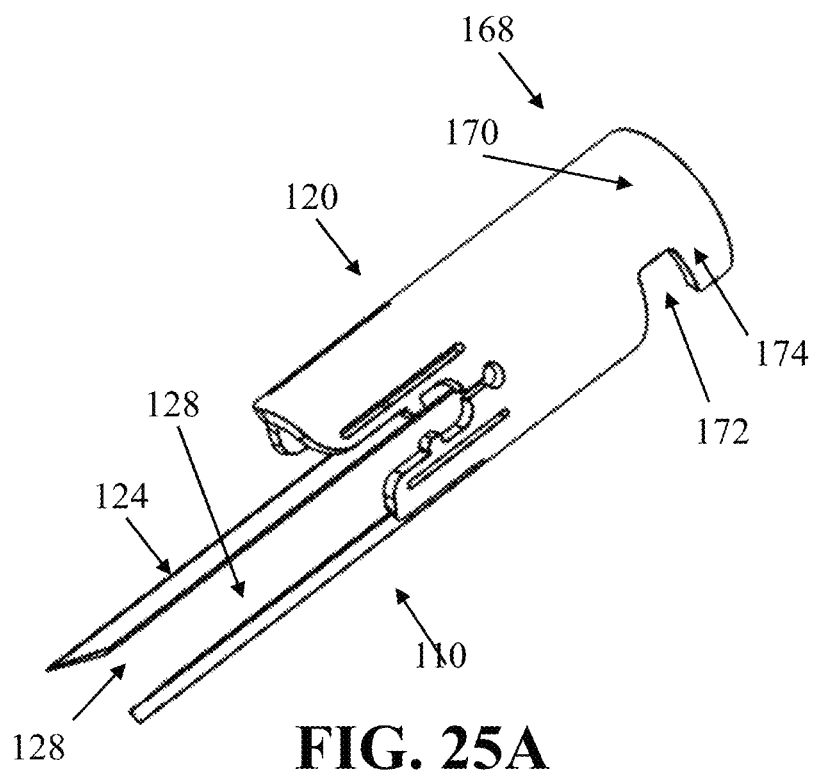
FIGS. 25A and 25B are top and bottom perspective views of the collar of the tissue clipping assembly of FIG. 23.
Figure 25B:
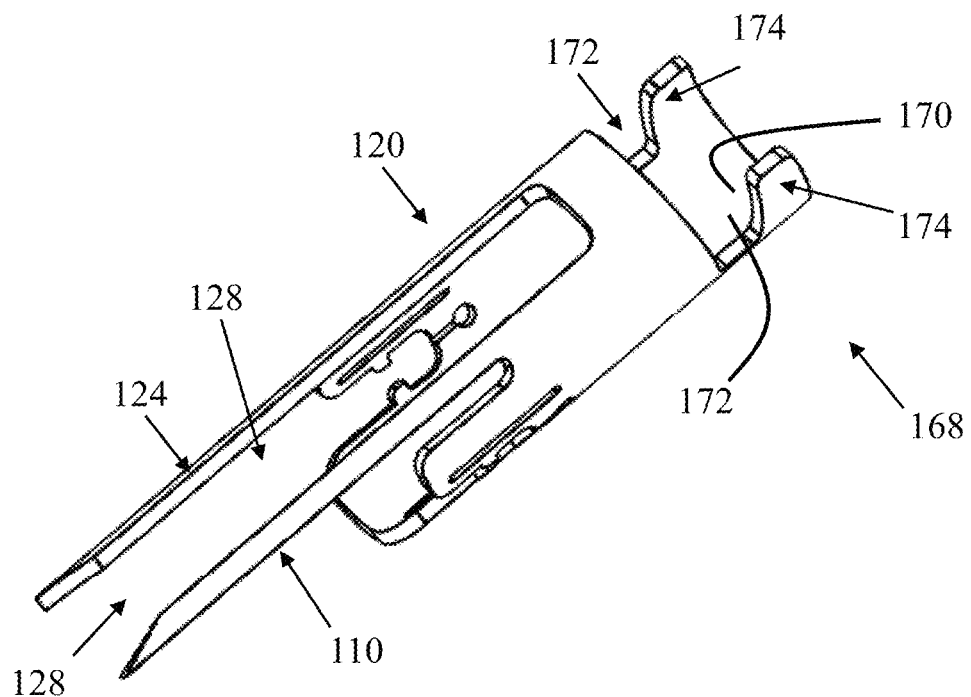

In some embodiments, as shown in FIG. 24B, the connector 216 includes a retention tab 234 configured to operably retain the alignment spacer 236 in the operational position to maintain the coupling between the collar 120 and the connector 216. The retention tab 234 may be bent or flexed radially inwardly to abut the proximal end of the alignment spacer 236 when the alignment spacer 236 is in the operational position. The abutment between the retention tab 234 and the alignment spacer 236 may prevent the alignment spacer 236 from proximally retracting during the tissue clipping operation. The retention tab 234 may flex or bend radially outwardly when the alignment spacer 236 is retracted with sufficient force, such as via the drive element 204, such that the retention tab 234 no longer abuts the alignment spacer 236, thereby allowing the alignment spacer 236 to be proximally retracted. In some embodiments, the connector 216 includes fiducials 246 extending between the slots 244 which aid in assembly and provide a visual cue to an operator that the connector 216 is disposed properly on the catheter 216. The fiducials 246 may also be flexible such as to allow the connector 216 to flex or bend, such as to place the proximal end of the connector 216 around the distal end of the catheter 212.

The alignment spacer 236 may be proximally retracted from between the connecting portions 168, 226 of the collar 120 and the connector 216 by proximal retraction of the drive element 204, such as after the tissue clipping assembly 102 has been moved to the closed and locked positions. After the distal end of the drive element 204 is decoupled from the tissue clipping assembly 102, the drive element 204 may be proximally retracted through the drive passage 238 of the alignment spacer 236. The drive element 204 may be retracted until a distal portion of the drive element 204, such as the prongs 222, abut the distal end of the alignment spacer 236. The drive element 204 may then be retracted with sufficient proximal force, such as via the handle 202, that the abutment between the drive element 204 and the alignment spacer 236 proximally retracts the alignment spacer 236. For example, the drive element 204 may be retracted with sufficient force to flex the retention tab 234 radially outwardly such that the alignment spacer 236 may be proximally retracted with the drive element 204. After the alignment spacer 236 is proximally retracted from the operational position, the collar 120 may be decoupled from the connector 216 and the catheter 212 such that the tissue clipping assembly 102 is decoupled from the drive assembly 200.

While the drive element 204 has been described with a distal portion 208 having a flat, rectangular cross section to control the orientation and deflection of the distal arm 104 during operation, it will be understood that the distal portion 208 may have other configurations and assemblies. For example, the distal portion 208 of the drive element 204 may include two or more wires, such as stainless steel or Nitinol wires, extending in parallel to the distal arm 104, such as shown in FIG. 22A.

Referring now to FIGS. 29A-32, the tissue clipping device 100 may be operated to clip tissue with the tissue clipping assembly 102 and the tissue clipping assembly 102 may be decoupled from the drive assembly 200, such as to deploy the tissue clipping assembly 102 in the body to maintain closure of the tissue. The tissue clipping assembly 102 may be inserted into a position above and substantially parallel to target tissue, such as an identified defect. The tissue clipping assembly 102 may be operated via the drive assembly 200 to linearly clip tissue, such as to clip together opposing sides of a defect. The tissue clipping assembly 102 may be moved to a closed position and locked position to continue to clip tissue. The tissue clipping assembly 102 may be decoupled from drive assembly 200, such as to maintain closure of the defect with the tissue clipping assembly 102. FIGS. 29B, 30B, and 31B show the tissue clipping device 100 without the collar 120 and the connector 216 to show the inner components of the tissue clipping assembly 102 and the drive assembly 200.

As shown in FIGS. 29A-29B, the tissue clipping assembly 102 may be extended through the catheter 212, such as through an endoscope, to a desired location, such as above a defect. The distal arm 104 of the tissue clipping assembly 102 may be coupled with the distal end of the drive element 204. The distal arm 104 and the drive element 204 may extend through the collar 120 and the proximal arm 110 may also extend from the distal end of the collar 120. The locking projections 130 of the distal arm 104 may be disposed in the setting recesses 141 of the collar 120 such that the tissue clipping assembly 102 is in the set position. The distal arm 104 may include the housing 154 which substantially shrouds the proximal arm 110. The collar 120 is operably coupled with the distal end of the catheter 212 via the connector 216. The connecting portion 168 of the collar 120 may operably couple with the connecting portion 226 of the connector 216 and the alignment spacer 236 may be disposed between the connecting portions 168, 226 to maintain the coupling between the collar 120 and the connector 216. The drive element 204 extends through the alignment spacer 236 and is operably coupled with the distal arm 104.

As shown in FIGS. 30A-30B, the distal arm 104 may be linearly extended (e.g., parallel to the surface of the tissue) from the collar 120 to the extended configuration such that the tissue clipping assembly 102 may be positioned on opposite sides of target tissue. The drive element 204 may be distally extended, such as via the handle 202, to linearly extend the distal arm 104. The tissue clipping device 100 may be maneuvered such that the proximal arm 110, such as the proximal tines 124, grasps tissue at a first tissue location and such that the distal arm 104, such as the distal tine 112, grasps tissue at a second tissue location. The second tissue location may be substantially opposite the first location. In some embodiments, the distal tine 112 of the distal arm 104 may flex a distance radially outwardly (e.g., downwardly) such that the distal tine 112 may grasp tissue.

Figure 31A:
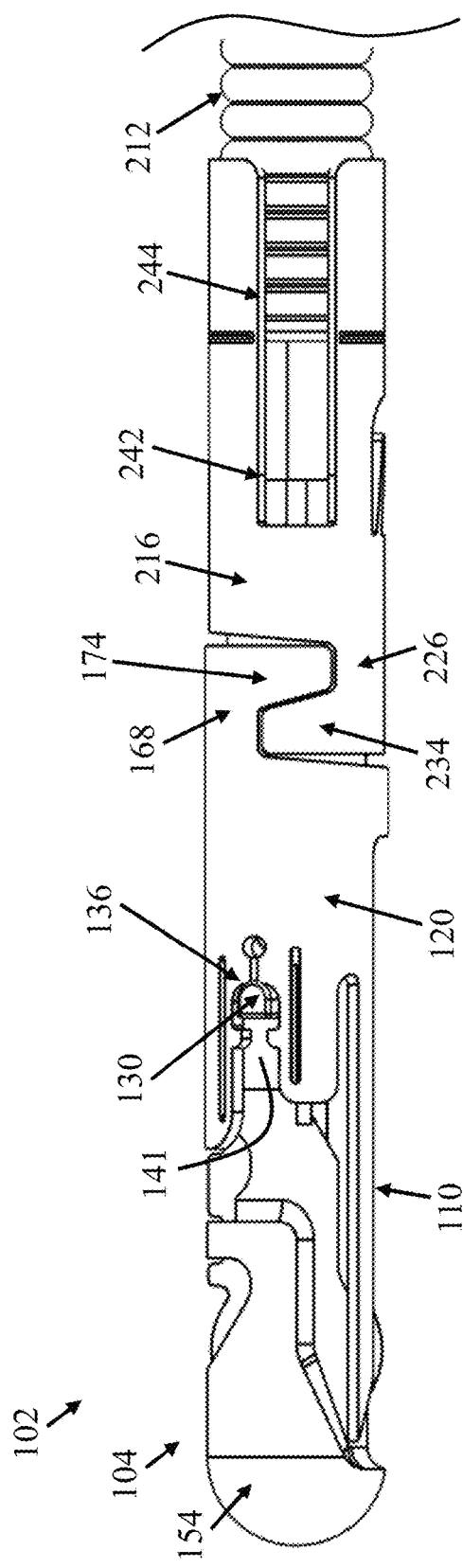
FIG. 31A is a side view of the tissue clipping assembly of FIG. 23 in a closed and locked position.
Figure 31B:
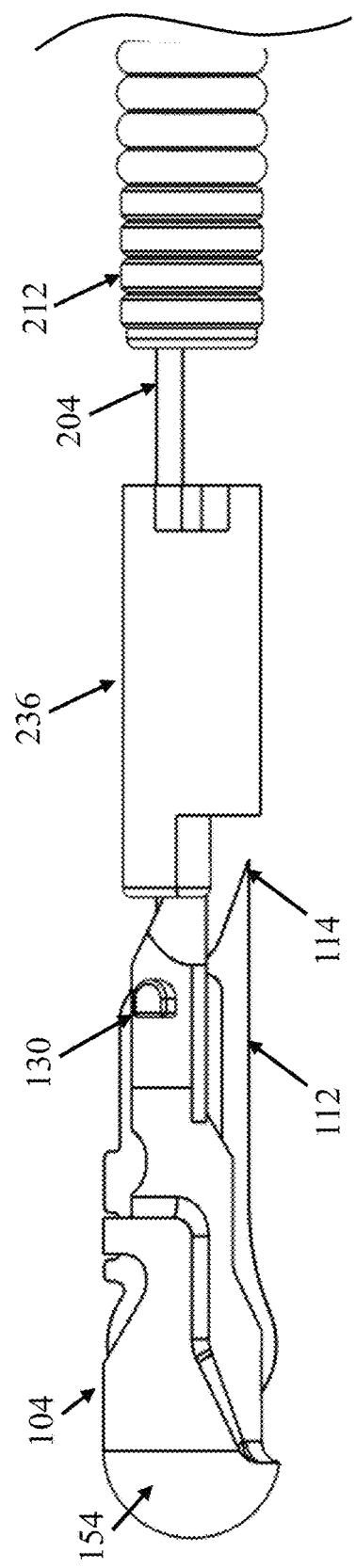
FIG. 31B is a side view of the tissue clipping assembly of FIG. 31A with the collar and connector removed.

As shown in FIGS. 31A-31B, the distal arm 104 may be proximally retracted to clip tissue between the distal arm 104 and the proximal arm 110 and the tissue clipping assembly 102 may be moved to the closed and locked positions such that the position of the distal arm 104 is maintained relative to the collar 120. The distal arm 104 may be proximally retracted by proximally retracting the drive element 204, such as via the handle 202. The retraction of the distal arm 104 may clip tissue between the distal and proximal arms 104, 110. In some embodiments, before the tissue clipping assembly 102 is moved to the locked position, the tissue clipping assembly 102 may be proximally retracted to the set position shown in FIGS. 29A-29B such that the operator may confirm the tissue clipping assembly 102 is properly clipping tissue. The tissue clipping assembly 102 may be moved to the closed and locked positions by proximally retracting the distal arm 104 via the drive element 204 such that the locking projections 130 are moved into the receiving portions 136. The disposition of the locking projections 130 in the receiving portions 136 may secure the position of the distal arm 104 in the closed position relative to the collar 120. In some embodiments, the distal arm 104, such as the housing 154, may shroud the proximal arm 110 to prevent trauma to tissue. The distal tine 112 may be closed relative to the proximal arm 110. In some embodiments, the distal arm 104 linearly overlaps with the proximal arm 110 to clip tissue in the closed position. In some embodiments, the distal arm 104 is operable to recruit tissue into the collar 120 when the tissue clipping assembly 102 is moved to the closed position.

Figure 32:
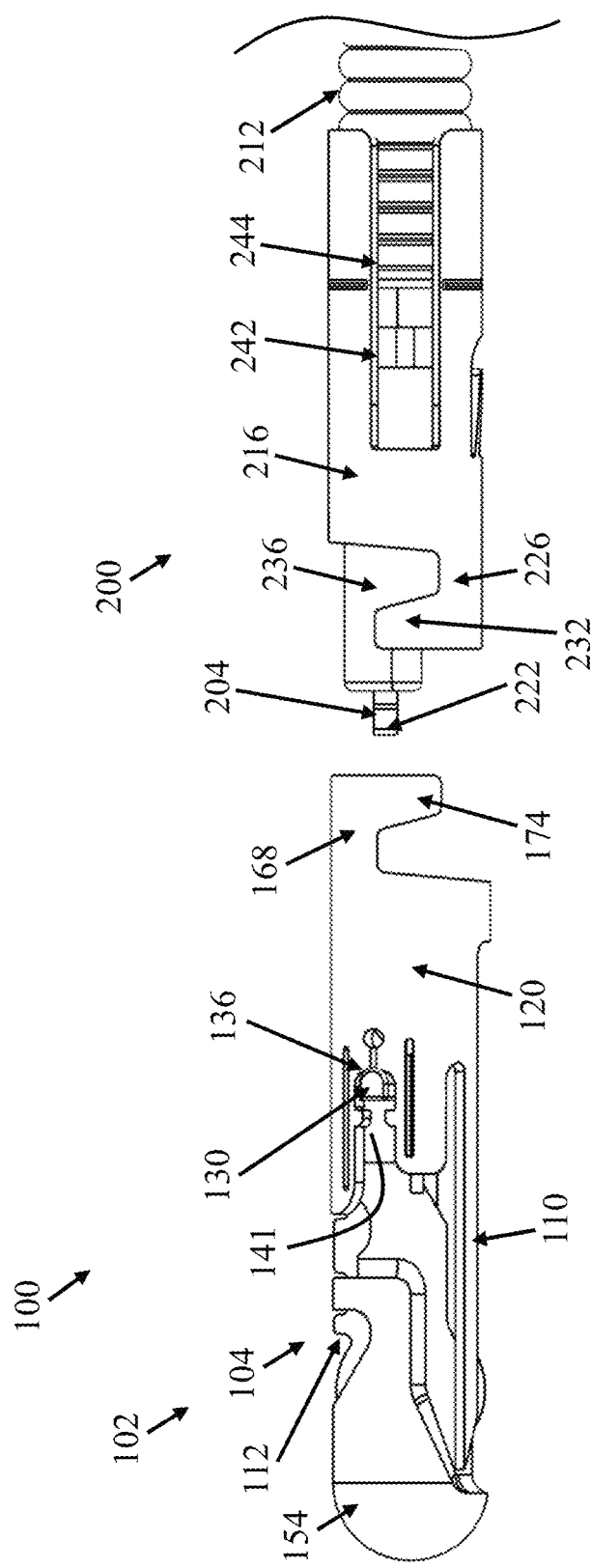
FIG. 32 is a side view of the tissue clipping assembly of FIG. 23 in a deployed position.

As shown in FIG. 32, the tissue clipping assembly 102 may be decoupled from the drive assembly 200 such as to deploy the tissue clipping assembly 102 in the closed clipping position in the tissue. After the tissue clipping assembly 102 has been moved to the closed and locked positions, the drive element 204 may be proximally retracted with sufficient force to decouple the distal arm 104 from the drive element 204. The drive element 204 may be retracted further such that the drive element 204 abuts the distal end of the alignment spacer 236. The drive element 204 may be proximally retracted with sufficient force such that the alignment spacer 236 is pulled proximally from its position maintaining the coupling between the collar 120 and the connector 216. The connector 216 may then be decoupled from the collar 120, such as via maneuvering the catheter 212. With the tissue clipping assembly 102 decoupled from the drive assembly 200, the tissue clipping assembly 102 may be deployed in the body such that the tissue clipping assembly 102 continues to clip tissue. The drive assembly 200 may then be withdrawn from the body. In some embodiments, the tissue clipping assembly 102 deployed in the body to clip tissue has a length between about 5.0 mm and about 30.0 mm, such as between about 10.0 mm and about 20.0 mm, such as about 14 mm. For example, the tissue clipping assembly 102 may have a length which reduces abrasion of surrounding tissue and premature dislodgement of the tissue clipping assembly 102 when the tissue clipping assembly 102 is deployed.

While the alignment spacer 236 has been described as being a singular component with a drive passage 238 with a proximal portion 238a and a distal portion 238b, it will be understood that the tissue clipping device 100 may have other assemblies and configurations. For example, as shown in FIG. 33, the tissue clipping assembly 102 may include a first alignment spacer operable to limit the linear extension of the proximal portion 206 of the drive element 204 and a second alignment spacer operable to control the orientation of the distal portion 208 of the drive element 204 and to abut the distal end of the drive element 204 as the drive element is retracted. However, the inclusion of a single alignment spacer 236 as described above may allow the tissue clipping device 100, the tissue clipping assembly 102, and/or the drive assembly 200 to have a smaller profile.

Figure 33A:
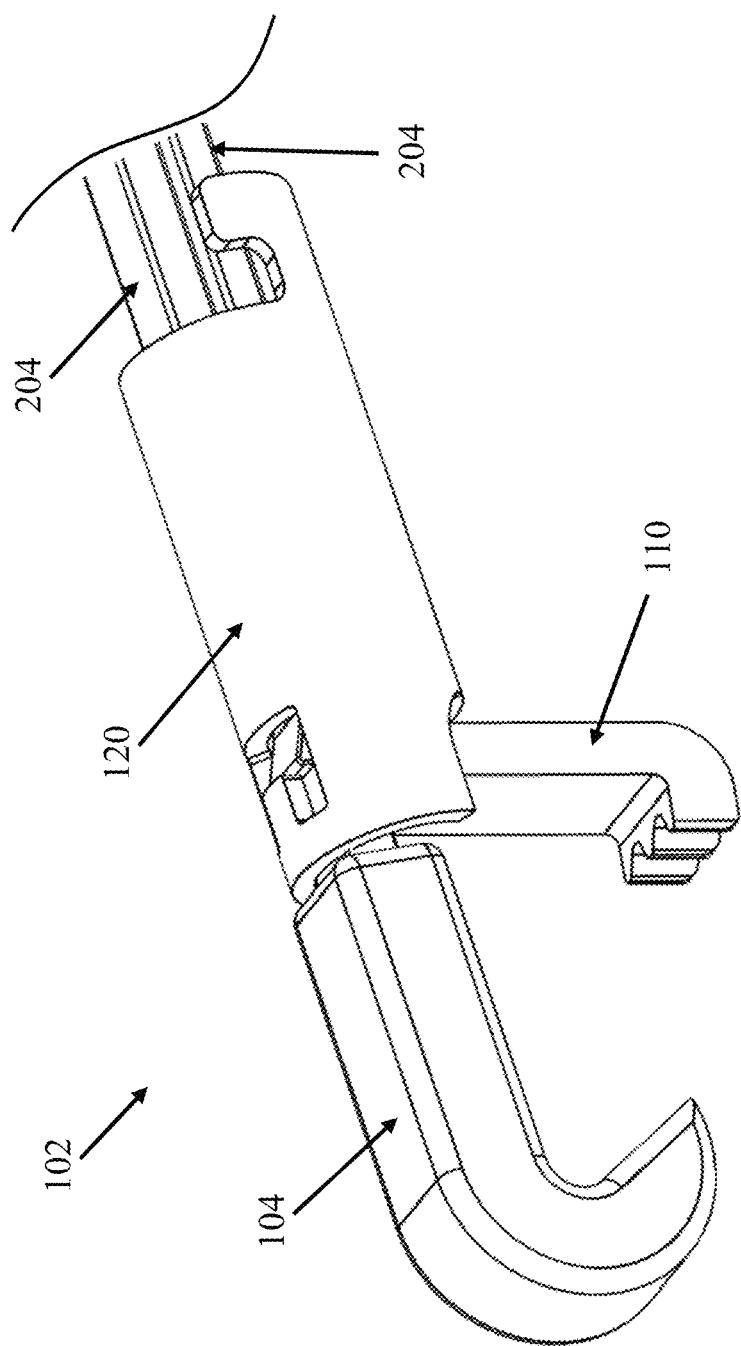
FIG. 33A is a perspective view of a tissue clipping assembly according to another embodiment.
Figure 33B:
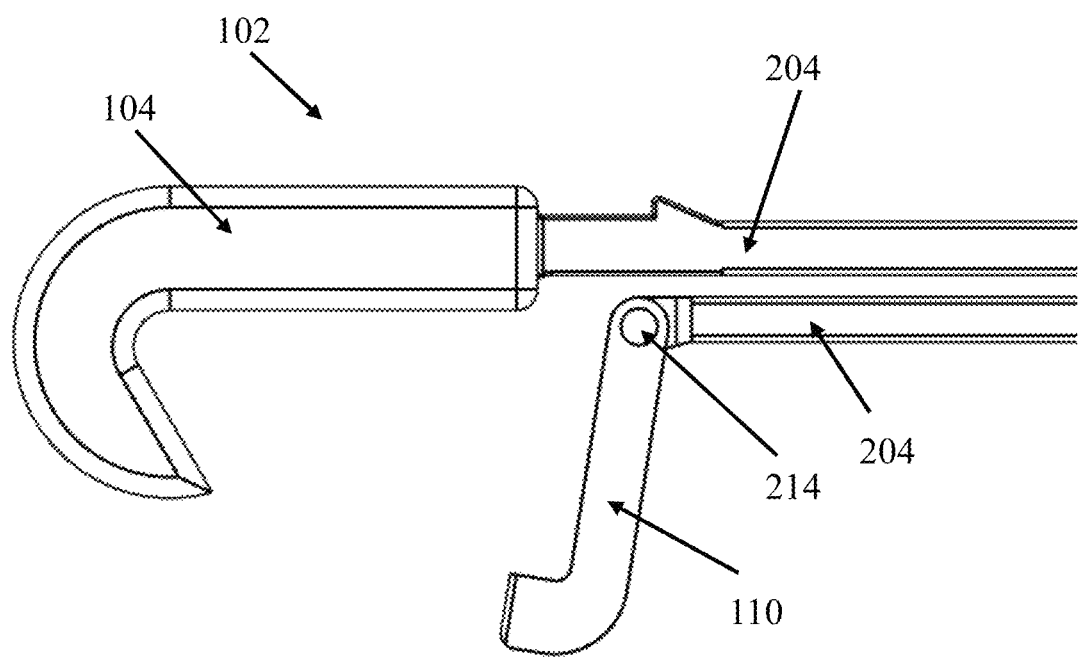
FIG. 33B is a side view of the tissue clipping assembly of FIG. 33A with the collar removed.
Figure 33C:
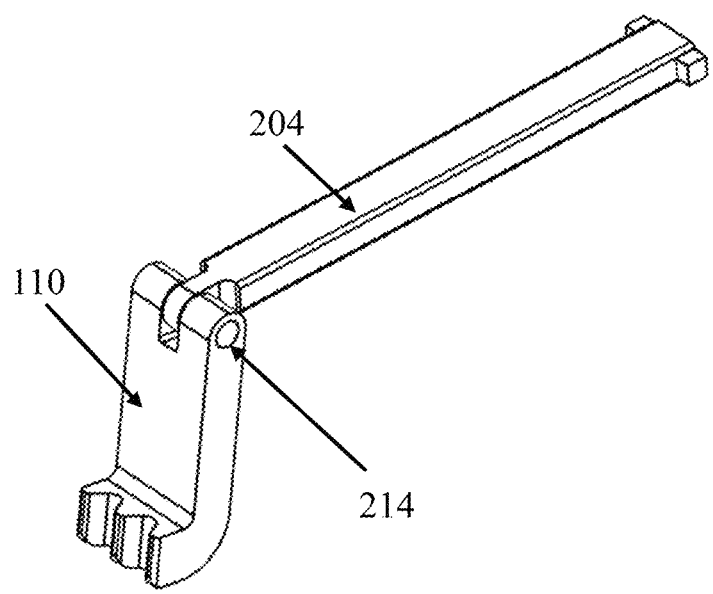
FIG. 33C is a perspective view of the tissue clipping assembly of FIG. 33B with the distal arm removed.

In some embodiments, as shown in FIGS. 33A-33C, the proximal arm 110 may be pivotable about the distal end of the collar 120. The proximal end of the proximal arm 110 may be coupled with a drive element 204 which may open and close the proximal arm 110 via linear extension and retraction of the drive element 204. For example, the proximal arm 110 may be opened when the tissue clipping assembly 102 is placed in position relative to the target tissue and the proximal arm 110 may be close to grasp tissue on one side of the target tissue.

The proximal arm 110 may be decoupled from the drive element 204, such as after the tissue clipping assembly 102 has been moved to the closed position. For example, the proximal arm 110 may be pivotably coupled with the distal end of the drive element 204 via a pin or link such that the proximal arm 110 may pivot about the link and which breaks under a predetermined force to decouple the proximal arm 110 from the drive element 204. In other embodiments, the drive element 204 coupled to the proximal arm 110 may be decoupled from the drive element 204 in any of the manners described above. The position of the proximal arm 110 may be fixed relative to the collar 120, such as described above.

In some embodiments, the tissue clipping device 100, such as the tissue clipping assembly 102 and/or the drive assembly 200, may include markings or other indicia to assist operators in positioning and operating the tissue clipping device 100. For example, the collar 120 may include one or more indicia indicative of an orientation of the tissue clipping device 100. Additionally, the connector 216 may also include one or more indicia indicative of an orientation of the tissue clipping device 100. For example, one or more of the indicia of the collar 120 and the connector 216 may be arrows indicative of the extension direction of the distal arm 104 and one or more indicia of the collar 120 may be arrows indicating the orientation of the device 100 such that the tissue clipping assembly 102 is properly oriented to clip tissue. In some embodiments, the collar 120 also includes indicia or other markings that aid in the assembly and/or manufacture of the tissue clipping device 100.

The tissue clipping device 100 may be operable with multiple tissue clipping assemblies 102, such as to clip multiple tissue locations. After a first tissue clipping assembly 102 is deployed to clip tissue, a second tissue clipping assembly 102 may be coupled to the drive assembly 200 such that the drive assembly 200 may deploy the second tissue clipping assembly 102 to clip tissue. The second tissue clipping assembly 102 may be substantially similar to the first tissue clipping assembly 102 or may have a different size, shape, or configuration, such as based upon differences in tissue deployment location. The deployment of multiple tissue clipping assemblies 102 may permit the tissue clipping device 100 to close larger defects or lesions than conventional recruiting devices and hemostatic clips. For example, the device 100 may be used to clip elongated sections of tissue, such as elongated or oval lesions, using multiple tissue clipping assemblies 102.

Referring now to FIGS. 34A-34D, the tissue clipping device 100 may be operable to deploy multiple tissue clipping assemblies 102 to clip target tissue, such as to close an elongated defect.

Figure 34A:
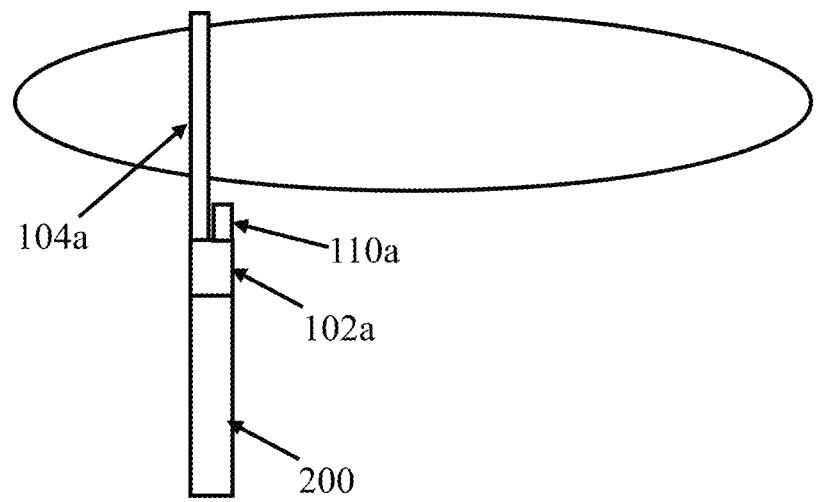
FIGS. 34A-34D are schematic illustrations depicting a methodology for clipping tissue with a tissue clipping device using multiple tissue clipping assemblies.

As shown in FIG. 34A, after the target tissue, such as the defect, in a body has been identified, the endoscope and/or the tissue clipping device 100 may be positioned above and facing toward the tissue. The device 100 may be positioned on a first side of the target tissue and at one end of the target tissue. The tissue clipping device 100 includes a first tissue clipping assembly 102a coupled to the drive assembly 200. The first tissue clipping assembly 102a includes a first distal arm 104a and a first proximal arm 110a. The first distal arm 104a may be linearly extended across the width of the tissue past the second side of the target tissue opposite the first side. The device 100 may be operated to grasp tissue at the second side of the tissue with the first distal arm 104a and to grasp tissue at the first side of the tissue with the first proximal arm 110a. The device 100 may then be operated to clip the sides of the tissue with the distal and proximal arms 104a, 110a, as described above.

While the tissue clipping device 100 has been described as clipping two opposing sides of a defect together, it will be understood that the device 100 may be used in other manners. For example, the distal arm 104 may be extended to recruit tissue from the center of a defect to the proximal arm 110 positioned at a side of the defect. The device 100 may then clip half of the defect, such as to create two more manageable defects. The device 100 may be used to further close the defect, such as with additional tissue clipping assemblies 102, or a hemostatic closure mechanism may be deployed to close the defect.

Figure 34B:
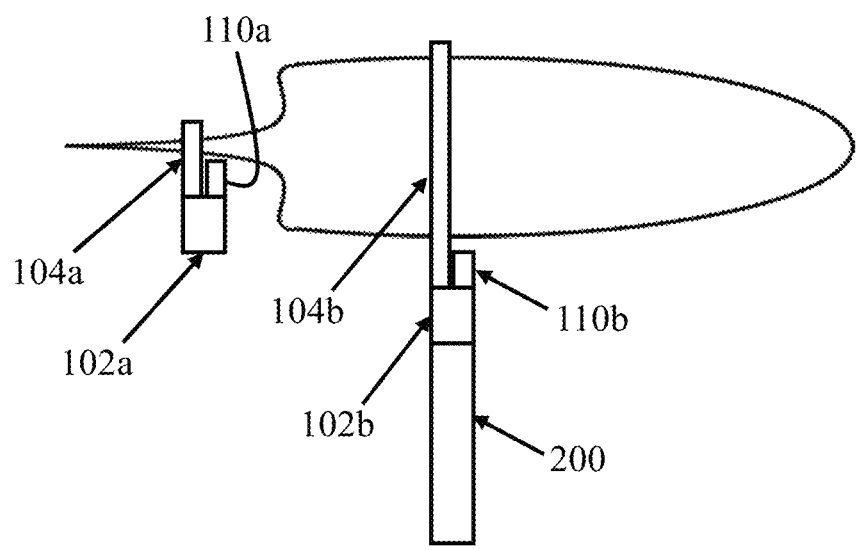

As shown in FIG. 34B, the drive assembly 200 may be decoupled from the first tissue clipping assembly 102*a*, the drive assembly 200 may be withdrawn from the body, and the tissue clipping device 100 may be reloaded with a second tissue clipping assembly 102*b*. The collar 120 of the second tissue clipping assembly 102*b* may be coupled to the distal end of the connector 216 and the distal arm 104*b* of the second tissue clipping assembly 102*b* may be coupled drive element 204, as described above. For example, the operator may reach through the slots 244 of the connector 216 to reset the alignment spacer 236 to the operational position to maintain the coupling between the connector 216 and the collar 120 of the second tissue clipping assembly 102.

The tissue clipping device 100 may be reinserted into the body, such as through the endoscope, and positioned above and facing toward the target tissue at a position spaced apart from the first tissue clipping assembly 102*a*. The device 100 may then be operated to clip the sides of the tissue with the distal and proximal arms 104*b*, 110*b* of the second tissue clipping assembly 102*b*. The second tissue clipping assembly 102*b* may be positioned such that the target tissue is substantially clipped or otherwise closed between the first and second tissue clipping assemblies 102*a*, 102*b*.

Figure 34C:
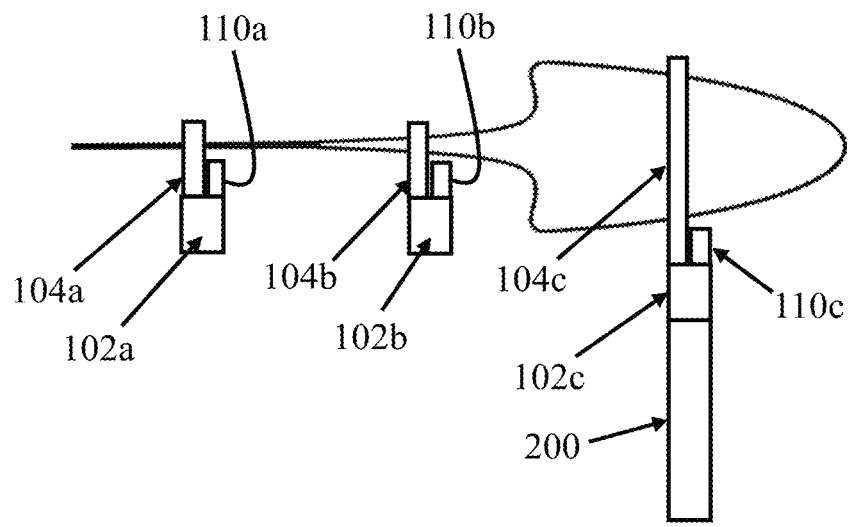

As shown in FIG. 34C, the drive assembly 200 may be decoupled from the second tissue clipping assembly 102*b*, the drive assembly 200 may be withdrawn from the body, and the tissue clipping device 100 may be reloaded with a third tissue clipping assembly 102*c*. The tissue clipping device 100 may be reinserted into the body, such as through the endoscope, and positioned above and facing toward the target tissue at a position spaced apart from the second tissue clipping assembly 102*b* on an opposite side of the first tissue clipping assembly 102*a*, such as at the other end of the target tissue. The device 100 may then be operated to clip the sides of the tissue with the distal and proximal arms 104*c*, 110*c* of the third tissue clipping assembly 102*c*. The third tissue clipping assembly 102*c* may be positioned such that the target tissue is substantially clipped or otherwise closed between the second and third tissue clipping assemblies 102*b*, 102*c*.

Figure 34D:
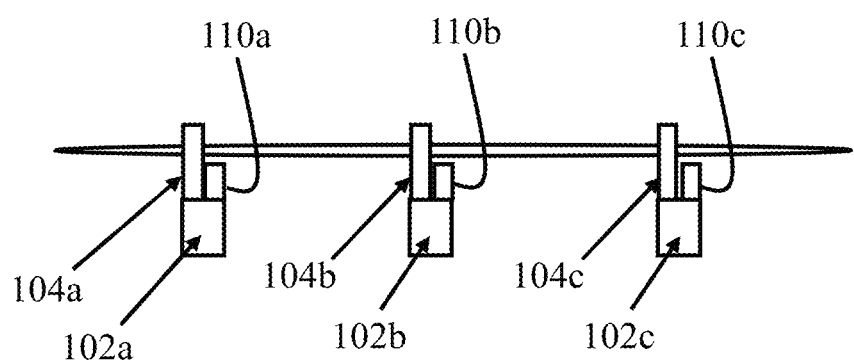

As shown in FIG. 34D, the drive assembly 200 may be decoupled from the third tissue clipping assembly 102*c* and withdrawn from the body. The tissue clipping assemblies 102*a*, 102*b*, 102*c* may be deployed to clip the first and second sides of the target tissue along the length of the target tissue. The tissue clipping assemblies 102 may be deployed to substantially close the length of the target tissue, such as to close a defect which would conventionally require more clips to close.

In the illustrated embodiment, the tissue clipping device 100 is operated to deploy three tissue clipping assemblies 102*a*, 102*b*, 102*c* to clip together an elongated section of tissue. However, it will be understood that the tissue clipping method shown in FIGS. 34A-34D is merely an illustrative example. For example, the tissue clipping device 100 may be used with one, two, or four or more tissue clipping assemblies 102 to clip together a section of tissue.

Figure 35:
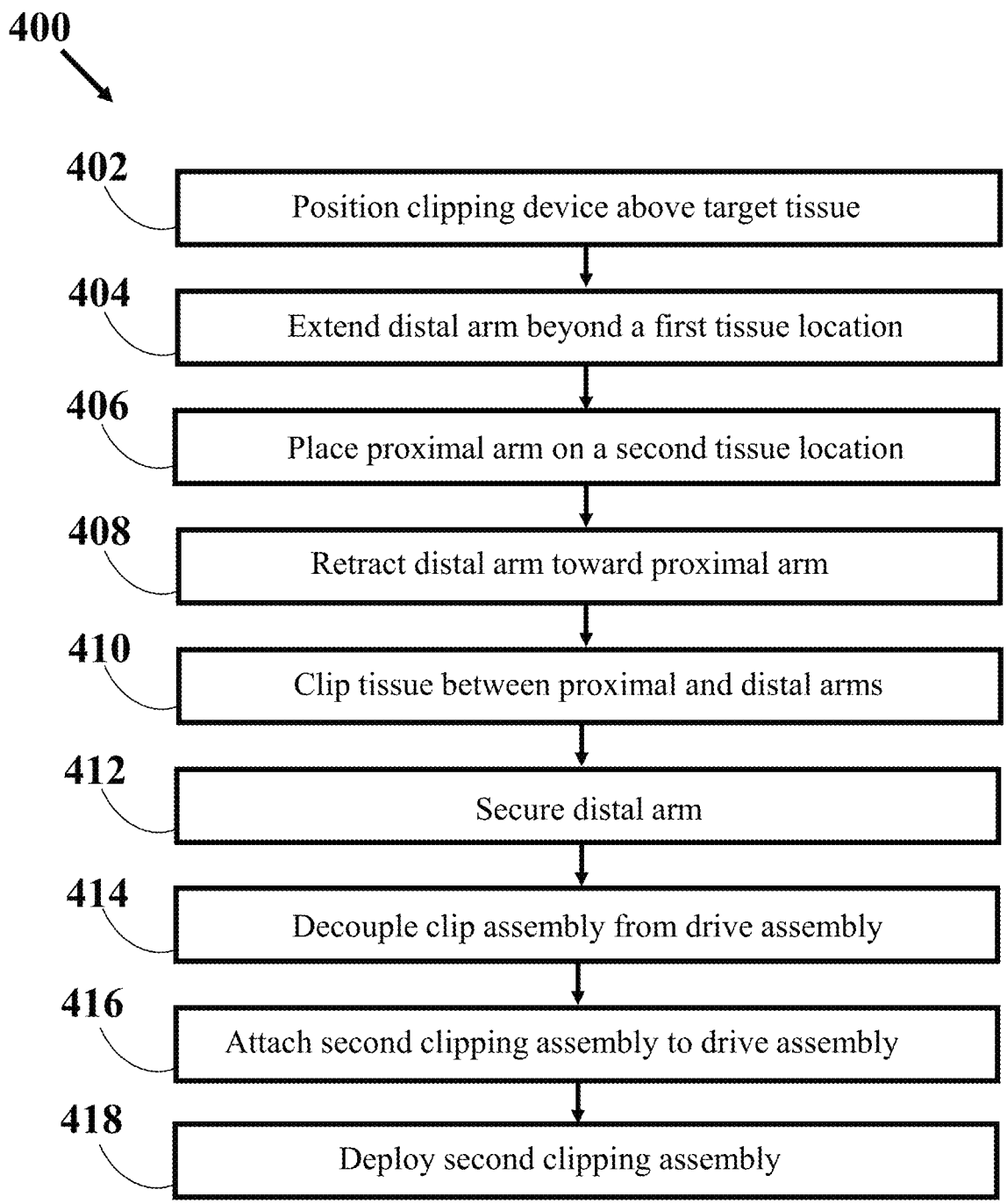
FIG. 35 is an illustrative example depicting a methodology for clipping tissue with a tissue clipping device.

FIG. 35 illustrates an exemplary methodology 400 relating to clipping tissue, such as to close a defect. While the methodology is shown as being a series of acts that are performed in a sequence, it is to be understood and appreciated that the methodology is not limited by the order of the sequence. For example, some acts can occur concurrently with another act. Further, in some instances, not all acts may be required to implement the methodology described herein.

At step 402, a clipping device is positioned above target tissue, such as a defect. The tissue may be identified using one or more cameras operably connected to an endoscope. The clipping device may include a tissue clipping assembly that is positioned above the target tissue. The tissue clipping assembly may be coupled to a drive assembly such that a user may control the position and rotation of the tissue clipping assembly. The tissue clipping assembly and portions of the drive assembly may be extended through an endoscope to the desired location.

At step 404, a distal arm of the tissue clipping assembly is extended beyond a first tissue location, such as beyond a first side of the identified defect. The distal arm may be extended from a distal end of the endoscope and a distal end of a catheter of the drive assembly. The distal arm may be extended via a drive element, such as via a handle, to linearly translate and rotate the distal arm beyond the first tissue location. The distal arm may be extended such that a grasping portion of the distal arm is positioned linearly beyond (e.g., distally to) the tissue at the first location. The distal arm, such as the grasping portion of the distal arm, may be inserted into the tissue at the first location to graspingly secure the tissue at the first location.

In some embodiments, one or more tines of the distal arm are oriented to face and grasp the tissue at the first location. The orientation of the tines may be achieved using one or more indicia, such as arrows on the clip to indicate the top of the tissue clipping device.

In some embodiments, the tissue at the first location may be pulled or dragged proximally toward a second tissue location by proximally retracting the endoscope and/or catheter of the drive assembly without actuating the tissue clipping device. This may permit the tissue clipping device to close defects larger than an actual opening of the tissue clipping device.

At step 406, a proximal arm of the tissue clipping device is placed on tissue at a second location. The second location may be substantially proximal to the first location, such as a second side of the defect opposite the first side of the defect. The proximal arm may be positioned at the second location via the catheter. The proximal arm may be inserted into the tissue at the second location to graspingly secure the tissue at the second location. In some embodiments, one or more tines of the proximal arm are oriented to face and grasp the tissue at the second location. In some embodiments, the proximal arm is fixedly attached to a collar of the tissue clipping assembly.

At step 408, the distal arm is retracted toward the proximal arm. The distal arm may be linearly retracted toward the proximal arm such that the tissue grasped by the distal arm at the first location is pulled toward the tissue grasped by the proximal arm at the second location. In some embodiments, the proximal arm remains fixed in position at the second location. Optionally, if it is determined that the tissue is not grasped properly, the distal arm and/or the proximal arm may be maneuvered to release the tissue such that tissue may be regrasped.

At step 410, tissue is clipped between the proximal and distal arms. The distal arm may be retracted toward the proximal arm such that the tissue grasped at the first location is substantially adjacent to the tissue grasped at the second location. The distal arm may be retracted such that the distal arm substantially abuts the proximal arm to clip the tissue between the distal arm and the proximal arm. For example, the retraction of the distal arm grasping tissue at a first side of a defect toward the proximal arm grasping tissue at a second side of the defect may substantially close the defect. The distal arm may be retracted toward the proximal arm such that the tissue clipping assembly is moved to a closed position, as described above. In some embodiments, tissue recruited by the distal arm is disposed in the collar when the tissue is clipped between the proximal and distal arms.

At step 412, the distal arm is secured relative to the other components of the tissue clipping assembly. The distal arm may be secured in position to maintain the tissue clipping assembly in the closed position such that the tissue clipping assembly keeps the tissue clipped. In some embodiments, the distal arm includes one or more tabs which are lockingly received in the collar of the tissue clipping assembly to secure the position of the distal arm in the collar. The proximal arm may be integral with the collar.

At step 414, the tissue clipping assembly may be decoupled from the drive assembly, such as to deploy the tissue clipping assembly in the body, such as to maintain the clipping of the tissue. The distal arm may be decoupled from the drive element and the collar may be decoupled from the catheter to decouple the tissue clipping assembly from the drive assembly. The distal arm may be decoupled from the drive element via continued proximal retraction of the drive element. For example, the distal arm may be operably coupled to the distal end of the drive element via a coupler or coupling projection that decouples the distal arm from the drive element when the distal arm is in the closed position and the drive element is proximally retracted, as described above. The collar may also be decoupled from the catheter via continued proximal retraction of the drive element, as described above. After the tissue clipping assembly is decoupled from the drive assembly, the tissue clipping assembly may remain in the body to continue to clip the tissue and the drive assembly may be withdrawn from the body. The endoscope may also be withdrawn from the body.

In some embodiments, the distal end of the catheter is coupled with a connector that operably couples the catheter to the proximal end of the collar. During operation, and alignment spacer may be disposed within the coupling between the collar and the connector, such as in abutment with the connecting portions of the collar and the connector, such that the alignment spacer maintains the coupling between the collar and the connector, as described above. When the distal arm is in the closed position, further proximal retraction of the drive element may move the alignment spacer such that the alignment member no longer maintains the coupling of the collar and the connector such that the collar may be decoupled from the catheter.

As described above, the drive element may have a proximal portion with a narrower cross section than a distal portion of the drive element. The proximal portion may operably be coupled to the distal arm during operation, such as to linearly translate the distal arm. After the tissue clipping assembly has been moved to the closed position, such as to clip tissue, the drive element may be proximally retracted such that the distal end of the drive element decouples from the distal arm and the proximal portion of the drive wire is retracted from the alignment spacer. Further proximal retraction of the drive element may cause a distal end of the drive element to abut or otherwise contact an alignment spacer. Proximal retraction of the drive element may pull the alignment spacer proximally such that the alignment spacer no longer maintains the coupling of the collar and the connector such that the collar may be decoupled from the connector.

At step 416, a second tissue clipping assembly may optionally be attached to the drive assembly. The second tissue assembly may be substantially similar to the first tissue clipping assembly. The drive element of the drive assembly may be coupled with the distal arm of the second tissue clipping assembly and the catheter may be coupled with a collar of the tissue clipping assembly such that the tissue clipping assembly may be maneuvered by the drive assembly, as described above.

At step 418, the second tissue clipping assembly may be deployed via the drive assembly to clip tissue at a second location. Steps 402 through 414 may be repeated with the second tissue clipping assembly to deploy the second issue clipping assembly. In some embodiments, the second tissue clipping assembly is deployed substantially parallel to the first tissue clipping assembly to clip tissue adjacent and/or parallel to the tissue clipped by the first tissue clipping assembly. For example, the second tissue clipping assembly may clip tissue across a width of the identified defect at a location spaced apart from the first tissue clipping assembly to clip tissue along a length of a larger defect.

Steps 416 and 418 may be repeated with additional tissue clipping assemblies as desired. For example, additional tissue clipping assembly or assemblies may be deployed in line with and spaced apart from the first and second tissue clipping assemblies, such as to close larger defects. The additional tissue clipping assemblies may be deployed to clip tissue across a width of the identified defect at a location spaced apart from the first and second tissue clipping assemblies to clip tissue along the length of a larger defect.

It is to be understood that the detailed description is intended to be illustrative, and not limiting to the embodiments described. Other embodiments will be apparent to those of skill in the art upon reading and understanding the above description. Moreover, in some instances, elements described with one embodiment may be readily adapted for use with other embodiments. Therefore, any products, methods and/or systems described herein are not limited to the specific details, the representative embodiments, and/or the illustrative examples shown and described. Accordingly, departures may be made from such details without departing from the spirit or scope of the general aspects of the present disclosure.

Additionally, the components and materials described hereinafter as making up the various embodiments are intended to be illustrative and not restrictive. It should be appreciated that many suitable components and materials that would perform the same or a similar function as the materials described herein are intended to be embraced within the scope of embodiments of the present disclosure.

We claim:

1. A medical device for clipping tissue, the device comprising:
    a catheter;
    a collar having a proximal arm extending in a distal direction, a proximal end of the collar being coupled with a distal end of the catheter;
    a distal arm having an extension portion and a grasping portion; and
    a drive element extending through the catheter and coupled with the distal arm;
    wherein the drive element is operable to linearly translate the distal arm through the collar; and
    wherein the medical device is operable to clip tissue between the proximal arm and the distal arm by linearly retracting the distal arm toward the proximal arm.

2. The medical device of claim 1, wherein the distal arm has a distal tine with a tip and barbs configured to grasp tissue.

3. The medical device of claim 1, wherein the proximal arm has a proximal tine with a tip and barbs configured to grasp tissue.

4. The medical device of claim 1, wherein the proximal arm is fixed to the collar.

5. The medical device of claim 1, wherein the distal arm includes a locking projection configured to be received in a receiving portion of the collar to lock the distal arm in a closed position.

6. The medical device of claim 1, wherein distal arm includes a housing configured to shroud the proximal arm when the tissue clipping device is in a closed position.

7. The medical device of claim 1, wherein the proximal arm is pivotable about the collar.

8. A medical device for clipping tissue, the device comprising:
- a tissue clipping assembly operable to clip tissue, the tissue clipping assembly comprising:
  - a distal arm;
  - a collar; and
  - a proximal arm;
- a drive assembly operable to actuate the tissue clipping assembly, the drive assembly comprising:
  - a handle;
  - a catheter; and
  - a drive element with a proximal end secured to the handle and a distal end operably coupled with a proximal end of the distal arm; and
- wherein the drive element is operable to linearly translate the distal arm to clip tissue between the distal arm and the proximal arm; and
- wherein the tissue clipping assembly is operably decoupled from the drive assembly after the tissue clipping assembly has clipped tissue.

9. The medical device of claim 8, wherein the drive element has a proximal portion extending through the catheter and a distal portion coupled with the distal arm, wherein the distal portion has a rectangular cross section.

10. The medical device of claim 8, wherein the distal arm includes a coupling projection configured to releasably couple the distal arm with the drive element.

11. The medical device of claim 8, wherein the drive assembly further comprises a coupler operable to couple the drive element with the distal arm.

12. The medical device of claim 8, wherein the drive assembly further comprises a connector operable to couple the catheter with the collar.

13. The medical device of claim 12, wherein the drive assembly further comprises an alignment spacer operable to maintain the coupling of the connector and the collar.

14. The medical device of claim 8, wherein the distal arm is decoupled from the drive element and the collar is decoupled from the catheter by proximal retraction of the drive element.

15. A method for treating a defect with a tissue recruiting device, the method comprising the steps of:
- positioning a tissue clipping assembly above the defect;
- linearly extending a distal arm of the tissue clipping assembly to grasp a first side of the defect via a drive assembly;
- grasping a second side of the defect with a proximal arm of the tissue clipping assembly;
- retracting the distal arm toward the proximal arm;
- clipping tissue between the distal and proximal arms; and
- decoupling the tissue clipping assembly from the drive assembly.

16. The method of claim 15, further comprising the step of locking the distal arm in a collar of the tissue clipping assembly.

17. The method of claim 15, wherein the distal arm is coupled to a handle of the drive assembly by a drive element.

18. The method of claim 17, wherein the distal arm is coupled with the drive element via a coupler.

19. The method of claim 15, wherein the collar is operably coupled to a catheter and the collar is decoupled from the catheter by proximal retraction of the drive element.

20. The method of claim 15, further comprising the step of attaching a second tissue clipping assembly to the drive assembly.

* * * * *